(12) United States Patent
Zhou et al.

(10) Patent No.: US 11,103,493 B2
(45) Date of Patent: Aug. 31, 2021

(54) SUBSTITUTED PYRIDINYL COMPOUNDS AS INDOLEAMINE 2,3-DIOXYGENASE (IDO) INHIBITORS

(71) Applicant: Merck Sharp & Dohme Corp., Rahway, NJ (US)

(72) Inventors: Hua Zhou, Acton, MA (US); Xavier Fradera, Brookline, MA (US); Yongxin Han, Needham, MA (US); Meredeth A. McGowan, Boston, MA (US); Nunzio Sciammetta, Sudbury, MA (US); Catherine White, Newton Center, MA (US); Wensheng Yu, Edison, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/631,192

(22) PCT Filed: Jul. 30, 2018

(86) PCT No.: PCT/US2018/044274
§ 371 (c)(1),
(2) Date: Jan. 15, 2020

(87) PCT Pub. No.: WO2019/027856
PCT Pub. Date: Feb. 7, 2019

(65) Prior Publication Data
US 2020/0215042 A1   Jul. 9, 2020

Related U.S. Application Data

(60) Provisional application No. 62/540,318, filed on Aug. 2, 2017.

(51) Int. Cl.
| | |
|---|---|
| *A61K 31/444* | (2006.01) |
| *A61K 31/4439* | (2006.01) |
| *A61K 45/06* | (2006.01) |
| *C07D 401/08* | (2006.01) |
| *C07D 401/14* | (2006.01) |
| *C07D 471/04* | (2006.01) |

(52) U.S. Cl.
CPC ........ *A61K 31/444* (2013.01); *A61K 31/4439* (2013.01); *A61K 45/06* (2013.01); *C07D 401/08* (2013.01); *C07D 401/14* (2013.01); *C07D 471/04* (2013.01)

(58) Field of Classification Search
CPC .. A61K 31/4439; A61K 45/06; C07D 401/08; C07D 401/14; C07D 471/04
USPC ....................................................... 514/303
See application file for complete search history.

(56) References Cited

U.S. PATENT DOCUMENTS

| 8,580,829 B2 | 11/2013 | Bartolozzi et al. | |
|---|---|---|---|
| 9,096,531 B2 * | 8/2015 | Masaki ................ | C07D 473/00 |
| 9,174,980 B2 | 11/2015 | Bartolozzi et al. | |
| 2016/0333009 A1 | 11/2016 | Bartlett et al. | |
| 2016/0376270 A1 | 12/2016 | Bates et al. | |
| 2018/0186787 A1 * | 7/2018 | Cowley ................ | C07D 471/04 |
| 2018/0258075 A1 * | 9/2018 | Cowley ..................... | A61P 9/00 |
| 2018/0362482 A1 * | 12/2018 | Han ......................... | A61P 31/14 |
| 2019/0144433 A1 * | 5/2019 | Han ........................ | A61K 45/06 |
| | | | 514/252.01 |
| 2020/0024236 A1 * | 1/2020 | Lewis ................... | A61K 31/423 |
| 2020/0095212 A1 * | 3/2020 | Liu ........................... | A61P 27/00 |
| 2020/0102278 A1 * | 4/2020 | Guo ......................... | A61P 25/28 |
| 2020/0216425 A1 * | 7/2020 | Han .................... | A61K 31/4418 |
| 2020/0216443 A1 * | 7/2020 | Zhou .................... | C07D 235/10 |
| 2020/0239423 A1 * | 7/2020 | White .................. | C07D 305/08 |
| 2020/0277252 A1 * | 9/2020 | McGowan ........... | C07D 285/06 |
| 2020/0290996 A1 * | 9/2020 | White .................. | C07D 213/85 |

FOREIGN PATENT DOCUMENTS

| FR | 2104717 A1 * | 4/1972 | .............. C07F 9/113 |
|---|---|---|---|
| WO | WO-2016018701 A1 * | 2/2016 | ........... C07D 401/06 |
| WO | WO-2018039512 A1 * | 3/2018 | ........... C07D 471/04 |
| WO | WO-2019027855 A1 * | 2/2019 | ........... C07D 235/14 |
| WO | WO-2019101188 A1 * | 5/2019 | ......... C07D 491/056 |
| WO | WO-2019111107 A1 * | 6/2019 | .............. A61P 31/14 |
| WO | WO-2019141153 A1 * | 7/2019 | ......... A61K 31/4709 |
| WO | WO-2020251871 A2 * | 12/2020 | ........... C07D 471/04 |

OTHER PUBLICATIONS

Brochez; European Journal of Cancer 2017, 76, 167-182. doi: 10.1016/j.ejca.2017.01.011 (Year: 2017).*
Prendergast; Cancer Res 2017, 77, 6795-6811. doi: 10.1158/0008-5472.CAN-17-2285 (Year: 2017).*
PubChem, Compound Summary for CID 122186635, Create Date 26-10-26.
European Search Report, Application No. 188402614, dated Feb. 10, 2021, 22 pages.

* cited by examiner

Primary Examiner — Daniel R Carcanague
(74) Attorney, Agent, or Firm — Yong Zhao; Anna L. Cocuzzo

(57) ABSTRACT

Disclosed herein is a compound of formula (I), or a pharmaceutically acceptable salt thereof: (I). Also disclosed herein are uses of the compounds disclosed herein in the potential treatment or prevention of an IDO-associated disease or disorder. Also disclosed herein are compositions comprising a compound disclosed herein. Further disclosed herein are uses of the compositions in the potential treatment or prevention of an IDO-associated disease or disorder.

18 Claims, No Drawings

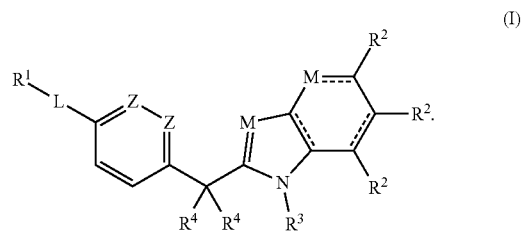

SUBSTITUTED PYRIDINYL COMPOUNDS AS INDOLEAMINE 2,3-DIOXYGENASE (IDO) INHIBITORS

CROSS REFERENCE TO RELATED APPLICATIONS

The present application is the 371 national phase application of International Application No. PCT/US2018/044274, filed Jul. 30, 2018, which claims the benefit of U.S. Provisional Application No. 62/540,318, filed Aug. 2, 2017, hereby incorporated by reference in their entirety.

BACKGROUND OF THE INVENTION

Tryptophan (Trp) is an essential amino acid required for the biosynthesis of proteins, niacin and the neurotransmitter 5-hydroxytryptamine (serotonin). The enzyme indoleamine 2,3-dioxygenase (IDO) catalyzes the first and rate limiting step in the degradation of L-tryptophan to N-formyl-kynurenine. In human cells, a depletion of Trp resulting from IDO activity is a prominent gamma interferon (EFN-γ)-inducible antimicrobial effector mechanism. IFN-γ stimulation induces activation of IDO, which leads to a depletion of Trp, thereby arresting the growth of Trp-dependent intracellular pathogens such as *Toxoplasma gondii* and *Chlamydia trachomatis*. IDO activity also has an antiproliferative effect on many tumor cells, and IDO induction has been observed in vivo during rejection of allogeneic tumors, indicating a possible role for this enzyme in the tumor rejection process (Daubener, et al, 1999, Adv. Exp. Med. Biol, 467: 517-24; Taylor, et al, 1991, FASEB J., 5: 2516-22).

It has been observed that HeLa cells co-cultured with peripheral blood lymphocytes (PBLs) acquire an immunoinhibitory phenotype through up-regulation of IDO activity. A reduction in PBL proliferation upon treatment with interleukin-2 (IL2) was believed to result from IDO released by the tumor cells in response to IFN-γ secretion by the PBLs. This effect was reversed by treatment with 1-methyl-tryptophan (IMT), a specific IDO inhibitor. It was proposed that IDO activity in tumor cells may serve to impair antitumor responses (Logan, et al, 2002, Immunology, 105: 478-87).

Several lines of evidence suggest that IDO is involved in induction of immune tolerance. Studies of mammalian pregnancy, tumor resistance, chronic infections and autoimmune diseases have shown that cells expressing IDO can suppress T-cell responses and promote tolerance. Accelerated Trp catabolism has been observed in diseases and disorders associated with cellular immune activation, such as infection, malignancy, autoimmune diseases and AIDS, as well as during pregnancy. For example, increased levels of IFNs and elevated levels of urinary Trp metabolites have been observed in autoimmune diseases; it has been postulated that systemic or local depletion of Trp occurring in autoimmune diseases may relate to the degeneration and wasting symptoms of these diseases. In support of this hypothesis, high levels of IDO were observed in cells isolated from the synovia of arthritic joints. IFNs are also elevated in human immunodeficiency virus (HIV) patients and increasing IFN levels are associated with a worsening prognosis. Thus, it was proposed that IDO is induced chronically by HIV infection, and is further increased by opportunistic infections, and that the chronic loss of Trp initiates mechanisms responsible for cachexia, dementia and diarrhea and possibly immunosuppression of AIDS patients (Brown, et al., 1991, Adv. Exp. Med. Biol, 294: 425-35). To this end, it has recently been shown that IDO inhibition can enhance the levels of virus-specific T cells and, concomitantly, reduce the number of virally-infected macrophages in a mouse model of HIV (Portula et al., 2005, Blood, 106: 2382-90).

IDO is believed to play a role in the immunosuppressive processes that prevent fetal rejection in utero. More than 40 years ago, it was observed that, during pregnancy, the genetically disparate mammalian conceptus survives in spite of what would be predicted by tissue transplantation immunology (Medawar, 1953, Symp. Soc. Exp. Biol. 7: 320-38). Anatomic separation of mother and fetus and antigenic immaturity of the fetus cannot fully explain fetal allograft survival. Recent attention has focused on immunologic tolerance of the mother. Because IDO is expressed by human syncytiotrophoblast cells and systemic tryptophan concentration falls during normal pregnancy, it was hypothesized that IDO expression at the maternal-fetal interface is necessary to prevent immunologic rejection of the fetal allografts. To test this hypothesis, pregnant mice (carrying syngeneic or allogeneic fetuses) were exposed to IMT, and a rapid, T cell-induced rejection of all allogeneic conception was observed. Thus, by catabolizing tryptophan, the mammalian conceptus appears to suppress T-cell activity and defends itself against rejection, and blocking tryptophan catabolism during murine pregnancy allows maternal T cells to provoke fetal allograft rejection (Moan, et al., 1998, Science, 281: 1191-3).

Further evidence for a tumoral immune resistance mechanism based on tryptophan degradation by IDO comes from the observation that most human tumors constitutively express IDO, and that expression of IDO by immunogenic mouse tumor cells prevents their rejection by preimmunized mice. This effect is accompanied by a lack of accumulation of specific T cells at the tumor site and can be partly reverted by systemic treatment of mice with an inhibitor of IDO, in the absence of noticeable toxicity. Thus, it was suggested that the efficacy of therapeutic vaccination of cancer patients might be improved by concomitant administration of an IDO inhibitor (Uyttenhove et al., 2003, Nature Med., 9: 1269-74). It has also been shown that the IDO inhibitor, 1-MT, can synergize with chemotherapeutic agents to reduce tumor growth in mice, suggesting that IDO inhibition may also enhance the anti-tumor activity of conventional cytotoxic therapies (Muller et al, 2005, Nature Med., 11: 312-9).

One mechanism contributing to immunologic unresponsiveness toward tumors may be presentation of tumor antigens by tolerogenic host APCs. A subset of human IDO-expressing antigen-presenting cells (APCs) that coexpressed CD123 (IL3RA) and CCR6 and inhibited T-cell proliferation have also been described. Both mature and immature CD123-positive dendritic cells suppressed T-cell activity, and this IDO suppressive activity was blocked by 1MT (Munn, et al, 2002, Science, 297: 1867-70). It has also been demonstrated that mouse tumor-draining lymph nodes (TDLNs) contain a subset of plasmacytoid dendritic cells (pDCs) that constitutively express immunosuppressive levels of IDO. Despite comprising only 0.5% of lymph node cells, in vitro, these pDCs potently suppressed T cell responses to antigens presented by the pDCs themselves and also, in a dominant fashion, suppressed T cell responses to third-party antigens presented by nonsuppressive APCs. Within the population of pDCs, the majority of the functional IDO-mediated suppressor activity segregated with a novel subset of pDCs coexpressing the B-lineage marker CD19. Thus, it was hypothesized that IDO-mediated suppression by pDCs in TDLNs creates a local microenvironment that is potently suppressive of host antitumor T cell responses (Munn, et al., 2004, J. Clin. Invest, 114(2): 280-90).

IDO degrades the indole moiety of tryptophan, serotonin and melatonin, and initiates the production of neuroactive and immunoregulatory metabolites, collectively known as kynurenines. By locally depleting tryptophan and increasing proapoptotic kynurenines, IDO expressed by dendritic cells (DCs) can greatly affect T-cell proliferation and survival. IDO induction in DCs could be a common mechanism of deletional tolerance driven by regulatory T cells. Because such tolerogenic responses can be expected to operate in a variety of physiopathological conditions, tryptophan metabolism and kynurenine production might represent a crucial interface between the immune and nervous systems (Grohmann, et al, 2003, Trends Immunol, 24: 242-8). In states of persistent immune activation, availability of free serum Trp is diminished and, as a consequence of reduced serotonin production, serotonergic functions may also be affected (Wirleitner, et al., 2003, Curr. Med. Chem., 10: 1581-91).

In light of the potential role for IDO in immunosuppression, tumor resistance and/or rejection, chronic infections, HIV-infection, AIDS (including its manifestations such as cachexia, dementia and diarrhea), autoimmune diseases or disorders (such as rheumatoid arthritis), and immunologic tolerance and prevention of fetal rejection in utero, therapeutic agents aimed at suppression of tryptophan degradation by inhibiting IDO activity are desirable. Inhibitors of IDO can be used to activate T cells and therefore enhance T cell activation when the cells are suppressed by pregnancy, malignancy or a virus such as HIV. Inhibition of IDO may also be an important treatment strategy for patients with neurological or neuropsychiatric diseases or disorders such as depression. Compounds disclosed herein are useful in the potential treatment or prevention of IDO-related diseases.

SUMMARY OF THE INVENTION

Disclosed herein are novel compounds of formula (I), which are inhibitors of the IDO enzymes. Also disclosed herein are uses of these compounds in the potential treatment or prevention of an IDO-associated disease or disorder. Also disclosed herein are compositions comprising one or more of the compounds. Further disclosed herein are uses of these compositions in the potential prevention or treatment of an IDO-associated disease or disorder.

DETAILED DESCRIPTION OF THE INVENTION

Disclosed herein is a compound of formula (I), or a pharmaceutically acceptable salt, solvate or hydrate thereof:

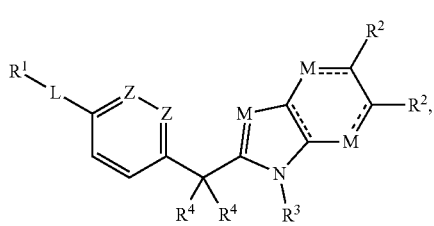

(I)

wherein:
L is selected from (1) a bond, (2) —NHC(O)— and (3) —C(O)NH—;
=M- is selected from (1) =$CR^a$— and (2) =N—;
each occurrence of ═M— is independently selected from (1) =$CR^a$—, (2) —$CR^aR^a$—, (3) =N— and (4) —$NR^a$—;
wherein each occurrence of $R^a$ is independently selected from:
(a) H,
(b) —OH,
(c) halogen,
(d) —CN,
(e) $C_{1-6}$ alkyl,
(f) —O—$C_{1-6}$ alkyl,
(g) —C(O)—$R^5$, wherein $R^5$ is selected from (a) —OH, (b) —O—$C_{1-6}$ alkyl and (c) a 5- or 6-membered heterocyclyl, optionally substituted with —OH, and
(h) 5- or 6-membered heteroaryl;
wherein each of the $C_{1-6}$ alkyl of (e) and (f) is optionally substituted with 1 to 3 substituents independently selected from (a) —OH, (b) —C(O)OH and (c) halogen;
each dotted bond "═══" is independently selected from (1) a double bond and (2) a single bond;
one Z is =CH— and the other Z is =N—;
$R^1$ is selected from:
(1) $C_{1-6}$ alkyl,
(2) $C_{3-6}$ cycloalkyl,
(3) aryl and
(4) 5- or 6-membered heteroaryl;
wherein each of the aryl of (3) and the heteroaryl of (4) is optionally substituted with 1 to 3 substituents independently selected from (a) halogen, (b) —CN, (c) —$NH_2$, (d) $C_{1-6}$ alkyl, optionally substituted with 1 to 3 halogens, (e) —O—$C_{1-6}$ alkyl and (f) $C_{3-6}$ cycloalkyl; each occurrence of $R^2$ is independently selected from:
(1) H,
(2) —OH,
(3) halogen,
(4) —CN,
(5) $C_{1-6}$ alkyl,
(6) —O—$C_{1-6}$ alkyl,
(7) —C(O)—$R^5$, wherein $R^5$ is selected from (a) —OH, (b) —O—$C_{1-6}$ alkyl and (c) a 5- or 6-membered heterocyclyl, optionally substituted with —OH, and
(8) 5- or 6-membered heteroaryl;
wherein each of the $C_{1-6}$ alkyl of (5) and (6) is optionally substituted with 1 to 3 substituents independently selected from (a) —OH, (b) —C(O)OH and (c) halogen;
or alternatively, two adjacent $R^2$ groups together with the carbons to which they are attached form a 5- or 6-membered heterocyclic ring comprising 1 to 2 hetero atoms independently selected from O, S and NH, wherein the 5- or 6-membered heterocyclic ring is optionally substituted with an oxo;
$R^3$ is selected from (1) H and (2) $C_{1-6}$ alkyl optionally substituted with a halogen or —OH; and one $R^4$ is H and the other $R^4$ is selected from (1) —OH, (2) $C_{1-6}$ alkyl (3) —O—$C_{1-6}$ alkyl and (4) halogen;
or alternatively, two $R^4$ groups together with the carbon to which they are attached form a 4- or 5-membered cycloalkyl ring or a heterocyclic ring containing one oxygen atom; each ring is optionally substituted with —OH, halogen or $C_{1-6}$ alkyl.

In one embodiment of the compound of formula (I), or a pharmaceutically acceptable salt, solvate or hydrate thereof, the compound is of formula (Ia):

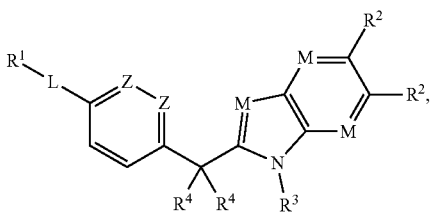

wherein:
each occurrence of =M- is independently selected from (1) =CR$^a$— and (2) =N—;
R$^1$ is selected from:
(1) C$_{1-6}$ alkyl,
(2) C$_{3-6}$ cycloalkyl,
(3) phenyl and
(4) pyridinyl;
wherein each of the aryl of (3) and the pyridinyl of (4) is optionally substituted with 1 to 3 substituents independently selected from (a) halogen, (b) —CN, (c) —NH$_2$, (d) —CH$_3$, (e) —CF$_3$, (f) —O—CH$_3$ and (g) C$_{3-6}$ cycloalkyl;
each occurrence of R$^2$ is independently selected from:
(1) H,
(2) —OH,
(3) halogen,
(4) —CN,
(5) C$_{1-6}$ alkyl,
(6) —O—C$_{1-6}$ alkyl,
(7) —C(O)—R$^5$, wherein R$^5$ is selected from (a) —OH, (b) —O—C$_{1-6}$ alkyl and (c) a 5- or 6-membered heterocyclyl, optionally substituted with —OH, and
(8) 5- or 6-membered heteroaryl;
wherein each of the C$_{1-6}$ alkyl of (5) and (6) is optionally substituted with 1 to 3 substituents independently selected from (a) —OH, (b) —C(O)OH and (c) halogen
or alternatively, two adjacent R$^2$ groups together with the carbons to which they are attached form a 5- or 6-membered heterocyclic group comprising 1 to 2 hetero atoms independently selected from O, S and N, wherein the 5- or 6-membered heterocyclic group is optionally substituted with an oxo;
R$^3$ is selected from (1) H and (2) C$_{1-6}$ alkyl optionally substituted with a halogen or —OH; and
one R$^4$ is H and the other R$^4$ is selected from (1) —OH, (2) C$_{1-4}$ alkyl and (3) —O—C$_{1-4}$ alkyl;
or alternatively, two R$^4$ groups together with the carbon to which they are attached form a cyclobutyl ring or an oxetanyl ring; each ring is optionally substituted with —OH, halogen or C$_{1-6}$ alkyl.

In one embodiment of the compound of formula (I), or a pharmaceutically acceptable salt, solvate or hydrate thereof, the compound is of formula (Ib):

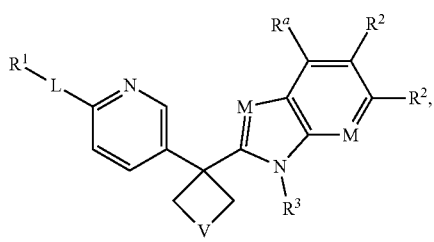

wherein:
L is selected from (1) a bond, (2) —NHC(O)— and (3) —C(O)NH—;

each occurrence of =M- is independently selected from (1) =CR$^a$— and (2) =N—;
V is selected from (1) —CR$^b$R$^b$—, —NR$^c$— and —O—; wherein each occurrence of R$^b$ is independently selected from (a) H, (b) —OH, (c) halogen and (d) C$_{1-6}$ alkyl; and R$^c$ is selected from (a) H and (b) C$_{1-6}$ alkyl;
R$^1$ is selected from:
(1) C$_{1-6}$ alkyl,
(2) C$_{3-6}$ cycloalkyl,
(3) aryl and
(4) 5- or 6-membered heteroaryl;
wherein each of the aryl of (3) and the heteroaryl of (4) is optionally substituted with 1 to 3 substituents independently selected from (a) halogen, (b) —CN, (c) —CF$_3$, (d) —NH$_2$, (e) C$_{1-6}$ alkyl and (f) C$_{3-6}$ cycloalkyl;
each occurrence of R$^2$ is independently selected from:
(1) H,
(2) —OH,
(3) halogen,
(4) —CN,
(5) C$_{1-6}$ alkyl,
(6) —O—C$_{1-6}$ alkyl, and
(7) 5- or 6-membered heteroaryl;
wherein each of the C$_{1-6}$ alkyl of (5) and (6) is optionally substituted with 1 to 3 substituents independently selected from (a) —OH, (b) —C(O)OH and (c) halogen;
or alternatively, two adjacent R$^2$ groups together with the carbons to which they are attached form a 5- or 6-membered heterocyclic group which is optionally substituted with an oxo; and
R$^3$ is selected from (1) H and (2) C$_{1-6}$ alkyl optionally substituted with halogen or —OH.

In one embodiment of the compound of formula (I), or a pharmaceutically acceptable salt, solvate or hydrate thereof:
L is selected from (1) —NHC(O)— and (2) —C(O)NH—;
each occurrence of M is independently selected from (1) =CH— and (2) =N—; wherein R$^a$ is selected from (a) H, (b) halogen and (c) C$_{1-6}$ alkyl;
V is selected from (1) —CR$^b$R$^b$— and (2) —NR$^c$—; wherein each occurrence of R$^b$ is independently selected from (a) H, (b) —OH, (c) halogen and (d) C$_{1-6}$ alkyl; and R$^c$ is selected from (a) H and (b) C$_{1-6}$ alkyl;
R$^1$ is selected from (1) C$_{1-6}$ alkyl, (b) C$_{3-6}$ cycloalkyl, (c) aryl and (d) 5- or 6-membered heteroaryl; wherein each of the aryl of (c) and the heteroaryl of (d) is optionally substituted with 1 to 3 substituents independently selected from (a) halogen, (b) —CN, (c) —CF$_3$, (d) —NH$_2$, (e) C$_{1-6}$ alkyl and (f) C$_{3-6}$ cycloalkyl;
each occurrence of R$^2$ is independently selected from (1) H, (2) —OH, (3) halogen, (4) —CN, (5) C$_{1-6}$ alkyl, (6) —O—C$_{1-6}$ alkyl and (7) 5- or 6-membered heteroaryl; wherein each of the C$_{1-6}$ alkyl of (5) and (6) is optionally substituted with 1 to 3 substituents independently selected from (a) —OH and (b) halogen;
or alternatively, two adjacent R$^2$ groups together with the carbons to which they are attached form a 5- or 6-membered heterocyclic group which is optionally substituted with an oxo; and
R$^3$ is selected from H and C$_{1-6}$ alkyl optionally substituted with halogen or —OH.

In one embodiment of the compound of formula (I), or a pharmaceutically acceptable salt, solvate or hydrate thereof:
when present, each M is =N—;
when present, V is —CR$^b$R$^b$—; wherein each occurrence of R$^b$ is independently selected from (a) H, (b) —OH, (c) halogen and (d) C$_{1-6}$ alkyl;

$R^1$ is selected from (1) $C_{1-6}$ alkyl, (2) $C_{3-6}$ cycloalkyl, (3) aryl and (4) 5- or 6-membered heteroaryl; wherein each of the aryl of (3) and the heteroaryl of (4) is optionally substituted with 1 to 3 substituents independently selected from (a) halogen, (b) —CN, (c) —CF$_3$, (d) —NH$_2$, (e) $C_{1-6}$ alkyl and (f) $C_{3-6}$ cycloalkyl;

each occurrence of $R^2$ is independently selected from (1) H, (2) halogen, (3) —CN and (4) $C_{1-6}$ alkyl; wherein the $C_{1-6}$ alkyl is optionally substituted with 1 to 3 halogens; and $R^3$ is selected from (1) H and (2) $C_{1-6}$ alkyl optionally substituted with —OH.

In one embodiment of the compound of formula (I), or a pharmaceutically acceptable salt, solvate or hydrate thereof: when present, one M is =CH$^a$— and the other M is =N—; when present, V is $CR^bR^b$; wherein each occurrence of $R^b$ is independently selected from (a) H, (b) —OH, (c) halogen and (d) $C_{1-6}$ alkyl; and $R^b$ is selected from (a) H and (b) $C_{1-6}$ alkyl;

$R^1$ is selected from (1) $C_{1-6}$ alkyl, (2) $C_{3-6}$ cycloalkyl, (3) aryl and (4) 5- or 6-membered heteroaryl; wherein each of the aryl of (3) and the heteroaryl of (4) is optionally substituted with 1 to 3 substituents independently selected from (a) halogen, (b) —CN, (c) —CF$_3$, (d) —NH$_2$, (e) $C_{1-6}$ alkyl and (f) $C_{3-6}$ cycloalkyl;

each occurrence of $R^2$ is independently selected from (1) H, (2) halogen, (3) —CN and (4) $C_{1-6}$ alkyl; wherein the $C_{1-6}$ alkyl is optionally substituted with 1 to 3 halogens; and $R^3$ is H.

In one embodiment of the compound of formula (I), or a pharmaceutically acceptable salt, solvate or hydrate thereof, the compound is of formula (Ic):

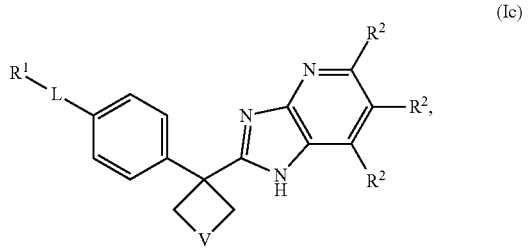

(Ic)

wherein:
L is selected from (1) —NHC(O)— and (2) —C(O)NH—;
V is selected from (1) —CR$^b$R$^b$— and —NR$^c$—; wherein each occurrence of $R^b$ is independently selected from (a) H, (b) —OH, (c) halogen and (d) $C_{1-6}$ alkyl; and $R^c$ is selected from (a) H and (b) $C_{1-6}$ alkyl;

$R^1$ is selected from (1) $C_{1-6}$ alkyl, (2) $C_{3-6}$ cycloalkyl, (3) aryl and (4) 5- or 6-membered heteroaryl; wherein each of the aryl of (3) and the heteroaryl of (4) is optionally substituted with 1 to 3 substituents independently selected from (a) halogen, (b) —CN, (c) —CF$_3$, (d) —NH$_2$, (e) $C_{1-6}$ alkyl and (f) $C_{3-6}$ cycloalkyl; and each occurrence of $R^2$ is independently selected from (1) H, (2) —OH, (3) halogen, (4) —CN, (5) $C_{1-6}$ alkyl, (6) —O—$C_{1-6}$ alkyl and (7) 5- or 6-membered heteroaryl; wherein each of the $C_{1-6}$ alkyl of (5) and (6) is optionally substituted with 1 to 3 substituents independently selected from (a) —OH and (b) halogen;

or alternatively, two adjacent $R^2$ groups together with the carbons to which they are attached form a 5- or 6-membered heterocyclic group which is optionally substituted with an oxo.

In one embodiment of the compound of formula (Ic), or a pharmaceutically acceptable salt, solvate or hydrate thereof:

L is selected from (1) —NHC(O)— and (2) —C(O)NH—;
V is (1) —CH$_2$— or (2) —CF$_2$—;
$R^1$ is selected from (1) $C_{3-6}$ cycloalkyl, (2) aryl and (3) 5- or 6-membered heteroaryl; wherein each of the aryl of (2) and the heteroaryl of (3) is optionally substituted with 1 to 3 substituents independently selected from (a) halogen, (b) —CN, (c) —CF$_3$, (d) $C_{1-6}$ alkyl and (e) $C_{3-6}$ cycloalkyl; and each occurrence of $R^2$ is independently selected from (1) H, (2) —OH, (3) halogen, (4) —CN, (5) $C_{1-6}$ alkyl, (6) —O—$C_{1-6}$ alkyl and (7) tetrazolyl; wherein each of the $C_{1-6}$ alkyl is optionally substituted with 1 to 3 substituents independently selected from (a) —OH and (b) halogen.

In one embodiment of the compound of formula (Ic), or a pharmaceutically acceptable salt, solvate or hydrate thereof:
$R^1$ is selected from (1) phenyl and (2) pyridinyl; wherein each of the phenyl and the pyridinyl is optionally substituted with 1 to 3 substituents independently selected from (a) halogen, (b) —CN, (c) —CF$_3$ and (d) $C_{1-6}$ alkyl; and each occurrence of $R^2$ is independently selected from (1) H, (2) halogen, (3) —CN, (4) $C_{1-6}$ alkyl and (5) —O—$C_{1-6}$ alkyl; wherein each of the $C_{1-6}$ alkyl is optionally substituted with 1 to 3 substituents independently selected from (a) —OH and (b) halogen.

In one embodiment of the compound of formula (I), or a pharmaceutically acceptable salt, solvate or hydrate thereof, the compound is of formula (Id):

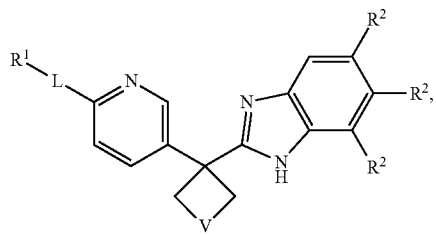

(Id)

wherein:
L is selected from (1) —NHC(O)— and (2) —C(O)NH—;
V is selected from —CR$^b$R$^b$— and —NR$^c$—; wherein each occurrence of $R^b$ is independently selected from (a) H, (b) —OH, (c) halogen and (d) $C_{1-6}$ alkyl; and $R^c$ is selected from (a) H and (b) $C_{1-6}$ alkyl;

$R^1$ is selected from (1) $C_{1-6}$ alkyl, (2) $C_{3-6}$ cycloalkyl, (3) aryl and (4) 5- or 6-membered heteroaryl; wherein each of the aryl of (3) and the heteroaryl of (4) is optionally substituted with 1 to 3 substituents independently selected from (a) halogen, (b) —CN, (c) —CF$_3$, (d) —NH$_2$, (e) $C_{1-6}$ alkyl and (f) $C_{3-6}$ cycloalkyl; and each occurrence of $R^2$ is independently selected from (1) H, (2) —OH, (3) halogen, (4) —CN, (5) $C_{1-6}$ alkyl, (6) —O—$C_{1-6}$ alkyl and (7) 5- or 6-membered heteroaryl; wherein each of the $C_{1-6}$ alkyl is optionally substituted with 1 to 3 substituents independently selected from (a) —OH and (b) halogen;

or alternatively, two adjacent $R^2$ groups together with the carbons to which they are attached form a 5- or 6-membered heterocyclic group which is optionally substituted with an oxo.

In one embodiment of the compound of formula (Ib), (Ic) or (Id), or a pharmaceutically acceptable salt, solvate or hydrate thereof:
L is selected from (1) —NHC(O)— and (2) —C(O)NH—;
V is —CH$_2$— or —CF$_2$—;
$R^1$ is selected from (1) $C_{3-6}$ cycloalkyl, (2) aryl and (3) 5- or 6-membered heteroaryl; wherein each of the aryl of (2) and the heteroaryl of (3) is optionally substituted with 1 to 3 substituents independently selected from (a) halogen, (b) —CN, (c) —CF$_3$, (d) C$_{1-6}$ alkyl and (e) C$_{3-6}$ cycloalkyl; and each occurrence of R$^2$ is independently selected from (1) H, (2) —OH, (3) halogen, (4) —CN, (5) C$_{1-6}$ alkyl, (6) —O—C$_{1-6}$ alkyl and (7) tetrazolyl; wherein each of the C$_{1-6}$ alkyl is optionally substituted with 1 to 3 substituents independently selected from (a) —OH and (b) halogen.

In one embodiment of the compound of formula (Ib), (Ic) or (Id), or a pharmaceutically acceptable salt, solvate or hydrate thereof:
R$^1$ is selected from (1) phenyl and (2) pyridinyl; wherein the phenyl and the pyridinyl is optionally substituted with 1 to 3 substituents independently selected from (a) halogen, (b) —CN, (c) —CF$_3$ and (d) C$_{1-6}$ alkyl; and
each occurrence of R$^2$ is independently selected from (1) H, (2) halogen, (3) —CN, (4) C$_{1-6}$ alkyl and (5) —O—C$_{1-6}$ alkyl; wherein each of the C$_{1-6}$ alkyl is optionally substituted with 1 to 3 substituents independently selected from (a) —OH and (b) halogen.

In one embodiment, a compound disclosed herein is of formula (Ie), or a pharmaceutically acceptable salt, solvate or hydrate thereof:

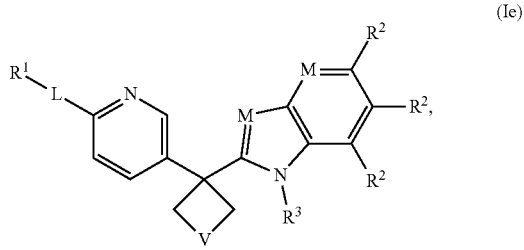

(Ie)

wherein:
L is selected from a bond, —NHC(O)— and —C(O)NH—;
each occurrence of M is independently selected from CR$^a$ and N; wherein R$^a$ is selected from H, halogen and C$_{1-6}$ alkyl;
V is selected from CR$^b$R$^b$, NR$^c$ and O; wherein each occurrence of R$^b$ is independently selected from H, —OH, halogen and C$_{1-6}$ alkyl; and R$^c$ is selected from H and C$_{1-6}$ alkyl;
R$^1$ is selected from C$_{1-6}$ alkyl, C$_{3-6}$ cycloalkyl, aryl and 5- or 6-membered heteroaryl; wherein the aryl and heteroaryl is optionally substituted with 1 to 3 substituents independently selected from halogen, —CN, —CF$_3$, —NH$_2$, C$_{1-6}$ alkyl and C$_{3-6}$ cycloalkyl;
each occurrence of R$^2$ is independently selected from H, —OH, halogen, —CN, C$_{1-6}$ alkyl, —O—C$_{1-6}$ alkyl and 5- or 6-membered heteroaryl; wherein each of the C$_{1-6}$ alkyl is optionally substituted with 1 to 3 substituents independently selected from —OH, —C(O)OH and halogen;
or alternatively, two adjacent R$^2$ groups together with the carbons to which they are attached form a 5- or 6-membered heterocyclic group which is optionally substituted with an oxo; and
R$^3$ is selected from H and C$_{1-6}$ alkyl optionally substituted with halogen or —OH.

In one embodiment of the compound of formula (Ie), or a pharmaceutically acceptable salt, solvate or hydrate thereof:
L is selected from —NHC(O)— and —C(O)NH—;
each occurrence of M is independently selected from CR$^a$ and N; wherein R$^a$ is selected from H, halogen and C$_{1-6}$ alkyl;
V is selected from CR$^b$R$^b$ and NR$^c$; wherein each occurrence of R$^b$ is independently selected from H, —OH, halogen and C$_{1-6}$ alkyl; and R$^c$ is selected from H and C$_{1-6}$ alkyl;
R$^1$ is selected from C$_{1-6}$ alkyl, C$_{3-6}$ cycloalkyl, aryl and 5- or 6-membered heteroaryl; wherein the aryl and heteroaryl is optionally substituted with 1 to 3 substituents independently selected from halogen, —CN, —CF$_3$, —NH$_2$, C$_{1-6}$ alkyl and C$_{3-6}$ cycloalkyl;
each occurrence of R$^2$ is independently selected from H, —OH, halogen, —CN, C$_{1-6}$ alkyl, —O—C$_{1-6}$ alkyl and 5- or 6-membered heteroaryl; wherein each of the C$_{1-6}$ alkyl is optionally substituted with 1 to 3 substituents independently selected from —OH and halogen;
or alternatively, two adjacent R$^2$ groups together with the carbons to which they are attached form a 5- or 6-membered heterocyclic group which is optionally substituted with an oxo; and
R$^3$ is selected from H and C$_{1-6}$ alkyl.

In one embodiment of the compound of formula (Ie), or a pharmaceutically acceptable salt, solvate or hydrate thereof:
each M is N;
V is CR$^b$R$^b$; wherein each occurrence of R$^b$ is independently selected from H, —OH, halogen and C$_{1-6}$ alkyl;
R$^1$ is selected from C$_{1-6}$ alkyl, C$_{3-6}$ cycloalkyl, aryl and 5- or 6-membered heteroaryl; wherein the aryl and heteroaryl is optionally substituted with 1 to 3 substituents independently selected from halogen, —CN, —CF$_3$, —NH$_2$, C$_{1-6}$ alkyl and C$_{3-6}$ cycloalkyl;
each occurrence of R$^2$ is independently selected from H, halogen, —CN and C$_{1-6}$ alkyl; wherein the C$_{1-6}$ alkyl is optionally substituted with 1 to 3 halogens; and
R$^3$ is H.

In one embodiment of the compound of formula (Ie), or a pharmaceutically acceptable salt, solvate or hydrate thereof:
one M is =CH— and the other M is =N—;
V is CR$^b$R$^b$; wherein each occurrence of R$^b$ is independently selected from H, —OH, halogen and C$_{1-6}$ alkyl; and R$^b$ is selected from H and C$_{1-6}$ alkyl;
R$^1$ is selected from C$_{1-6}$ alkyl, C$_{3-6}$ cycloalkyl, aryl and 5- or 6-membered heteroaryl; wherein the aryl and heteroaryl is optionally substituted with 1 to 3 substituents independently selected from halogen, —CN, —CF$_3$, —NH$_2$, C$_{1-6}$ alkyl and C$_{3-6}$ cycloalkyl;
each occurrence of R$^2$ is independently selected from H, halogen, —CN and C$_{1-6}$ alkyl; wherein the C$_{1-6}$ alkyl is optionally substituted with 1 to 3 halogens; and
R$^3$ is H.

In one embodiment, the compound of formula (Ie), or a pharmaceutically acceptable salt, solvate or hydrate thereof, is of formula (If):

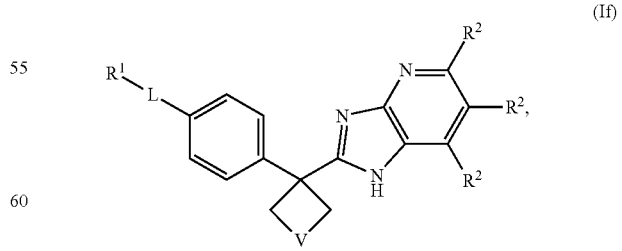

(If)

wherein:
L is selected from —NHC(O)— and —C(O)NH—;
V is selected from CR$^b$R$^b$ and NR$^c$; wherein each occurrence of R$^b$ is independently selected from H, —OH, halogen and C$_{1-6}$ alkyl; and R$^c$ is selected from H and C$_{1-6}$ alkyl;

$R^1$ is selected from $C_{1-6}$ alkyl, $C_{3-6}$ cycloalkyl, aryl and 5- or 6-membered heteroaryl; wherein the aryl and heteroaryl is optionally substituted with 1 to 3 substituents independently selected from halogen, —CN, —$CF_3$, —$NH_2$, $C_{1-6}$ alkyl and $C_{3-6}$ cycloalkyl; and each occurrence of $R^2$ is independently selected from H, —OH, halogen, —CN, $C_{1-6}$ alkyl, —O—$C_{1-6}$ alkyl and 5- or 6-membered heteroaryl; wherein each of the $C_{1-6}$ alkyl is optionally substituted with 1 to 3 substituents independently selected from —OH and halogen;

or alternatively, two adjacent $R^2$ groups together with the carbons to which they are attached form a 5- or 6-membered heterocyclic group which is optionally substituted with an oxo.

In one embodiment of the compound of formula (If), or a pharmaceutically acceptable salt, solvate or hydrate thereof:

L is selected from —NHC(O)— and —C(O)NH—;
V is —$CH_2$— or —$CF_2$—;
$R^1$ is selected from $C_{3-6}$ cycloalkyl, aryl and 5- or 6-membered heteroaryl; wherein the aryl and heteroaryl is optionally substituted with 1 to 3 substituents independently selected from halogen, —CN, —$CF_3$, $C_{1-6}$ alkyl and $C_{3-6}$ cycloalkyl; and each occurrence of $R^2$ is independently selected from H, —OH, halogen, —CN, $C_{1-6}$ alkyl, —O—$C_{1-6}$ alkyl and tetrazolyl; wherein each of the $C_{1-6}$ alkyl is optionally substituted with 1 to 3 substituents independently selected from —OH and halogen.

In one embodiment of the compound of formula (If), or a pharmaceutically acceptable salt, solvate or hydrate thereof:

L is selected from —NHC(O)— and —C(O)NH—;
V is —$CH_2$— or —$CF_2$—;
$R^1$ is selected from phenyl and pyridinyl; wherein the phenyl and the pyridinyl is optionally substituted with 1 to 3 substituents independently selected from halogen, —CN, —$CF_3$ and $C_{1-6}$ alkyl; and
each occurrence of $R^2$ is independently selected from H, halogen, —CN, $C_{1-6}$ alkyl and —O—$C_{1-6}$ alkyl; wherein each of the $C_{1-6}$ alkyl is optionally substituted with 1 to 3 substituents independently selected from —OH and halogen.

In one embodiment, the compound of formula (I), or a pharmaceutically acceptable salt, solvate or hydrate thereof, is of formula (Ig):

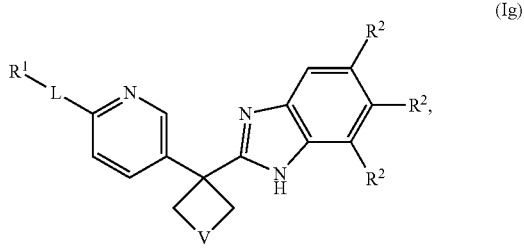

(Ig)

wherein:
L is selected from —NHC(O)— and —C(O)NH—;
V is selected from $CR^bR^b$ and $NR^c$; wherein each occurrence of $R^b$ is independently selected from H, —OH, halogen and $C_{1-6}$ alkyl; and $R^c$ is selected from H and $C_{1-6}$ alkyl;
$R^1$ is selected from $C_{1-6}$ alkyl, $C_{3-6}$ cycloalkyl, aryl and 5- or 6-membered heteroaryl; wherein the aryl and heteroaryl is optionally substituted with 1 to 3 substituents independently selected from halogen, —CN, —$CF_3$, —$NH_2$, $C_{1-6}$ alkyl and $C_{3-6}$ cycloalkyl; and each occurrence of $R^2$ is independently selected from H, —OH, halogen, —CN, $C_{1-6}$ alkyl, —O—$C_{1-6}$ alkyl and 5- or 6-membered heteroaryl; wherein each of the $C_{1-6}$ alkyl is optionally substituted with 1 to 3 substituents independently selected from —OH and halogen;

or alternatively, two adjacent $R^2$ groups together with the carbons to which they are attached form a 5- or 6-membered heterocyclic group which is optionally substituted with an oxo.

In one embodiment of the compound of formula (Ig), or a pharmaceutically acceptable salt, solvate or hydrate thereof:

L is selected from —NHC(O)— and —C(O)NH—;
V is —$CH_2$— or —$CF_2$—;
$R^1$ is selected from $C_{3-6}$ cycloalkyl, aryl and 5- or 6-membered heteroaryl; wherein the aryl and heteroaryl is optionally substituted with 1 to 3 substituents independently selected from halogen, —CN, —$CF_3$, $C_{1-6}$ alkyl and $C_{3-6}$ cycloalkyl; and each occurrence of $R^2$ is independently selected from H, —OH, halogen, —CN, $C_{1-6}$ alkyl, —O—$C_{1-6}$ alkyl and tetrazolyl; wherein each of the $C_{1-6}$ alkyl is optionally substituted with 1 to 3 substituents independently selected from —OH and halogen.

In one embodiment of the compound of formula (Ig), or a pharmaceutically acceptable salt, solvate or hydrate thereof:

L is selected from —NHC(O)— and —C(O)NH—;
V is —$CH_2$— or —$CF_2$—;
$R^1$ is selected from phenyl and pyridinyl; wherein the phenyl and the pyridinyl is optionally substituted with 1 to 3 substituents independently selected from halogen, —CN, —$CF_3$ and $C_{1-6}$ alkyl; and
each occurrence of $R^2$ is independently selected from H, halogen, —CN, $C_{1-6}$ alkyl and —O—$C_{1-6}$ alkyl; wherein each of the $C_{1-6}$ alkyl is optionally substituted with 1 to 3 substituents independently selected from —OH and halogen.

In one embodiment, a compound disclosed herein is selected from the group consisting of the compounds exemplified in Examples 1 to 48; or a pharmaceutically acceptable salt, solvate or hydrate thereof.

Also disclosed herein is a pharmaceutical composition comprising a compound disclosed herein and at least one pharmaceutically acceptable carrier.

Also disclosed herein is a method of inhibiting activity of indoleamine 2,3-dioxygenase (IDO) comprising contacting IDO with a compound disclosed herein, or a pharmaceutically acceptable salt, solvate or hydrate thereof.

Also disclosed herein is a method of inhibiting immunosuppression in a patient comprising administering to said patient an effective amount of a compound disclosed herein, or a pharmaceutically acceptable salt, solvate or hydrate thereof.

Also disclosed herein is a method of treating cancer, viral infection, depression, a neurodegenerative disorder, trauma, age-related cataracts, organ transplant rejection, or an autoimmune disease in a patient comprising administering to said patient an effective amount of a compound disclosed herein, or a pharmaceutically acceptable salt, solvate or hydrate thereof.

Also disclosed herein is a method of treating melanoma in a patient comprising administering to said patient an effective amount of a compound disclosed herein, or a pharmaceutically acceptable salt, solvate or hydrate thereof.

Further disclosed herein is a compound disclosed herein, or a pharmaceutically acceptable salt thereof, for use in therapy. In one embodiment, disclosed herein is the use of a compound disclosed herein, or a pharmaceutically acceptable salt, solvate or hydrate thereof, for the preparation of a medicament for use in therapy.

"Alkyl" refers to both branched- and straight-chain saturated aliphatic hydrocarbon groups of 1 to 18 carbon atoms, or more specifically, 1 to 12 carbon atoms. Examples of such groups include, but are not limited to, methyl (Me), ethyl (Et), n-propyl (Pr), n-butyl (Bu), n-pentyl, n-hexyl, and the isomers thereof such as isopropyl (i-Pr), isobutyl (i-Bu), sec-butyl (s-Bu), tert-butyl (t-Bu), isopentyl, and isohexyl. Alkyl groups may be optionally substituted with one or more substituents as defined herein. "$C_{1-6}$alkyl" refers to an alkyl group as defined herein having 1 to 6 carbon atoms.

"Aryl" refers to an aromatic monocyclic or multicyclic ring moiety comprising 6 to 14 ring carbon atoms, or more specifically, 6 to 10 ring carbon atoms. Monocyclic aryl rings include, but are not limited to, phenyl. Multicyclic rings include, but are not limited to, naphthyl and bicyclic rings wherein phenyl is fused to a $C_{5-7}$cycloalkyl or $C_{5-7}$cycloalkenyl ring. Aryl groups may be optionally substituted with one or more substituents as defined herein. Bonding can be through any of the carbon atoms of any ring.

"Halo" or "halogen" refers to fluoro, chloro, bromo or iodo, unless otherwise noted.

"Heterocycle" or "heterocyclyl" refers to a saturated, partially unsaturated or aromatic ring moiety having at least one ring heteroatom and at least one ring carbon atom. In one embodiment, the heteroatom is oxygen, sulfur, or nitrogen. A heterocycle containing more than one heteroatom may contain different heteroatoms. Heterocyclyl moieties include both monocyclic and multicyclic (e.g., bicyclic) ring moieties. Bicyclic ring moieties include fused, spirocycle and bridged bicyclic rings and may comprise one or more heteroatoms in either of the rings. The ring attached to the remainder of the molecule may or may not contain a heteroatom. Either ring of a bicyclic heterocycle may be saturated, partially unsaturated or aromatic. The heterocycle may be attached to the rest of the molecule via a ring carbon atom, a ring oxygen atom or a ring nitrogen atom. Non-limiting examples of heterocycles are described below.

In one embodiment, partially unsaturated and aromatic 4-7 membered monocyclic heterocyclyl moieties include, but are not limited to, 2,3-dihydro-1,4-dioxinyl, dihydropyranyl, dihydropyrazinyl, dihydropyridazinyl, dihydropyridinyl, dihydropyrimidinyl, dihydrotriazolyl, furanyl, imidazolyl, isothiazolyl, isoxazolyl, oxadiazolyl, oxazolyl, oxoimidazolidinyl, pyranyl, pyrazinyl, pyrazolyl, pyridazinyl, pyridinyl, pyrimidinyl, pyrrolyl, tetrahydropyrazinyl, tetrahydropyridazinyl, tetrahydropyridinyl, tetrahydropyrimidinyl, tetrazolyl, thiadiazolyl, thiazolyl, thienyl, thiophenyl, and triazolyl.

In one embodiment, a 5- or 6-membered heteroaryl is selected pyrazinyl, pyrazolyl, pyridazinyl, pyridinyl, pyrimidinyl, pyrrolyl, tetrazolyl, thiadiazolyl, thiazolyl, thienyl, thiophenyl, and triazolyl. In one embodiment, a 5- or 6-membered heteroaryl is pyridinyl. In one embodiment, a 5- or 6-membered heteroaryl is tetrazolyl.

Heterocyclic groups may be optionally substituted with one or more substituents as defined herein.

"Optionally substituted" refers to "unsubstituted or substituted," and therefore, the generic structural formulas described herein encompass compounds containing the specified optional substituent(s) as well as compounds that do not contain the optional substituent(s). Each substituent is independently defined each time it occurs within the generic structural formula definitions.

Polymorphism

A compound disclosed herein, including a salt, solvate or hydrate thereof, may exist in crystalline form, non-crystalline form, or a mixture thereof. A compound or a salt or solvate thereof may also exhibit polymorphism, i.e. the capacity of occurring in different crystalline forms. These different crystalline forms are typically known as "polymorphs". Polymorphs have the same chemical composition but differ in packing, geometrical arrangement, and other descriptive properties of crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, all of which may be used for identification. One of ordinary skill in the art will appreciate that different polymorphs may be produced, for example, by changing or adjusting the conditions used in crystallizing/recrystallizing a compound disclosed herein.

Optical Isomers—Diastereomers—Geometric Isomers—Tautomers

Included herein are various isomers of the compounds disclosed herein. The term "isomers" refers to compounds that have the same composition and molecular weight but differ in physical and/or chemical properties. The structural difference may be in constitution (geometric isomers) or in the ability to rotate the plane of polarized light (stereoisomers).

With regard to stereoisomers, a compound disclosed herein may have one or more asymmetric carbon atom and may occur as mixtures (such as a racemic mixture) or as individual enantiomers or diastereomers. All such isomeric forms are included herein, including mixtures thereof. If a compound disclosed herein contains a double bond, the substituent may be in the E or Z configuration. If a compound disclosed herein contains a disubstituted cycloalkyl, the cycloalkyl substituent may have a cis- or trans-configuration. All tautomeric forms are also intended to be included.

Any asymmetric atom (e.g., carbon) of a compound disclosed herein, can be present in racemic mixture or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

A compound disclosed herein, can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of the final compounds of the examples or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic compounds can also be resolved by chiral chromatography, e.g., high pressure liquid chromatography (HPLC) using a chiral adsorbent.

Some of the compounds described herein may exist with different points of attachment of hydrogen, referred to as tautomers. For example, compounds including carbonyl —$CH_2C(O)$— groups (keto forms) may undergo tautomerism to form hydroxyl —CH=C(OH)— groups (enol forms). Both keto and enol forms, individually as well as mixtures thereof, are included within the scope of the present invention.

Isotopic Variations Compounds disclosed herein, include unlabeled forms, as well as isotopically labeled forms. Isotopically labeled compounds have structures depicted by the formulas given herein except that one or more atoms are replaced by an atom having a selected atomic mass or mass number. Examples of isotopes that can be incorporated into compounds disclosed herein include isotopes of hydrogen, carbon, nitrogen, oxygen, phosphorous, sulfur, fluorine, iodine and chlorine, such as $^2H$ (i.e., Deuterium or "D"), $^3H$, $^{11}C$, $^{13}C$, $^{14}C$, $^{13}N$, $^{15}N$, $^{15}O$, $^{17}O$, $^{18}O$, $^{32}P$, $^{35}S$, $^{18}F$, $^{123}I$, $^{125}I$ and $^{36}Cl$. The invention includes various isotopically labeled compounds as defined herein, for example those into which radioactive isotopes, such as $^3H$ and $^{14}C$, or those into which non-radioactive isotopes, such as $^2H$ and $^{13}C$ are present. Such isotopically labeled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, substitution with positron emitting isotopes, such as $^{11}C$, $^{18}F$, $^{15}O$ and $^{13}N$, may be particularly desirable for PET or SPECT studies.

Isotopically-labeled compounds disclosed herein, can generally be prepared by conventional techniques known to those skilled in the art. Furthermore, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index.

Pharmaceutically Acceptable Salts

The term "pharmaceutically acceptable salt" refers to a salt prepared from a pharmaceutically acceptable non-toxic base or acid, including inorganic or organic base and inorganic or organic acid. Salts derived from inorganic bases include aluminum, ammonium, calcium, copper, ferric, ferrous, lithium, magnesium, manganic salts, manganous, potassium, sodium, zinc, and the like. Particular embodiments include ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When a compound disclosed herein is basic, a salt may be prepared from a pharmaceutically acceptable non-toxic acid, including an inorganic and organic acid. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, trifluoroacetic acid (TFA) and the like. Particular embodiments include the citric, hydrobromic, hydrochloric, maleic, phosphoric, sulfuric, fumaric, tartaric and trifluoroacetic acids.

METHODS OF USE

Compounds disclosed herein can inhibit activity of the enzyme indoleamine-2,3-dioxygenase (IDO). For example, the compounds disclosed herein can potentially be used to inhibit activity of IDO in cell or in an individual in need of modulation of the enzyme by administering an effective amount of a compound. Further disclosed herein are methods of inhibiting the degradation of tryptophan in a system containing cells expressing IDO such as a tissue, living organism, or cell culture. In some embodiments, the present invention provides methods of altering (e.g., increasing) extracellular tryptophan levels in a mammal by administering an effective amount of a compound or composition provided herein. Methods of measuring tryptophan levels and tryptophan degradation are routine in the art.

Also disclosed herein are methods of inhibiting immunosuppression such as IDO-mediated immunosuppression in a patient by administering to the patient an effective amount of a compound or composition recited herein. IDO-mediated immunosuppression has been associated with, for example, cancers, tumor growth, metastasis, viral infection, viral replication, etc.

Also disclosed herein are methods of treating diseases associated with activity or expression, including abnormal activity and/or overexpression, of IDO in an individual (e.g., patient) by administering to the individual in need of such treatment an effective amount or dose of a compound disclosed herein or a pharmaceutical composition thereof. Example diseases can include any disease, disorder or condition that may be directly or indirectly linked to expression or activity of the IDO enzyme, such as over expression or abnormal activity. An IDO-associated disease can also include any disease, disorder or condition that may be prevented, ameliorated, or cured by modulating enzyme activity. Examples of IDO-associated diseases include cancer, viral infection such as HIV and HCV, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, allergic inflammation, inflammatory bowel disease, psoriasis and systemic lupus erythematosusor. Example cancers potentially treatable by the methods herein include cancer of the colon, pancreas, breast, prostate, lung, brain, ovary, cervix, testes, renal, head and neck, lymphoma, leukemia, melanoma, and the like. The compounds of the invention may also be useful in the treatment of obesity and ischemia. As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the IDO enzyme with a compound disclosed herein includes the administration of a compound of the present invention to an individual or patient, such as a human, as well as, for example, introducing a compound of the invention into a sample containing a cellular or purified preparation containing the IDO enzyme.

A subject administered with a compound disclosed herein, or a pharmaceutically acceptable salt, solvate or hydrate thereof, is generally a mammal, such as a human being, male or female. A subject also refers to cows, sheep, goats, horses, dogs, cats, rabbits, rats, mice, fish, and birds. In one embodiment, the subject is a human.

As used herein, the terms "treatment" and "treating" refer to all processes wherein there may be a slowing, interrupting, arresting, controlling, or stopping of the progression of a disease or disorder that may be associated with IDO enzyme activity. The terms do not necessarily indicate a total elimination of all disease or disorder symptoms. The terms also include the potential prophylactic therapy of the mentioned conditions, particularly in a subject that is predisposed to such disease or disorder.

The terms "administration of" and or "administering a" compound should be understood to include providing a compound described herein, or a pharmaceutically acceptable salt, solvate or hydrate thereof, and compositions of the foregoing to a subject.

The amount of a compound administered to a subject is an amount sufficient to inhibit IDO enzyme activity in the subject. In an embodiment, the amount of a compound can be an "effective amount", wherein the subject compound is administered in an amount that will elicit a biological or medical response of a tissue, system, animal or human that is being sought by a researcher, veterinarian, medical doctor or other clinician. An effective amount does not necessarily include considerations of toxicity and safety related to the administration of a compound. It is recognized that one skilled in the art may affect physiological disorders associated with an IDO enzyme activity by treating a subject presently afflicted with the disorders, or by prophylactically treating a subject likely to be afflicted with the disorders, with an effective amount of a compound disclosed herein, or a pharmaceutically acceptable salt, solvate or hydrate thereof.

An effective amount of a compound will vary with the particular compound chosen (e.g. considering the potency, efficacy, and/or half-life of the compound); the route of administration chosen; the condition being treated; the severity of the condition being treated; the age, size, weight, and physical condition of the subject being treated; the medical history of the subject being treated; the duration of the treatment; the nature of a concurrent therapy; the desired therapeutic effect; and like factors and can be routinely determined by the skilled artisan.

The compounds disclosed herein may be administered by any suitable route including oral and parenteral administration. Parenteral administration is typically by injection or infusion and includes intravenous, intramuscular, and subcutaneous injection or infusion.

The compounds disclosed herein may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound disclosed herein depend on the pharmacokinetic properties of that compound, such as absorption, distribution and half-life which can be determined by a skilled artisan. In addition, suitable dosing regimens, including the duration such regimens are administered, for a compound disclosed herein depend on the disease or condition being treated, the severity of the disease or condition, the age and physical condition of the subject being treated, the medical history of the subject being treated, the nature of concurrent therapy, the desired therapeutic effect, and like factors within the knowledge and expertise of the skilled artisan. It will be further understood by such skilled artisans that suitable dosing regimens may require adjustment given an individual subject's response to the dosing regimen or over time as the individual subject needs change. Typical daily dosages may vary depending upon the particular route of administration chosen. Typical daily dosages for oral administration, to a human weighing approximately 70 kg would range from about 0.1 mg to about 2 grams, or more specifically, 0.1 mg to 500 mg, or even more specifically, 0.2 mg to 100 mg, of a compound disclosed herein.

One embodiment of the present invention provides for a method of treating a disease or disorder associated with IDO enzyme activity comprising administration of an effective amount of a compound disclosed herein to a subject in need of treatment thereof. In one embodiment, the disease or disorder associated with an IDO enzyme is a cell proliferation disorder.

In one embodiment, disclosed herein is the use of a compound disclosed herein in a therapy. The compound may be useful in a method of inhibiting IDO enzyme activity in a subject, such as a mammal in need of such inhibition, comprising administering an effective amount of the compound to the subject.

In one embodiment, disclosed herein is a pharmaceutical composition comprising a compound disclosed herein, or a pharmaceutically acceptable salt, solvate or hydrate thereof, for use in potential treatment of a disorder or disease related to IDO enzyme activity.

Compositions

The term "composition" as used herein is intended to encompass a dosage form comprising a specified compound in a specified amount, as well as any dosage form which results, directly or indirectly, from combination of a specified compound in a specified amount. Such term is intended to encompass a dosage form comprising a compound disclosed herein, or a pharmaceutically acceptable salt, solvate or hydrate thereof, and one or more pharmaceutically acceptable carriers or excipients. Accordingly, the compositions of the present invention encompass any composition made by admixing a compound of the present invention and one or more pharmaceutically acceptable carrier or excipients. By "pharmaceutically acceptable" it is meant the carriers or excipients are compatible with the compound disclosed herein and with other ingredients of the composition.

In one embodiment, disclosed herein is a composition comprising a compound disclosed herein, or a pharmaceutically acceptable salt, solvate or hydrate thereof, and one or more pharmaceutically acceptable carriers or excipients. The composition may be prepared and packaged in bulk form wherein an effective amount of a compound of the invention can be extracted and then given to a subject, such as with powders or syrups. Alternatively, the composition may be prepared and packaged in unit dosage form wherein each physically discrete unit contains an effective amount of a compound disclosed herein. When prepared in unit dosage form, the composition of the invention typically contains from about 0.1 mg to 2 grams, or more specifically, 0.1 mg to 500 mg, or even more specifically, 0.2 mg to 100 mg, of a compound disclosed herein, or a pharmaceutically acceptable salt, solvate or hydrate thereof.

A compound disclosed herein and a pharmaceutically acceptable carrier or excipient(s) will typically be formulated into a dosage form adapted for administration to a subject by a desired route of administration. For example, dosage forms include those adapted for (1) oral administration, such as tablets, capsules, caplets, pills, troches, powders, syrups, elixirs, suspensions, solutions, emulsions, sachets, and cachets; and (2) parenteral administration, such as sterile solutions, suspensions, and powders for reconstitution. Suitable pharmaceutically acceptable carriers or excipients will vary depending upon the particular dosage form chosen. In addition, suitable pharmaceutically acceptable carriers or excipients may be chosen for a particular function that they may serve in the composition. For example, certain pharmaceutically acceptable carriers or excipients may be chosen for their ability to facilitate the production of uniform dosage forms. Certain pharmaceutically acceptable carriers or excipients may be chosen for their ability to facilitate the production of stable dosage forms. Certain pharmaceutically acceptable carriers or excipients may be chosen for their ability to facilitate the carrying or transporting of a compound disclosed herein, once administered to the subject, from one organ or portion of the body to another organ or another portion of the body. Certain pharmaceutically acceptable carriers or excipients may be chosen for their ability to enhance patient compliance.

Suitable pharmaceutically acceptable excipients include the following types of excipients: diluents, lubricants, binders, disintegrants, fillers, glidants, granulating agents, coating agents, wetting agents, solvents, co-solvents, suspending agents, emulsifiers, sweeteners, flavoring agents, flavor masking agents, coloring agents, anti-caking agents, hemectants, chelating agents, plasticizers, viscosity increasing agents, antioxidants, preservatives, stabilizers, surfactants, and buffering agents.

A skilled artisan possesses the knowledge and skill in the art to select suitable pharmaceutically acceptable carriers and excipients in appropriate amounts for the use in the invention. In addition, there are a number of resources available to the skilled artisan, which describe pharmaceutically acceptable carriers and excipients and may be useful in selecting suitable pharmaceutically acceptable carriers and excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

The compositions of the invention are prepared using techniques and methods known to those skilled in the art. Some methods commonly used in the art are described in Remington's Pharmaceutical Sciences (Mack Publishing Company).

In one embodiment, the invention is directed to a solid oral dosage form such as a tablet or capsule comprising an effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives, (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch) gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as, for example, by coating or embedding particulate material in polymers, wax, or the like.

The compounds disclosed herein may also be coupled with soluble polymers as targetable drug carriers. Such polymers can include polyvinylpyrrolidone, pyrancopolymer, polyhydroxypropylmethacrylamidephenol, polyhydroxyethylaspartamidephenol, or polyethyleneoxidepolylysine substituted with palmitoyl residues. Furthermore, the compounds of the invention may be coupled to a class of biodegradable polymers useful in achieving controlled release of a drug, for example polylactic acid, polepsilon caprolactone, polyhydroxy butyric acid, polyorthoesters, polyacetals, polydihydropyrans, polycyanacrylates and cross-linked or amphipathic block copolymers of hydrogels.

In one embodiment, the invention is directed to a liquid oral dosage form. Oral liquids such as solution, syrups and elixirs can be prepared in dosage unit form so that a given quantity contains a predetermined amount of a compound disclosed herein. Syrups can be prepared by dissolving the compound of the invention in a suitably flavored aqueous solution; while elixirs are prepared through the use of a non-toxic alcoholic vehicle. Suspensions can be formulated by dispersing a compound disclosed herein in a non-toxic vehicle. Solubilizers and emulsifiers such as ethoxylated isostearyl alcohols and polyoxy ethylene sorbitol ethers, preservatives, flavor additives such as peppermint oil or other natural sweeteners or saccharin or other artificial sweeteners and the like can also be added.

In one embodiment, the invention is directed to compositions for parenteral administration. Compositions adapted for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Combinations

A compound disclosed herein may be used in combination with one or more other active agents, including but not limited to, other anti-cancer agents, that are used in the prevention, treatment, control, amelioration, or reduction of risk of a particular disease or condition (e.g., cell proliferation disorders). In one embodiment, a compound disclosed herein is combined with one or more other anti-cancer agents for use in the prevention, treatment, control amelioration, or reduction of risk of a particular disease or condition for which the compounds disclosed herein are useful. Such other active agents may be administered, by a route and in an amount commonly used therefor, contemporaneously or sequentially with a compound of the present invention.

When a compound disclosed herein is used contemporaneously with one or more other active agents, a composition containing such other active agents in addition to the compound disclosed herein is contemplated. Accordingly, the compositions of the present invention include those that also contain one or more other active ingredients, in addition to a compound disclosed herein. A compound disclosed herein may be administered either simultaneously with, or before or after, one or more other therapeutic agent(s). A compound disclosed herein may be administered separately, by the same or different route of administration, or together in the same pharmaceutical composition as the other agent(s).

Products provided as a combined preparation include a composition comprising a compound disclosed herein and one or more other active agent(s) together in the same pharmaceutical composition, or a compound disclosed herein, and one or more other therapeutic agent(s) in separate form, e.g. in the form of a kit.

The weight ratio of a compound disclosed herein to a second active agent may be varied and will depend upon the effective dose of each agent. Generally, an effective dose of each will be used. Thus, for example, when a compound disclosed herein is combined with another agent, the weight ratio of the compound disclosed herein to the other agent will generally range from about 1000:1 to about 1:1000, such as about 200:1 to about 1:200. Combinations of a compound disclosed herein and other active agents will generally also be within the aforementioned range, but in each case, an effective dose of each active agent should be used. In such combinations, the compound disclosed herein and other active agents may be administered separately or in conjunction. In addition, the administration of one element may be prior to, concurrent to, or subsequent to the administration of other agent(s).

In one embodiment, the invention provides a composition comprising a compound disclosed herein, and at least one other therapeutic agent as a combined preparation for simultaneous, separate or sequential use in therapy. In one embodiment, the therapy is the treatment of a disease or disorder associated with IDO enzyme activity.

In one embodiment, the invention provides a kit comprising two or more separate pharmaceutical compositions, at least one of which contains a compound disclosed herein. In one embodiment, the kit comprises means for separately retaining said compositions, such as a container, divided bottle, or divided foil packet. An example of such a kit is a blister pack, as typically used for the packaging of tablets, capsules and the like.

A kit disclosed herein may be used for administering different dosage forms, for example, oral and parenteral, for administering the separate compositions at different dosage intervals, or for titrating the separate compositions against one another. To assist with compliance, a kit of the invention typically comprises directions for administration.

Disclosed herein is a use of a compound disclosed herein, for treating a disease or disorder associated with IDO enzyme activity, wherein the medicament is prepared for administration with another active agent. The invention also provides the use of another active agent for treating a disease or disorder associated with an IDO enzyme, wherein the medicament is administered with a compound disclosed herein.

The invention also provides the use of a compound disclosed herein for treating a disease or disorder associated with IDO enzyme activity, wherein the patient has previously (e.g. within 24 hours) been treated with another active agent. The invention also provides the use of another therapeutic agent for treating a disease or disorder associated with IDO enzyme activity, wherein the patient has previously (e.g. within 24 hours) been treated with a compound disclosed herein. The second agent may be applied a week, several weeks, a month, or several months after the administration of a compound disclosed herein.

In one embodiment, the other active agent is selected from the group consisting of vascular endothelial growth factor (VEGF) receptor inhibitors, topoisomerase II inhibitors, smoothen inhibitors, alkylating agents, anti-tumor antibiotics, anti-metabolites, retinoids, immunomodulatory agents including but not limited to anti-cancer vaccines, CTLA-4, LAG-3 and PD-1 antagonists.

Examples of vascular endothelial growth factor (VEGF) receptor inhibitors include, but are not limited to, bevacizumab (sold under the trademark AVASTIN by Genentech/Roche), axitinib, (N-methyl-2-[[3-[([pound])-2-pyridin-2-ylethenyl]-1H-indazol-6-yl]sulfanyl]benzamide, also known as AG013736, and described in PCT Publication No. WO 01/002369), Brivanib Alaninate ((S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate, also known as BMS-582664), motesanib (N-(2,3-dihydro-3,3-dimethyl-1H-indol-6-yl)-2-[(4-pyridinyimethyj)amino]-3-pyfidinecarboxamide. and described in PCT Publication No. WO 02/068470), pasireotide (also known as SO 230, and described in PCT Publication No. WO 02/010192), and sorafenib (sold under the tradename NEXAVAR).

Examples of topoisomerase II inhibitors, include but are not limited to, etoposide (also known as VP-16 and Etoposide phosphate, sold under the tradenames TOPOSAR, VEPESID and ETOPOPHOS), and teniposide (also known as VM-26, sold under the tradename VUMON).

Examples of alkylating agents, include but are not limited to, 5-azacytidine (sold under the trade name VIDAZA), decitabine (sold under the trade name of DECOGEN), temozolomide (sold under the trade names TEMODAR and TEMODAL by Schering-Plough/Merck), dactinomycin (also known as actinomycin-D and sold under the tradename COSMEGEN), melphalan (also known as L-PAM, L-sarcolysin, and phenylalanine mustard, sold under the tradename ALKERAN), altretamine (also known as hexamethylmelamine (HMM), sold under the tradename HEXALEN), carmustine (sold under the tradename BCNU), bendamustine (sold under the tradename TREANDA), busulfan (sold under the tradenames BUSULFEX and MYLERAN), carboplatin (sold under the tradename PARAPLATIN), lomustine (also known as CCNU, sold under the tradename CeeNU), cisplatin (also known as CDDP, sold under the tradenames PLATINOL and PLATINOL-AQ), chlorambucil (sold under the tradename LEUKERAN), cyclophosphamide (sold under the tradenames CYTOXAN and NEOSAR), dacarbazine (also known as DTIC, DIC and imidazole carboxamide, sold under the tradename DTIC-DOME), altretamine (also known as hexamethylmelamine (HMM) sold under the tradename HEXALEN), ifosfamide (sold under the tradename IFEX), procarbazine (sold under the tradename MATULANE), mechlorethamine (also known as nitrogen mustard, mustine and mechloroethamine hydrochloride, sold under the tradename MUSTARGEN), streptozocin (sold under the tradename ZANOSAR), thiotepa (also known as thiophosphoamide, TESPA and TSPA, and sold under the tradename THIOPLEX).

Examples of anti-tumor antibiotics include, but are not limited to, doxorubicin (sold under the tradenames ADRIAMYCIN and RUBEX), bleomycin (sold under the tradename LENOXANE), daunorubicin (also known as dauorubicin hydrochloride, daunomycin, and rubidomycin hydrochloride, sold under the tradename CERUBIDINE), daunorubicin liposomal (daunorubicin citrate liposome, sold under the tradename DAUNOXOME), mitoxantrone (also known as DHAD, sold under the tradename NOVANTRONE), epirubicin (sold under the tradename ELLENCE), idarubicin (sold under the tradenames IDAMYCIN, IDAMYCIN PFS), and mitomycin C (sold under the tradename MUTAMYCIN).

Examples of anti-metabolites include, but are not limited to, claribine (2-chlorodeoxyadenosine, sold under the tradename LEUSTATIN), 5-fluorouracil (sold under the tradename ADRUCIL), 6-thioguanine (sold under the tradename PURINETHOL), pemetrexed (sold under the tradename ALIMTA), cytarabine (also known as arabinosylcytosine (Ara-C), sold under the tradename CYTOSAR-U), cytarabine liposomal (also known as Liposomal Ara-C, sold under the tradename DEPOCYT), decitabine (sold under the tradename DACOGEN), hydroxyurea (sold under the tradenames HYDREA, DROXIA and MYLOCEL), fludarabine (sold under the tradename FLUDARA), floxuridine (sold under the tradename FUDR), cladribine (also known as 2-chlorodeoxyadenosine (2-CdA) sold under the tradename LEUSTATIN), methotrexate (also known as amethopterin, methotrexate sodium (MTX), sold under the tradenames RHEUMATREX and TREXALL), and pentostatin (sold under the tradename NIPENT).

Examples of retinoids include, but are not limited to, alitretinoin (sold under the tradename PANRETIN), tretinoin (all-trans retinoic acid, also known as ATRA, sold under the tradename VESANOID), Isotretinoin (13-c/s-retinoic acid, sold under the tradenames ACCUTANE, AMNESTEEM, CLARAVIS, CLARUS, DECUTAN, ISOTANE, IZOTECH, ORATANE, ISOTRET, and SOTRET), and bexarotene (sold under the tradename TARGRETIN).

"PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. In any of the treatment method, medicaments and uses of the present invention in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in any of the treatment method, medicaments and uses of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv and Fv fragments. Examples of PD-1 antagonists include, but are not limited to, pembrolizumab (sold under the tradename KEYTRUDA) and nivolumab (sold under the tradename OPDIVO).

Examples of mAbs that bind to human PD-1, and useful in the treatment method, medicaments and uses of the present invention, are described in U.S. Pat. Nos. 7,488,802, 7,521,051, 8,008,449, 8,354,509, 8,168,757, WO2004/004771, WO2004/072286, WO2004/056875, and US2011/0271358.

Examples of mAbs that bind to human PD-L1, and useful in the treatment method, medicaments and uses of the present invention, are described in WO2013/019906, WO2010/077634 A1 and U.S. Pat. No. 8,383,796. Specific anti-human PD-L1 mAbs useful as the PD-1 antagonist in the treatment method, medicaments and uses of the present invention include MPDL3280A, BMS-936559, MEDI4736, MSB0010718C and an antibody which comprises the heavy chain and light chain variable regions of SEQ ID NO:24 and SEQ ID NO:21, respectively, of WO2013/019906.

Other PD-1 antagonists useful in any of the treatment method, medicaments and uses of the present invention include an immunoadhesin that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342. Specific fusion proteins useful as the PD-1 antagonist in the treatment method, medicaments and uses of the present invention include AMP-224 (also known as B7-DCIg), which is a PD-L2-FC fusion protein and binds to human PD-1.

Examples of other cytotoxic agents include, but are not limited to, arsenic trioxide (sold under the tradename TRISENOX), asparaginase (also known as L-asparaginase, and Erwinia L-asparaginase, sold under the tradenames ELSPAR and KIDROLASE).

EXPERIMENTAL

The following examples are intended to be illustrative only and not limiting in any way. Abbreviations used are those conventional in the art or the following.

ACN acetonitrile
aq. aqueous
° C. degree Celsius
BrettPhos Pd G3 [(2-di-cyclohexylphosphino-3,6-dimethoxy-2',4',6'-triisopropyl-1,1'-biphenyl)-2-(2'-amino-1,1'-biphenyl)]palladium(II) methanesulfonate
CPhos Pd G4 [(2-dicyclohexylphosphino-2',6'-bis(N,N-dimethylamino)-1,1'-biphenyl)-2-(2'-methylamino-1,1'-biphenyl)]palladium(II) methanesulfonate
DAST (Dimethylamino)sulfur trifluoride
DCM dichloromethane
DEA diethylamine
DIEA N,N-diisopropylethylamine
DMA dimethylamine
DME dimethoxyethane
DMF N,N-dimethylformamide
DMP 1,1,1-Tris(acetyloxy)-1,1-dihydro-1,2-benziodoxol-3-(1H)-one
DMSO dimethylsulfoxide dppf 1,1'-bis(diphenylphosphino)ferrocene
EDC N-(3-Dimethylaminopropyl)-N'-ethylcarbodiimide hydrochloride
EI electron ionization
EMEM Eagle's minimal essential medium
EtOAc ethyl acetate
EtOH ethanol
g gram
h hour(s)
HATU 1-[bis(dimethylamino)methylene]-1H-1,2,3-triazolo[4,5-b]pyridinium 3-oxid-hexafluorophosphate
HPLC high pressure liquid chromatography
kg kilogram
L liter
LC liquid chromatography
LCMS liquid chromatography and mass spectrometry
mCPBA 3-chloroperbenzoic acid
MeOH methanol
MS mass spectrometry
MTBE methyl tert-butyl ether
min minutes
mL milliliter(s)
m/z mass to charge ratio
nm nanometer
nM nanomolar
N normal
$Pd_2(dba)_3$ Tris(dibenzylideneacetone)dipalladium(0)
$Pd(dppf)_2Cl_2$ [1,1'-Bis(diphenylphosphino)ferrocene]dichloropalladium(II)
$PdCl_2(dtbpf)$ [1,1'-Bis(di-tert-butylphosphino)ferrocene]dichloropalladium(II)
PE petroleum ether
PS polystyrene
RPMI medium Roswell Park Memorial Institute medium
RT or rt room temperature
sat. saturated
t-BuOH tert-butanol
TEA triethyl amine
TFA trifluoroacetic acid
THF tetrahydrofuran
TLC thin layer chromatography
TTMSS tris(trimethylsilyl)silane
uL microliter(s)
Xantphos 4,5-bis(diphenylphosphino)-9,9-dimethylxanthene
XPhos Pd G2 Chloro(2-dicyclohexylphosphino-2',4',6'-triisopropyl-1,1'-biphenyl)[2-(2'-amino-1,1'-biphenyl)]palladium(II)

The following examples are intended to be illustrative only and not limiting in any way. Abbreviations used are those conventional in the art or the following.

General Synthetic Schemes

The compounds of formula (I) may be prepared by methods known in the art of organic synthesis as set forth in part by the following synthetic schemes and synthetic procedures and conditions for the illustrative intermediates and examples.

The compounds described herein may be made from commercially available starting materials or synthesized using known organic, inorganic, and/or enzymatic processes.

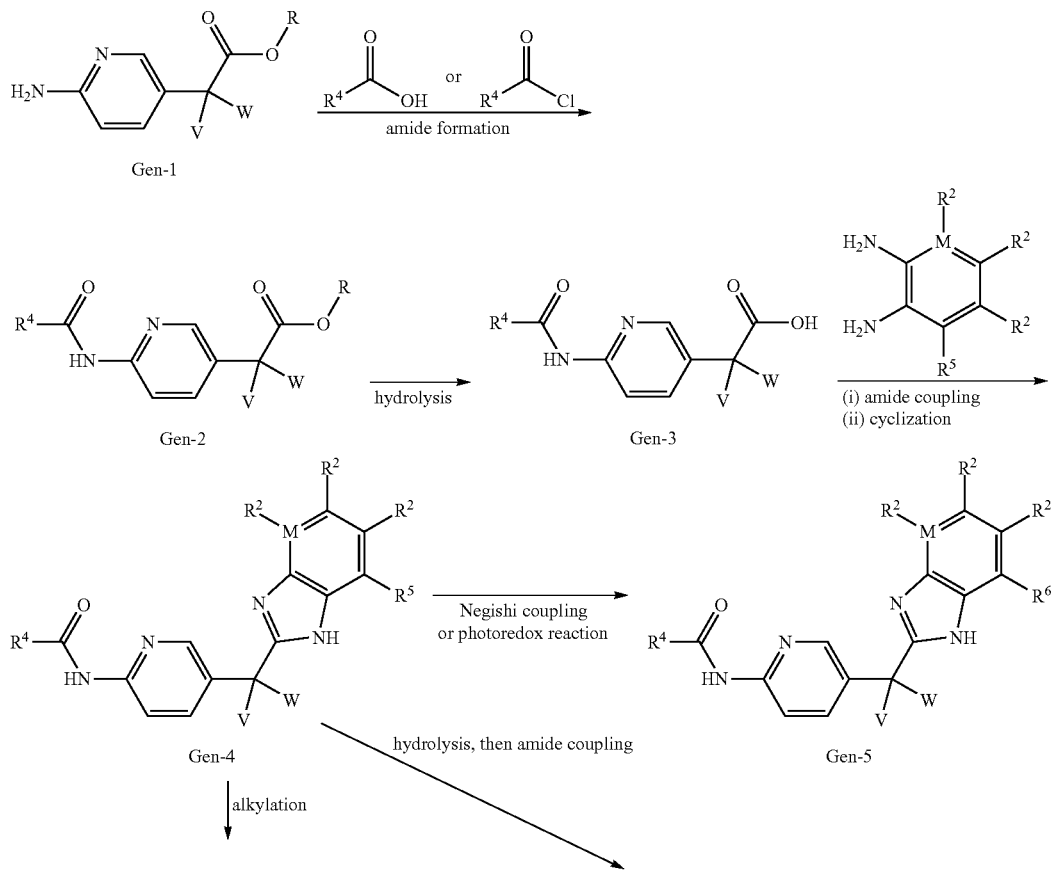

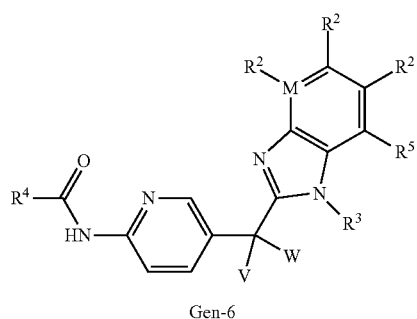

Gen-6

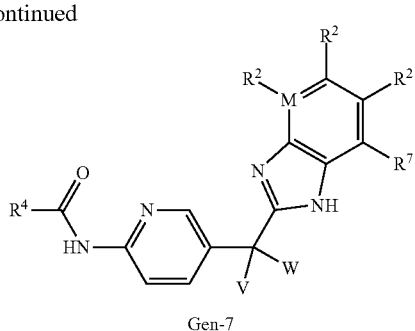

Gen-7

In general scheme 1, commercially available or synthetically prepared Gen-1 is coupled with a carboxylic acid or acid chloride to generate Gen-2, which is converted to Gen-3 through ester hydrolysis. Gen-3 is elaborated to Gen-4 by amide coupling with diverse phenyl or heterocyclic diamines, followed by dehydrative cyclization. In cases where $R^5$ is a halide, Gen-4 can be further converted to Gen-5 through a cross-coupling reaction (for example by Negishi coupling) where $R^6$ is a substituted alkyl group. In cases where $R^5$ is a ester, Gen-4 can be further converted to Gen-7 through a ester hydrolysis, then amide coupling. Gen-4 also can be converted to Gen-6 via an N-alkylation reaction, where $R^3$ is as described above. The representative compounds are described in more detail below.

In general scheme 2, commercially available or synthetically prepared Gen-8 is coupled with a carboxylic acid or acid chloride to generate Gen-9, which is converted to Gen-10 through ester hydrolysis. Gen-10 is elaborated to Gen-11 by amide coupling with diverse phenyl or heterocyclic diamines, followed by dehydrative cyclization.

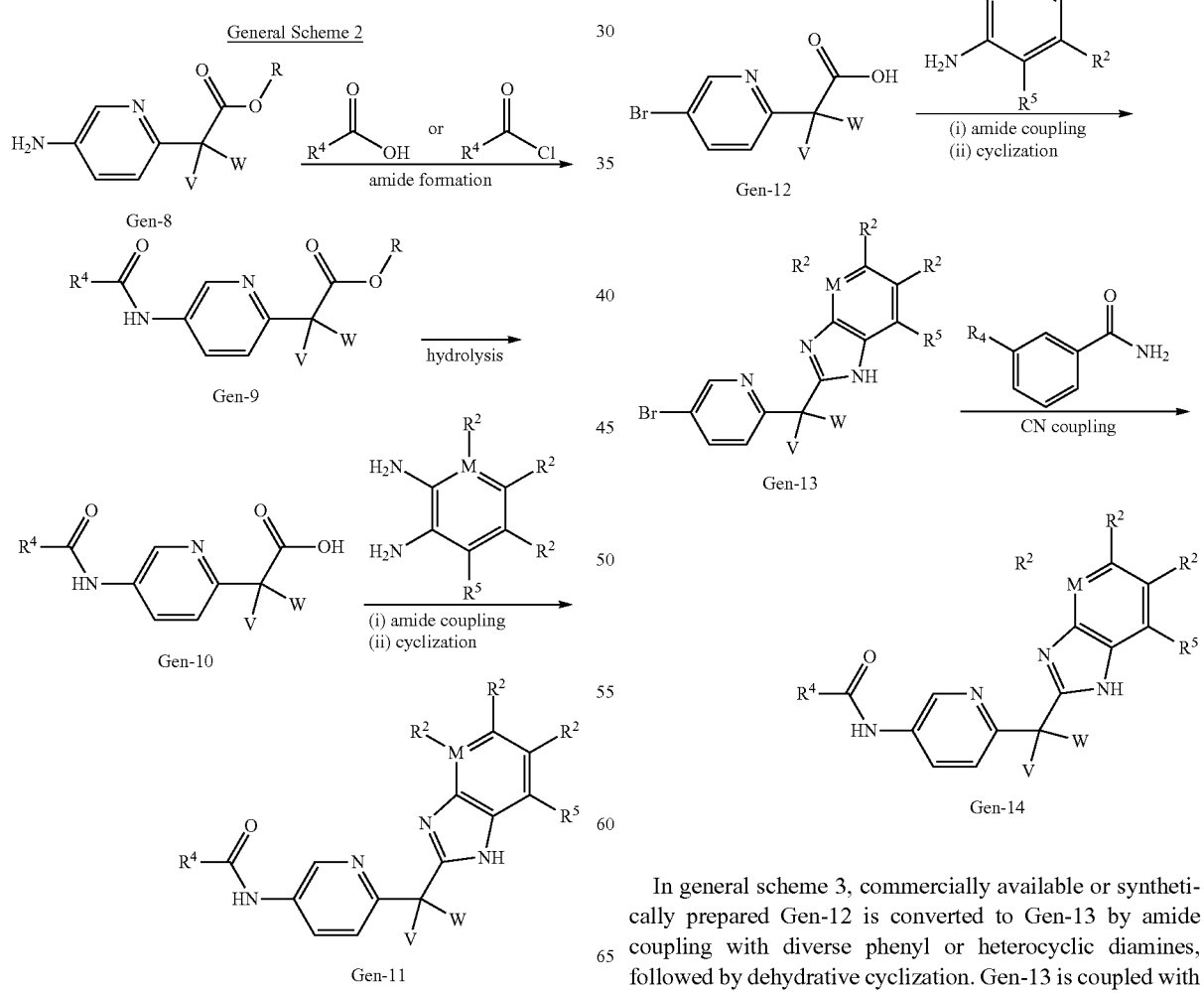

In general scheme 3, commercially available or synthetically prepared Gen-12 is converted to Gen-13 by amide coupling with diverse phenyl or heterocyclic diamines, followed by dehydrative cyclization. Gen-13 is coupled with aryl amide through CN coupling to generate Gen-14.

General Scheme 4

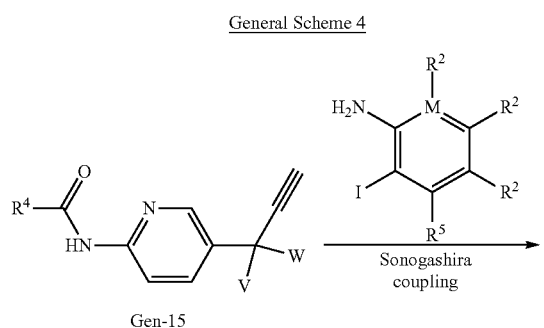

In general scheme 4, commercially available or synthetically prepared Gen-15 is converted to Gen-16 through Sonogashira coupling. Gen-16 is converted to Gen-17 by cyclization under basic condition.

General Scheme 5

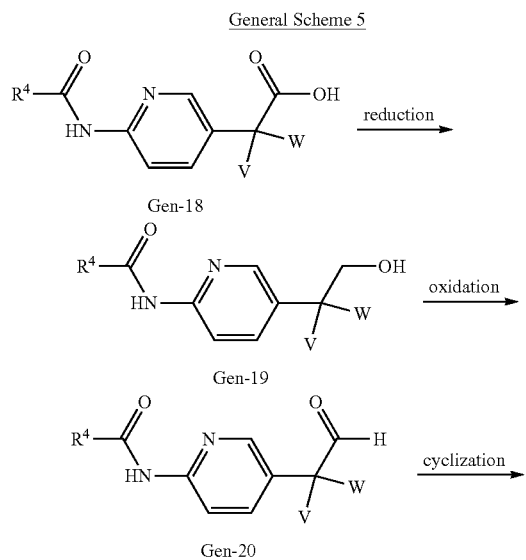

In general scheme 5, commercially available or synthetically prepared Gen-18 is reduced to Gen-19, followed by oxidation to generate Gen-20. Gen-20 is converted to Gen-21 through imine formation, followed by oxidative cyclization.

EXAMPLES

Example 1: N-(5-(1-(6-bromo-1H-imidazo[4,5-b]pyridin-2-yl)cyclobutyl)pyridin-2-yl)-3-chlorobenzamide

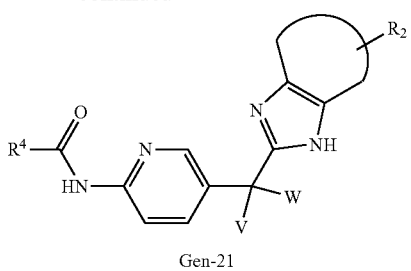

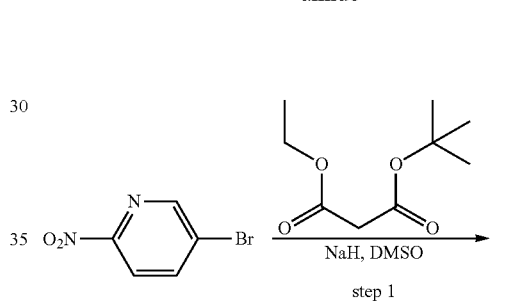

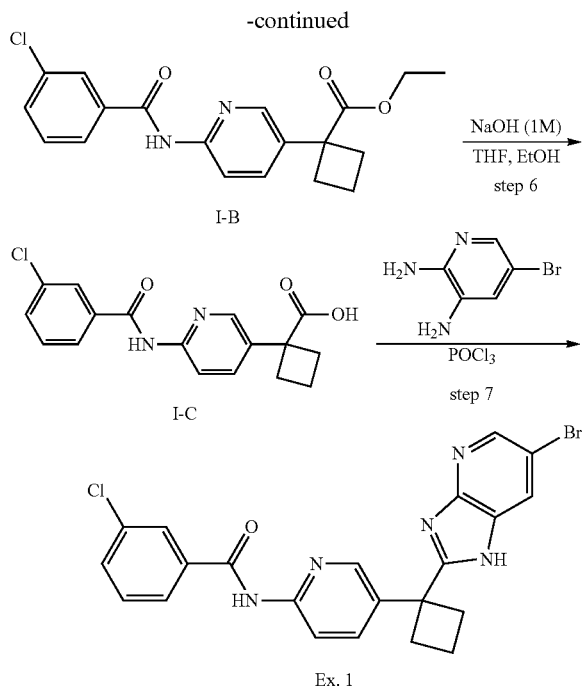

Ex. 1

Step 1: 1-Tert-butyl 3-ethyl 2-(6-nitropyridin-3-yl) malonate

To a stirred solution of tert-butyl ethyl malonate (111 g, 591 mmol) in DMSO (150 mL) was added NaH (23.6 g, 591 mmol) (60% in oil) in portions at 15° C. After the addition was finished, the reaction was stirred at RT for 0.5 h before 5-bromo-2-nitropyridine (60.0 g, 296 mmol) was added. The reaction mixture was stirred at 80° C. for 3 h, and then cooled to RT. The reaction was quenched with sat. NH$_4$Cl (500 mL), diluted with water (1000 mL), then extracted with EtOAc (800 mL×2). The combined organic layers were washed with brine (500 mL), dried over Na$_2$SO$_4$, filtered, and concentrated in vacuo. The residue was purified by column chromatography on silica gel (Petroleum ether/EtOAc=10:1 to 5:1) to give the title compound. MS (EI) m/z 311 [M+H]$^+$.

Step 2: Ethyl 2-(6-nitropyridin-3-yl)acetate

A solution of 1-tert-butyl 3-ethyl 2-(6-nitropyridin-3-yl) malonate (87.0 g, 280 mmol) in TFA (150 mL) was stirred at RT for 2 h. The reaction mixture was concentrated and diluted with EtOAc (1000 mL). The solution was washed with sat. NaHCO$_3$ (500 mL), water (1000 mL), and brine (300 mL), dried over anhydrous Na$_2$SO$_4$, filtered, and concentrated in vacuo. The residue was purified by column chromatography on silica gel (petroleum ether/EtOAc=5/1 to 2/1) to give the title compound. MS (EI) m/z 211 [M+H]$^+$.

Step 3: Ethyl 1-(6-nitropyridin-3-yl)cyclobutane-1-carboxylate

To a solution of ethyl 2-(6-nitropyridin-3-yl)acetate (33.0 g, 157 mmol) in DMF (150 mL) was added NaH (13.2 g, 330 mmol) (60% in oil) at 0° C. The reaction was allowed to warm to RT and stirred for 15 min. The mixture was cooled to 0° C. again before 1,3-diiodopropane (37.3 mL, 325 mmol) was added. The resulting mixture was stirred at 0° C. for 30 min, then warmed to RT and stirred for 1 h. The mixture was quenched with sat. NH$_4$Cl (500 mL), diluted with water (500 mL), then extracted with EtOAc (500 mL×3). The combined organic layers were washed with brine (200 mL), dried over Na$_2$SO$_4$, filtered, and concentrated in vacuo. The residue was purified by column chromatography on silica gel (Petroleum ether/EtOAc=30/1 to 20/1) to give the title compound. MS (EI) m/z 251 [M+H]$^+$.

Step 4: Ethyl 1-(6-aminopyridin-3-yl)cyclobutane-1-carboxylate (I-A)

To a stirred solution of ethyl 1-(6-nitropyridin-3-yl)cyclobutane-1-carboxylate (5.0 g, 21 mmol) in EtOH (80 mL) and water (8 mL) were added iron (5.96 g, 107 mmol) and ammonium chloride (11.4 g, 213 mmol). After the addition was finished, the reaction was stirred at 90° C. for 2 h. The mixture was filtered through a pad of Celite, and the filtrate was concentrated in vacuo to afford a crude product, which was purified by column chromatography on silica gel (DCM/EtOH=20/1) to afford the title compound (I-A). MS (EI) m/z 221 [M+H]$^+$.

Step 5: Ethyl 1-(6-(3-chlorobenzamido)pyridin-3-yl)cyclobutane-1-carboxylate (I-B)

To a vial were added 3-chlorobenzoic acid (2.18 g, 13.9 mmol), I-A (3.0 g, 14 mmol), HATU (5.70 g, 14.9 mmol), DMF (100 mL) and DIEA (8.0 ml, 46 mmol). The mixture was stirred at RT for 19 h, after which the solvent was removed in vacuo. The residue was purified by column chromatography on silica gel (EtOAc in hexane, 0-20% gradient) to afford the title compound (I-B). MS (EI) m/z 359 [M+H]$^+$.

Step 6: 1-(6-(3-Chlorobenzamido)pyridin-3-yl)cyclobutane-1-carboxylic acid (I-C)

To the vial containing I-B (3.08 g, 8.58 mmol) were added ethanol (10 mL), THF (30 mL) and NaOH (35 mL, 35 mmol, 1M). The mixture was stirred at RT for 17 h, after which the organic solvent was removed in vacuo. To the residue was added HCl (1 M) to adjust the pH to ~4. The resulting precipitate was collected via filtration to afford 1-(6-(3-chlorobenzamido)pyridin-3-yl)cyclobutane-1-carboxylic acid (I-C). MS (EI) m/z 331 [M+H]$^+$.

Step 7: N-(5-(1-(6-bromo-1H-imidazo[4,5-b]pyridin-2-yl)cyclobutyl)pyridin-2-yl)-3-chlorobenzamide To a stirred solution of I-C (300 mg, 0.907 mmol) in POCl$_3$ (3252 µL, 34.90 mmol) was added 5-bromopyridine-2,3-diamine (171 mg, 0.907 mmol) at 20° C. After the addition was finished, the reaction was stirred at 130° C. for 5 h. The reaction mixture was purified by reversed phase HPLC, eluting with water (0.1% TFA)-CH$_3$CN to afford the title compound. $^1$H NMR (400 MHz, CD$_3$OD) δ 8.47 (d, J=2.1 Hz, 1H), 8.43 (s, 1H), 8.15 (d, J=2.1 Hz, 1H), 8.10-8.14 (m, 1H), 8.05-8.09 (m, 1H), 8.02 (t, J=1.8 Hz, 1H), 7.93 (dt, J=7.8, 1.3 Hz, 1H), 7.65 (ddd, J=8.0, 2.0, 1.0 Hz, 1H), 7.52-7.57 (m, 1H), 3.13 (dq, J=8.7, 6.1 Hz, 2H), 2.85-2.96 (m, 2H), 2.08-2.29 (m, 2H); MS (EI) m/z 482 [M+H]$^+$.

Example 2: 3-Chloro-N-(5-(1-(6-cyano-1H-imidazo[4,5-b]pyridin-2-yl)cyclobutyl)pyridin-2-yl)benzamide

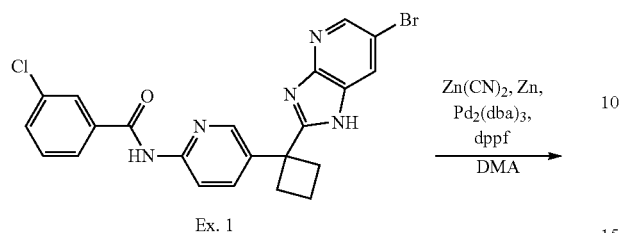

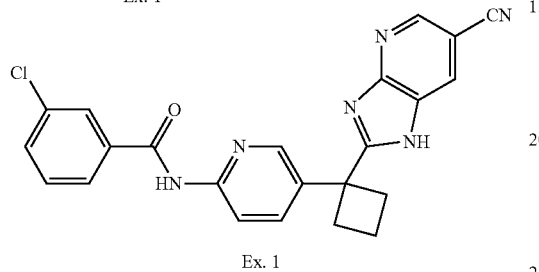

To a solution of compound Ex. 1 (30 mg, 0.062 mmol) in DMA (2 mL) were added zinc (1.0 mg, 0.015 mmol), Zn(CN)$_2$ (15 mg, 0.13 mmol), dppf (2.0 mg, 3.6 µmol) and Pd$_2$(dba)$_3$ (1.0 mg, 1.1 µmol) at RT. After the addition was finished, the reaction mixture was irradiated in the microwave at 150° C. for 0.5 h. Then purified by reversed phase HPLC, eluting with ACN/water (0.1% TFA), followed by lyophilization to afford the title compound (Ex. 2). $^1$H NMR (400 MHz, CD$_3$OD) δ 8.68 (d, J=1.8 Hz, 1H), 8.43 (s, 1H), 8.33 (d, J=1.8 Hz, 1H), 8.16-8.09 (m, 1H), 8.07-8.02 (m, 2H), 7.94 (d, J=8.3 Hz, 1H), 7.67 (d, J=8.3 Hz, 1H), 7.60-7.52 (m, 1H), 3.22-3.10 (m, 2H), 2.99-2.82 (m, 2H), 2.28-2.09 (m, 2H); MS (EI) m/z 429 [M+H]$^+$.

Example 3: N-(5-(1-(1H-benzo[d]imidazol-2-yl)cyclobutyl)pyridin-2-yl)-3-chlorobenzamide

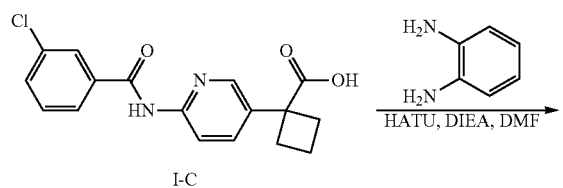

To a vial were added I-C (25 mg, 0.076 mmol), benzene-1,2-diamine (14 mg, 0.13 mmol), HATU (55 mg, 0.14 mmol), DMF (400 µL) and DIEA (40 µL, 0.23 mmol). The mixture was stirred at 100° C. for 20 h. The mixture was filtered and purified by reversed phase HPLC, eluting with water (0.1% TFA)-ACN to afford the title compound as a TFA salt (Ex. 3). $^1$H NMR (600 MHz, DMSO-d$_6$) δ 11.06 (s, 1H), 8.49 (s, 1H), 8.17 (d, J=8.7 Hz, 1H), 8.02 (s, 1H), 7.91 (t, J=7.0 Hz, 2H), 7.73-7.65 (m, 2H), 7.63 (d, J=7.8 Hz, 1H), 7.51 (t, J=7.9 Hz, 1H), 7.47-7.40 (s, 2H), 3.06 (q, J=10.0, 8.6 Hz, 2H), 2.85 (q, J=8.7 Hz, 2H), 2.21-1.92 (m, 2H); MS (EI) m/z 403 [M+H]$^+$.

Example 4: N-(5-(1-(6-cyano-1H-imidazo[4,5-b]pyridin-2-yl)cyclobutyl)pyridin-2-yl)-5-fluoronicotinamide

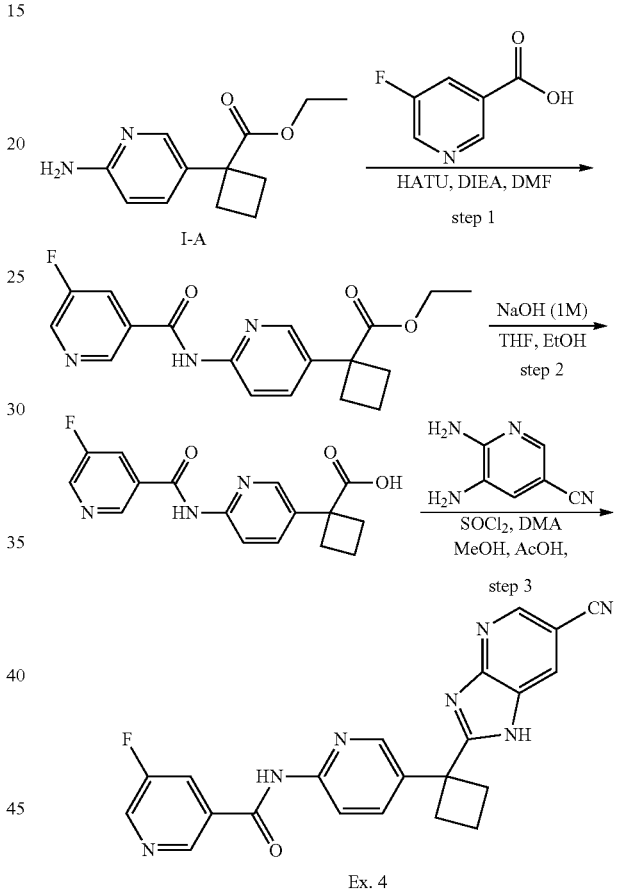

Step 1: Ethyl 1-(6-(5-fluoronicotinamido)pyridin-3-yl)cyclobutane-1-carboxylate To a vial were added 5-fluoronicotinic acid (109 mg, 0.775 mmol), I-A (205 mg, 0.930 mmol), HATU (354 mg, 0.930 mmol), DMF (5 mL) and DIEA (500 µL, 2.86 mmol). The mixture was stirred at RT for 19 h. The solvent was removed in vacuo, and the residue was purified by column chromatography on silica gel (EtOAc in hexane, 0-50% gradient) to afford the title compound. MS (EI) m/z 344 [M+H]$^+$.

Step 2: 1-(6-(5-Fluoronicotinamido)pyridin-3-yl)cyclobutane-1-carboxylic acid To a vial containing ethyl 1-(6-(5-fluoronicotinamido)pyridin-3-yl)cyclobutanecarboxylate (201 mg, 0.585 mmol), were added THF (3 mL), NaOH (2 mL, 2 mmol, 1M) and MeOH (1 mL). The mixture was stirred at RT for 18 h. The organic solvent was removed in vacuo, and the aqueous residue was adjusted to pH-4 with HCl (1 M) solution. The aqueous layer was extracted with EtOAc (15 ml×3). The combined organic layers were dried over Na$_2$SO$_4$, filtered, concentrated to afford the title compound. MS (EI) m/z 316 [M+H]$^+$.

Step 3: N-(5-(1-(6-cyano-1H-imidazo[4,5-b]pyridin-2-yl)cyclobutyl)pyridin-2-yl)-5-fluoronicotinamide To a vial were added 1-(6-(5-fluoronicotinamido)pyridin-3-yl)cyclobutanecarboxylic acid (100 mg, 0.317 mmol) and DMA (0.5 mL). To this solution at −5° C. was added thionyl chloride (0.025 mL, 0.35 mmol). After stirring for 1 h, a solution of 5,6-diaminonicotinonitrile (44.7 mg, 0.333 mmol) in DMA (1 mL) was added dropwise. Upon complete addition, the mixture was warmed to 20° C. and stirred for 18 h. The solvent was removed in vacuo and the residue was partitioned between sat. NaHCO$_3$ and EtOAc. The organic phase was washed with brine, dried over Na$_2$SO$_4$, filtered, and concentrated to afford crude N-(5-(1-((2-amino-5-cyanopyridin-3-yl)carbamoyl)cyclobutyl)pyridin-2-yl)-5-fluoronicotinamide, which was dissolved into MeOH (1 mL) and acetic acid (0.25 mL).

The mixture was heated at 130° C. for 18 h, then filtered and purified by reversed phase HPLC, eluting with water (0.1% TFA)-ACN to afford the title compound as a TFA salt (Ex. 4). $^1$H NMR (600 MHz, DMSO-d$_6$) δ 11.19 (s, 1H), 8.95 (s, 1H), 8.74 (s, 1H), 8.66 (s, 1H), 8.47 (s, 1H), 8.38 (s, 1H), 8.22 (d, J=9.2 Hz, 1H), 8.11 (d, J=8.6 Hz, 1H), 7.82 (d, J=7.2 Hz, 1H), 3.09-2.95 (m, 2H), 2.74 (q, J=8.8 Hz, 2H), 2.10-1.88 (m, 2H). MS (EI) m/z 414 [M+H]$^+$.

Example 5: 3-Cyano-N-(5-(1-(5-cyano-1H-benzo[d]imidazol-2-yl)cyclobutyl)pyridin-2-yl)benzamide

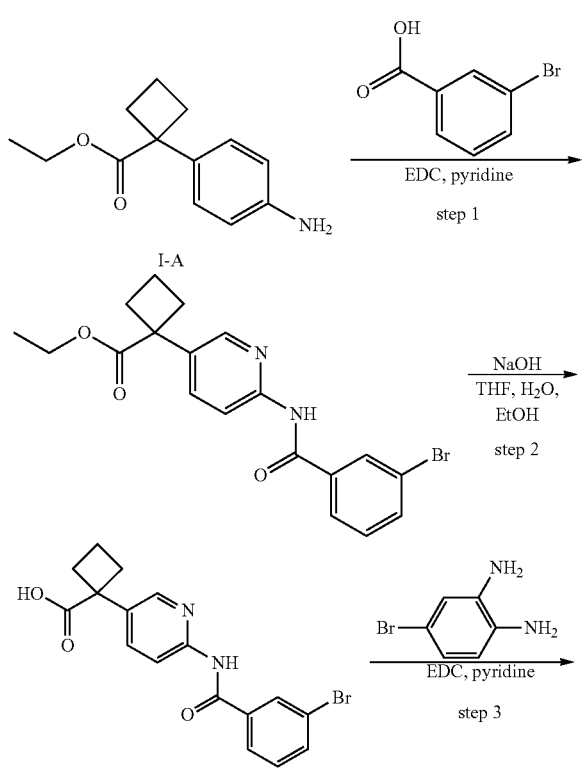

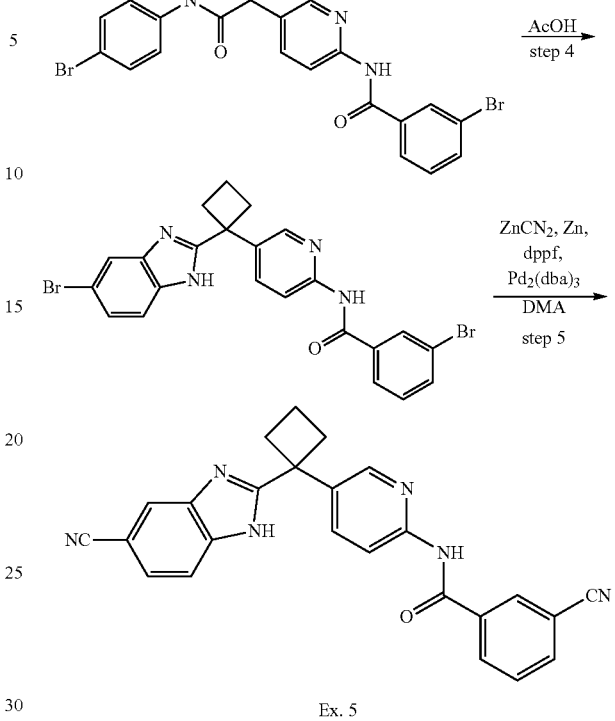

Ex. 5

Step 1: Ethyl 1-(6-(3-bromobenzamido)pyridin-3-yl)cyclobutane-1-carboxylate

To a solution of I-A (3.0 g, 13 mmol) in pyridine (50 mL) was added 3-bromobenzoic acid (3.29 g, 16.3 mmol) and EDC (7.83 g, 40.9 mmol) at RT. The mixture was stirred at RT for 2 h. The reaction was diluted with water (200 mL), extracted with ethyl acetate. The combined organic layers were washed with brine, dried over Na$_2$SO$_4$, filtered and concentrated in vacuo to afford a residue, which was purified by column chromatography on silica gel (EtOAc in petroleum ether: 0-50% gradient) to give the title compound. MS (EI) m/z 403 [M+H]$^+$.

Step 2: 1-(6-(3-Bromobenzamido)pyridin-3-yl)cyclobutane-1-carboxylic acid

To a solution of ethyl 1-(6-(3-bromobenzamido)pyridin-3-yl)cyclobutanecarboxylate (2.00 g, 4.96 mmol) in THF (20 mL), water (5 mL) and EtOH (2 mL) were added 2M NaOH (5.0 mL, 10 mmol) at RT. The reaction was stirred at RT for 16 h. The reaction was diluted with water (200 mL), adjusted to pH-2 with 3M HCl, and extracted with ethyl acetate. The combined organic layers were washed with brine, dried over Na$_2$SO$_4$, filtered and concentrated in vacuo to afford the title compound, which was used directly in next step without further purification. MS (EI) m/z 375 [M+H]$^+$.

Step 3: N-(5-(1-((2-amino-4-bromophenyl)carbamoyl)cyclobutyl)pyridin-2-yl)-3-bromobenzamide To a stirred solution of 1-(6-(3-bromobenzamido)pyridin-3-yl)cyclobutanecarboxylic acid (465 mg, 1.24 mmol) in pyridine (8 mL) was added EDC (713 mg, 3.72 mmol) and 4-bromobenzene-1,2-diamine (278 mg, 1.49 mmol) at RT. The mixture was stirred at RT for 2 h. The solvent was concentrated in vacuo. The residue was diluted with water and extracted with ethyl acetate. The combined organic layers were washed with brine, dried over Na$_2$SO$_4$, filtered and concentrated in vacuo to afford a residue, which was purified by prep-TLC (petroleum ether:ethyl acetate=1:1) to give the title compound. MS (EI) m/z 543 [M+H]$^+$.

Step 4: 3-Bromo-N-(5-(1-(5-bromo-1H-benzo[d]imidazol-2-yl)cyclobutyl)pyridin-2-yl)benzamide A solution of N-(5-(1-((2-amino-4-bromophenyl)carbamoyl)cyclobutyl)pyridin-2-yl)-3-bromobenzamide (340 mg, 0.625 mmol) in AcOH (10 mL) was stirred at 120° C. for 16 h. The reaction mixture was concentrated in vacuo. The residue was diluted with NaHCO$_3$ (sat.) and extracted with ethyl acetate. The combined organic layers were washed with brine, dried over Na$_2$SO$_4$, filtered and concentrated in vacuo to afford a residue, which was purified by prep-TLC (petroleum ether:ethyl acetate=1:1) to give the title compound. MS (EI) m/z 525 [M+H]$^+$.

Step 5: 3-Cyano-N-(5-(1-(5-cyano-1H-benzo[d]imidazol-2-yl)cyclobutyl)pyridin-2-yl)benzamide (Ex. 5)

To a solution of 3-bromo-N-(5-(1-(5-bromo-1H-benzo[d]imidazol-2-yl)cyclobutyl)pyridin-2-yl)benzamide (120 mg, 0.228 mmol), dppf (16 mg, 0.029 mmol) and zinc (6.0 mg, 0.092 mmol), in DMA (1.5 mL) were added dicyanozinc (107 mg, 0.912 mmol) and Pd$_2$(dba)$_3$ (9.0 mg, 9.8 µmol) at RT. After the addition was finished, the reaction mixture was irradiated at 150° C. for 1 h. The reaction was cooled to RT, poured into water and extracted with ethyl acetate. The combined organic layers were washed with brine, dried over Na$_2$SO$_4$, filtered and concentrated in vacuo to afford a residue, which was purified by reversed phase HPLC, eluting with water (0.1% TFA)-ACN to afford the title compound as a TFA salt (Ex. 5). $^1$H NMR (400 MHz, CD$_3$OD) δ 8.49 (d, J=2.0 Hz, 1H), 8.32 (s, 1H), 8.25-8.24 (m, 1H), 8.20-8.17 (m, 1H), 8.11-8.10 (m, 1H), 8.06 (s, 1H), 7.96-7.93 (m, 1H), 7.80-7.78 (m, 1H), 7.72-7.71 (m, 2H), 3.16-3.11 (m, 2H), 3.01-2.97 (m, 2H), 2.26-2.18 (m, 2H); MS (EI) m/z 419 [M+H]$^+$.

Example 6: 3-Chloro-N-(5-(1-(5-cyano-1H-pyrrolo[2,3-b]pyridin-2-yl)cyclobutyl)pyridin-2-yl)benzamide

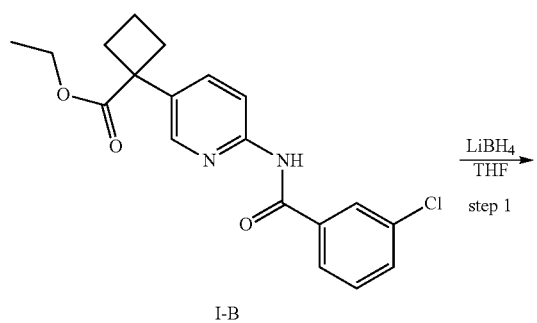

I-B

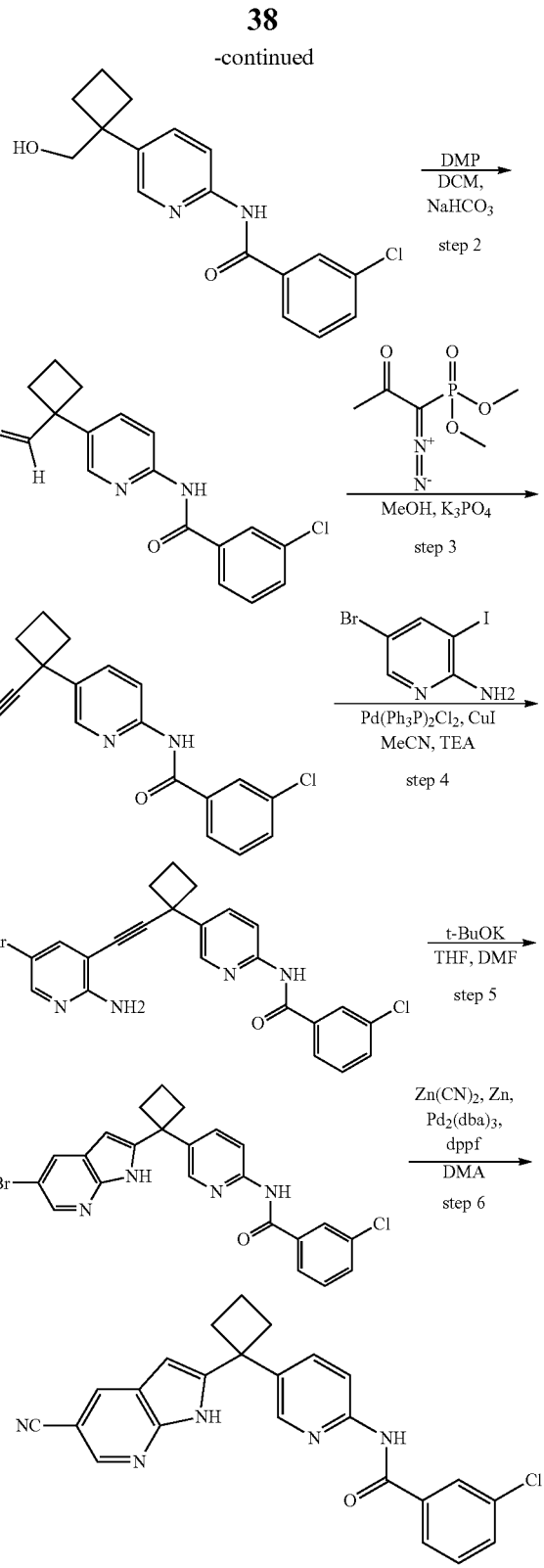

Ex. 6

Step 1: 3-Chloro-N-(5-(1-(hydroxymethyl)cyclobutyl)pyridin-2-yl)benzamide

To a solution of I-B (350 mg, 0.975 mmol) in THF (5 mL) was added LiBH$_4$ (43 mg, 2.0 mmol) at RT. The mixture was stirred at RT for 16 h. The reaction was diluted with water, extracted with ethyl acetate. The combined organic layers were washed with brine, dried over Na$_2$SO$_4$, filtered and concentrated in vacuo to afford a residue, which was purified by column chromatography on silica gel (EtOAc in petroleum ether: 0-50% gradient) to give the title compound. MS (EI) m/z 317 [M+H]$^+$.

Step 2: 3-Chloro-N-(5-(1-formylcyclobutyl)pyridin-2-yl)benzamide

To a stirred solution of 3-chloro-N-(5-(1-(hydroxymethyl)cyclobutyl)pyridin-2-yl)benzamide (130 mg, 0.410 mmol) in DCM (2 mL) was added NaHCO$_3$ (345 mg, 4.10 mmol) at RT. After stirring for 5 min, DMP (261 mg, 0.616 mmol) was added. After the addition was finished, the reaction was stirred at RT for 24 h. The reaction was diluted with water, extracted with ethyl acetate. The combined organic layers were washed with brine, dried over Na$_2$SO$_4$, filtered and concentrated in vacuo to afford a residue, which was purified by pre-TLC (petroleum ether:ethyl acetate=5:1) to give the title compound. MS (EI) m/z 315 [M+H]$^+$.

Step 3: 3-Chloro-N-(5-(1-ethynylcyclobutyl)pyridin-2-yl)benzamide

To a solution of 3-chloro-N-(5-(1-formylcyclobutyl)pyridin-2-yl)benzamide (150 mg, 0.477 mmol) in MeOH (3 mL) were added K$_2$CO$_3$ (132 mg, 0.953 mmol) and dimethyl (1-diazo-2-oxopropyl)phosphonate (137 mg, 0.715 mmol) at RT. The mixture was stirred at RT for 16 h. The reaction was diluted with water, extracted with ethyl acetate. The combined organic layers were washed with brine, dried over Na$_2$SO$_4$, filtered and concentrated in vacuo to afford a residue, which was purified by pre-TLC (petroleum ether:ethyl acetate=5:1) to give the title compound. MS (EI) m/z 311 [M+H]$^+$.

Step 4: N-(5-(1-((2-amino-5-bromopyridin-3-yl)ethynyl)cyclobutyl)pyridin-2-yl)-3-chlorobenzamide To a solution of 5-bromo-3-iodopyridin-2-amine (25 mg, 0.084 mmol), Pd(PPh$_3$)$_2$Cl$_2$ (2.0 mg, 2.8 μmol), TEA (0.023 ml, 0.17 mmol), copper(I) iodide (1.0 mg, 5.2 mol) in MeCN (2 mL) was added 3-chloro-N-(5-(1-ethynylcyclobutyl)pyridin-2-yl)benzamide (26 mg, 0.083 mmol) at RT. After the addition was finished, the reaction was stirred at 80° C. for 16 h. The reaction was diluted with water, extracted with ethyl acetate. The combined organic layers were washed with brine, dried over Na$_2$SO$_4$, filtered and concentrated in vacuo to afford a residue, which was purified by prep-TLC (petroleum ether:ethyl acetate=2:1) to give the title compound. MS (EI) m/z 481 [M+H]$^+$.

Step 5: N-(5-(1-(5-bromo-1H-pyrrolo[2,3-b]pyridin-2-yl)cyclobutyl)pyridin-2-yl)-3-chlorobenzamide To a solution of N-(5-(1-((2-amino-5-bromopyridin-3-yl)ethynyl)cyclobutyl)pyridin-2-yl)-3-chlorobenzamide (20 mg, 0.042 mmol) in THF (1 mL) and DMF (0.15 mL) was added t-BuOK in THF (1 M, 0.09 mL, 0.09 mmol) at RT. The reaction was stirred at RT for 16 h, then diluted with NH$_4$Cl(sat.), extracted with ethyl acetate. The combined organic layers were washed with brine, dried over Na$_2$SO$_4$, filtered and concentrated in vacuo to give the title compound, which was used directly in next step without further purification. MS (EI) m/z 481 [M+H]$^+$.

Step 6: 3-Chloro-N-(5-(1-(5-cyano-1H-pyrrolo[2,3-b]pyridin-2-yl)cyclobutyl)pyridin-2-yl)benzamide (Ex. 6)

To a solution of N-(5-(1-(5-bromo-1H-pyrrolo[2,3-b]pyridin-2-yl)cyclobutyl)pyridin-2-yl)-3-chlorobenzamide (14 mg, 0.029 mmol), dppf (2.0 mg, 3.6 μmol) and zinc (1.0 mg, 0.015 mmol) in DMA (5 mL) were added dicyanozinc (10 mg, 0.085 mmol) and Pd$_2$(dba)$_3$ (1.0 mg, 1.1 μmol) at RT. After the addition was finished, the reaction mixture was irradiated in microwave at 150° C. for 1 h. The reaction was cooled to RT, poured into water, extracted with ethyl acetate. The combined organic layers were washed with brine, dried over Na$_2$SO$_4$, filtered and concentrated in vacuo to afford a residue, which was purified by reversed phase HPLC, eluting with water (10 mM NH$_4$HCO$_3$)-ACN to afford the title compound (Ex. 6). $^1$H NMR (400 MHz, CD$_3$OD) δ 8.44 (d, J=2.0 Hz, 1H), 8.34 (s, 1H), 8.29 (s, 1H), 8.05-8.03 (m, 1H), 8.02-8.01 (m, 2H), 7.93-7.91 (m, 1H), 7.64-7.63 (m, 1H), 7.56-7.52 (m, 1H), 6.63 (s, 1H), 2.90-2.83 (m, 4H), 2.18-2.11 (m, 2H); MS (EI) m/z 428 [M+H]$^+$.

Examples 7-27

Examples 7-27 shown in the following table were prepared in an analogous fashion to Example 3, using the corresponding phenyl diamines.

| Ex. # | Structure | Chemical Name | Mass [M + H]+ |
|---|---|---|---|
| 7 | 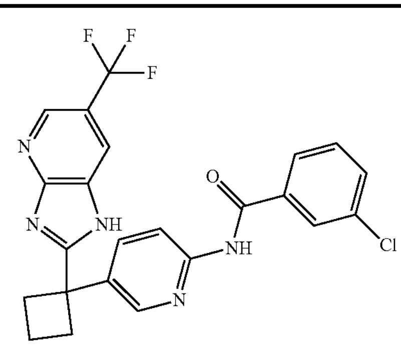 | 3-chloro-N-(5-{1-[6-(trifluoromethyl)-1H-imidazo[4,5-b]pyridin-2-yl]cyclobutyl}pyridin-2-yl)benzamide | Calc'd 472, found 472 |

| Ex. # | Structure | Chemical Name | Mass [M + H]+ |
|---|---|---|---|
| 8 | 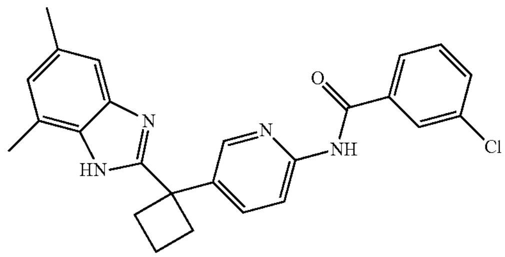 [SMILES: Cc1cc(C)c2[nH]c(C3(c4ccc(NC(=O)c5cccc(Cl)c5)nc4)CCC3)nc2c1] | 3-chloro-N-{5-[1-(5,7-dimethyl-1H-benzimidazol-2-yl)cyclobutyl]pyridin-2-yl}benzamide | Calc'd 431, found 431 |
| 9 | 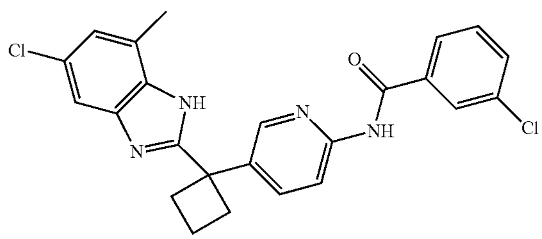 [SMILES: Cc1cc(Cl)cc2nc(C3(c4ccc(NC(=O)c5cccc(Cl)c5)nc4)CCC3)[nH]c12] | 3-chloro-N-{5-[1-(5-chloro-7-methyl-1H-benzimidazol-2-yl)cyclobutyl]pyridin-2-yl}benzamide | Calc'd 451, found 451 |
| 10 | 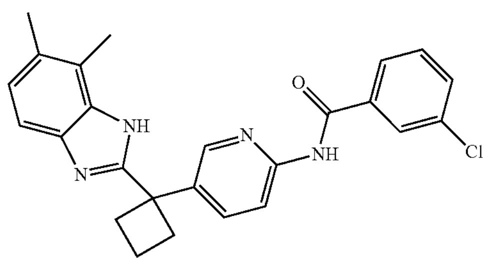 [SMILES: Cc1ccc2nc(C3(c4ccc(NC(=O)c5cccc(Cl)c5)nc4)CCC3)[nH]c2c1C] | 3-chloro-N-{5-[1-(6,7-dimethyl-1H-benzimidazol-2-yl)cyclobutyl]pyridin-2-yl}benzamide | Calc'd 431, found 431 |
| 11 | 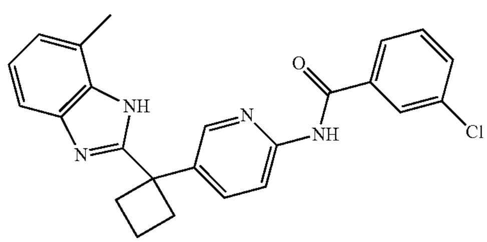 [SMILES: Cc1cccc2nc(C3(c4ccc(NC(=O)c5cccc(Cl)c5)nc4)CCC3)[nH]c12] | 3-chloro-N-{5-[1-(7-methyl-1H-benzimidazol-2-yl)cyclobutyl]pyridin-2-yl}benzamide | Calc'd 417, found 417 |
| 12 | 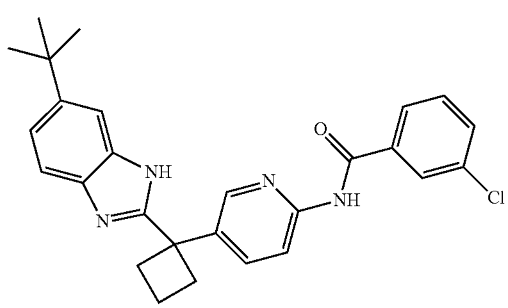 [SMILES: CC(C)(C)c1ccc2nc(C3(c4ccc(NC(=O)c5cccc(Cl)c5)nc4)CCC3)[nH]c2c1] | N-{5-[1-(6-tert-butyl-1H-benzimidazol-2-yl)cyclobutyl]pyridin-2-yl}-3-chlorobenzamide | Calc'd 459, found 459 |
| 13 | 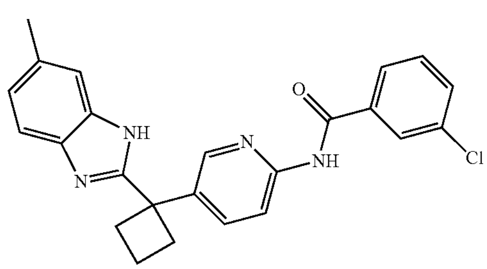 [SMILES: Cc1ccc2nc(C3(c4ccc(NC(=O)c5cccc(Cl)c5)nc4)CCC3)[nH]c2c1] | 3-chloro-N-{5-[1-(6-methyl-1H-benzimidazol-2-yl)cyclobutyl]pyridin-2-yl}benzamide | Calc'd 417, found 417 |

-continued

| Ex. # | Structure | Chemical Name | Mass [M + H]+ |
|---|---|---|---|
| 14 | 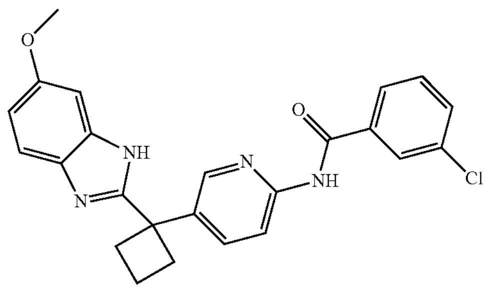 [SMILES: COc1ccc2nc(C3(c4ccc(NC(=O)c5cccc(Cl)c5)nc4)CCC3)[nH]c2c1] | 3-chloro-N-{5-[1-(6-methoxy-1H-benzimidazol-2-yl)cyclobutyl]pyridin-2-yl}benzamide | Calc'd 433, found 433 |
| 15 | 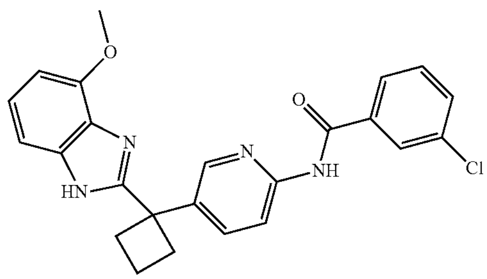 [SMILES: COc1cccc2[nH]c(C3(c4ccc(NC(=O)c5cccc(Cl)c5)nc4)CCC3)nc12] | 3-chloro-N-{5-[1-(4-methoxy-1H-benzimidazol-2-yl)cyclobutyl]pyridin-2-yl}benzamide | Calc'd 433, found 433 |
| 16 | 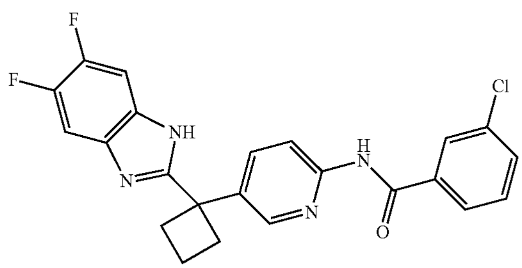 [SMILES: O=C(Nc1ccc(C2(c3nc4cc(F)c(F)cc4[nH]3)CCC2)cn1)c1cccc(Cl)c1] | 3-chloro-N-{5-[1-(5,6-difluoro-1H-benzimidazol-2-yl)cyclobutyl]pyridin-2-yl}benzamide | Calc'd 439, found 439 |
| 17 | 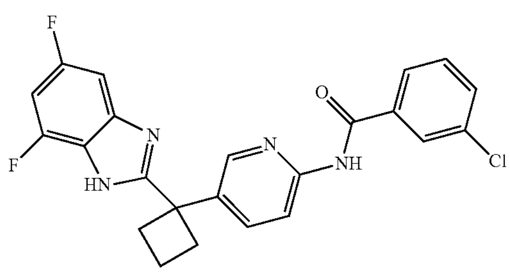 [SMILES: O=C(Nc1ccc(C2(c3nc4cc(F)cc(F)c4[nH]3)CCC2)cn1)c1cccc(Cl)c1] | 3-chloro-N-{5-[1-(5,7-difluoro-1H-benzimidazol-2-yl)cyclobutyl]pyridin-2-yl}benzamide | Calc'd 439, found 439 |
| 18 | 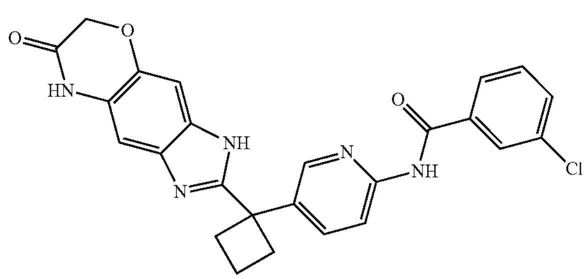 [SMILES: O=C1COc2cc3[nH]c(C4(c5ccc(NC(=O)c6cccc(Cl)c6)nc5)CCC4)nc3cc2N1] | 3-chloro-N-{5-[1-(7-oxo-3,6,7,8-tetrahydroimidazo[4,5-g][1,4]benzoxazin-2-yl)cyclobutyl]pyridin-2-yl}benzamide | Calc'd 474, found 474 |

| Ex. # | Structure | Chemical Name | Mass [M + H]+ |
|---|---|---|---|
| 19 | 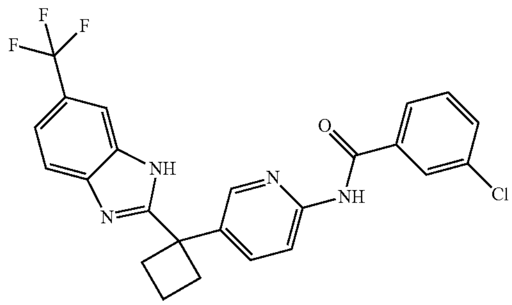 [SMILES: O=C(Nc1ccc(C2(c3nc4ccc(C(F)(F)F)cc4[nH]3)CCC2)cn1)c1cccc(Cl)c1] | 3-chloro-N-(5-{1-[6-(trifluoromethyl)-1H-benzimidazol-2-yl]cyclobutyl}pyridin-2-yl)benzamide | Calc'd 471, found 471 |
| 20 | 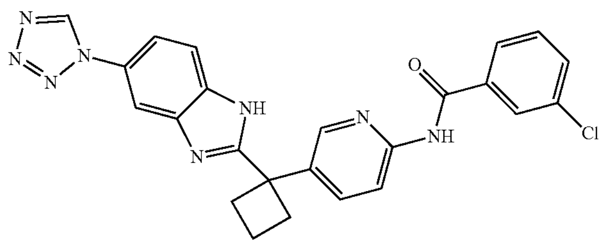 [SMILES: O=C(Nc1ccc(C2(c3nc4cc(-n5cnnn5)ccc4[nH]3)CCC2)cn1)c1cccc(Cl)c1] | 3-chloro-N-(5-{1-[5-(1H-tetrazol-1-yl)-1H-benzimidazol-2-yl]cyclobutyl}pyridin-2-yl)benzamide | Calc'd 471, found 471 |
| 21 | 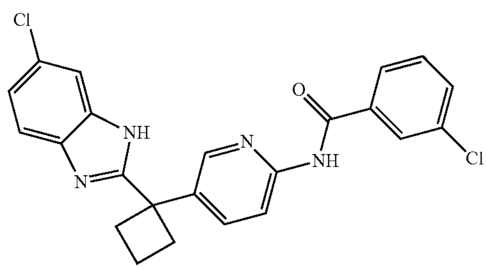 [SMILES: O=C(Nc1ccc(C2(c3nc4ccc(Cl)cc4[nH]3)CCC2)cn1)c1cccc(Cl)c1] | 3-chloro-N-{5-[1-(6-chloro-1H-benzimidazol-2-yl)cyclobutyl]pyridin-2-yl}benzamide | Calc'd 437, found 437 |
| 22 | 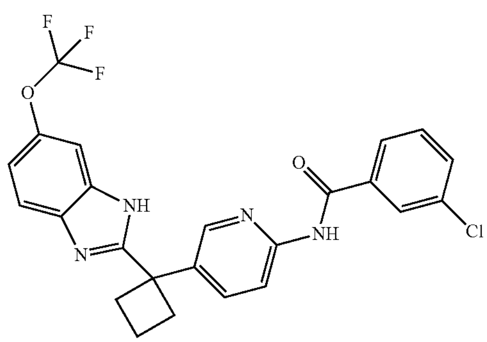 [SMILES: O=C(Nc1ccc(C2(c3nc4ccc(OC(F)(F)F)cc4[nH]3)CCC2)cn1)c1cccc(Cl)c1] | 3-chloro-N-(5-{1-[6-(trifluoromethoxy)-1H-benzimidazol-2-yl]cyclobutyl}pyridin-2-yl)benzamide | Calc'd 487, found 487 |
| 23 | 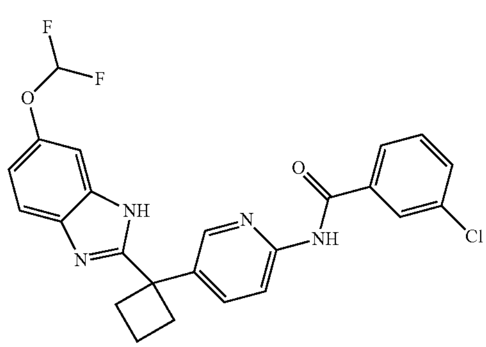 [SMILES: O=C(Nc1ccc(C2(c3nc4ccc(OC(F)F)cc4[nH]3)CCC2)cn1)c1cccc(Cl)c1] | 3-chloro-N-(5-{1-[6-(difluoromethoxy)-1H-benzimidazol-2-yl]cyclobutyl}pyridin-2-yl)benzamide | Calc'd 469, found 469 |

-continued

| Ex. # | Structure | Chemical Name | Mass [M + H]+ |
|---|---|---|---|
| 24 | 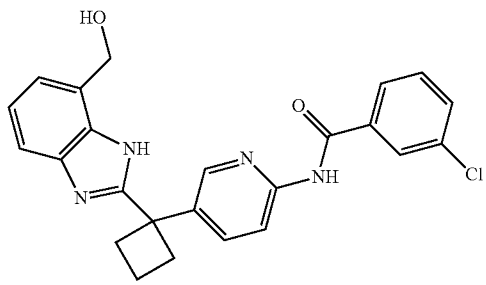 [SMILES: O=C(Nc1ccc(C2(c3nc4cccc(CO)c4[nH]3)CCC2)cn1)c1cccc(Cl)c1] | 3-chloro-N-(5-{1-[7-(hydroxymethyl)-1H-benzimidazol-2-yl]cyclobutyl}pyridin-2-yl)benzamide | Calc'd 433, found 433 |
| 25 | 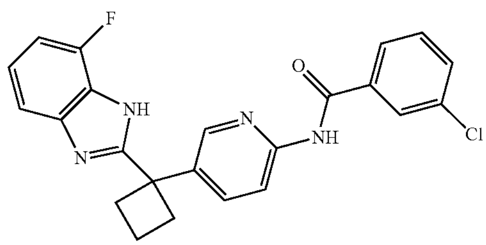 [SMILES: O=C(Nc1ccc(C2(c3nc4cccc(F)c4[nH]3)CCC2)cn1)c1cccc(Cl)c1] | 3-chloro-N-{5-[1-(7-fluoro-1H-benzimidazol-2-yl)cyclobutyl]pyridin-2-yl}benzamide | Calc'd 421, found 421 |
| 26 | 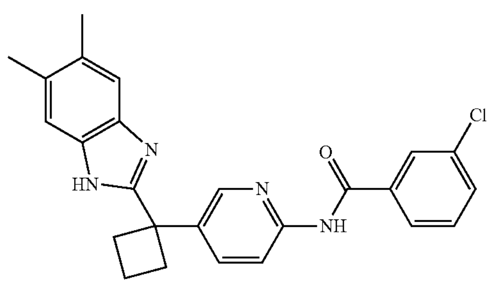 [SMILES: Cc1cc2nc(C3(c4ccc(NC(=O)c5cccc(Cl)c5)nc4)CCC3)[nH]c2cc1C] | 3-chloro-N-{5-[1-(5,6-dimethyl-1H-benzimidazol-2-yl)cyclobutyl]pyridin-2-yl}benzamide | Calc'd 431, found 431 |
| 27 | 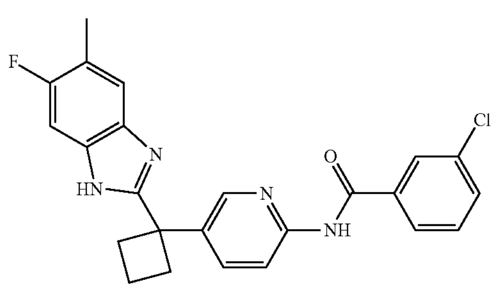 [SMILES: Cc1cc2nc(C3(c4ccc(NC(=O)c5cccc(Cl)c5)nc4)CCC3)[nH]c2cc1F] | 3-chloro-N-{5-[1-(6-fluoro-5-methyl-1H-benzimidazol-2-yl)cyclobutyl]pyridin-2-yl}benzamide | Calc'd 435, found 435 |

Examples 28-30

Examples 28-30 shown in the following table were prepared in an analogous fashion to Example 5, using the corresponding aromatic diamine.

| Ex. # | Structure | Chemical Name | Mass [M + H]+ |
|---|---|---|---|
| 28 | 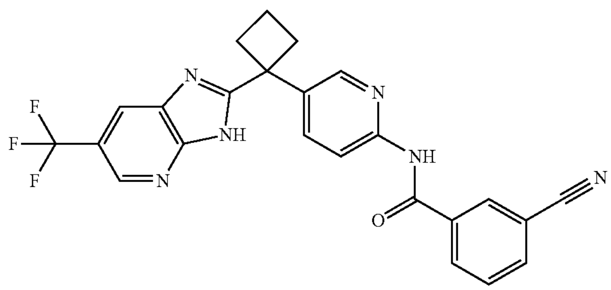 [SMILES: N#Cc1cccc(C(=O)Nc2ccc(C3(c4nc5cc(C(F)(F)F)cnc5[nH]4)CCC3)cn2)c1] | 3-cyano-N-(5-{1-[6-(trifluoromethyl)-3H-imidazo[4,5-b]pyridin-2-yl]cyclobutyl}pyridin-2-yl)benzamide | Calc'd 463, found 463 |
| 29 | 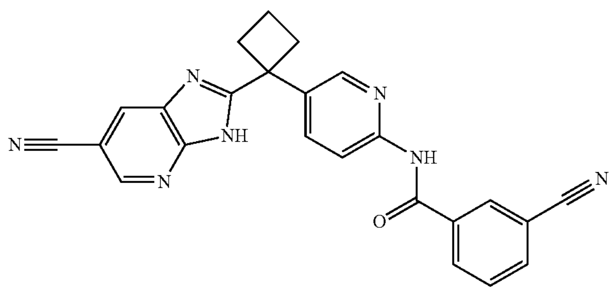 [SMILES: N#Cc1cccc(C(=O)Nc2ccc(C3(c4nc5cc(C#N)cnc5[nH]4)CCC3)cn2)c1] | 3-cyano-N-{5-[1-(6-cyano-3H-imidazo[4,5-b]pyridin-2-yl)cyclobutyl]pyridin-2-yl}benzamide | Calc'd 420, found 420 |
| 30 | 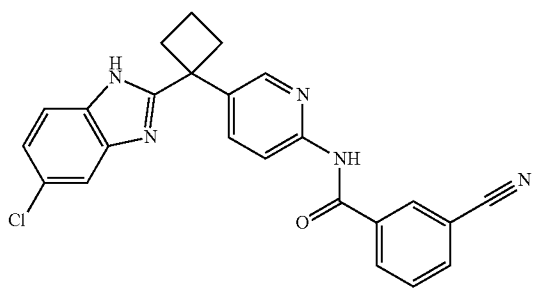 [SMILES: N#Cc1cccc(C(=O)Nc2ccc(C3(c4nc5cc(Cl)ccc5[nH]4)CCC3)cn2)c1] | N-(5-[1-(5-chloro-1H-benzimidazol-2-yl)cyclobutyl]pyridin-2-yl}-3-cyanobenzamide | Calc'd 428, found 428 |

Example 31: 3-Chloro-N-(5-(1-(1-(2-hydroxyethyl)-1H-benzo[d]imidazol-2-yl)cyclobutyl)pyridin-2-yl)benzamide

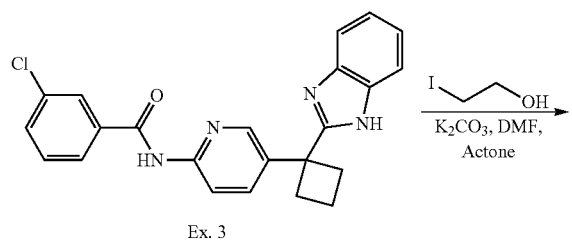

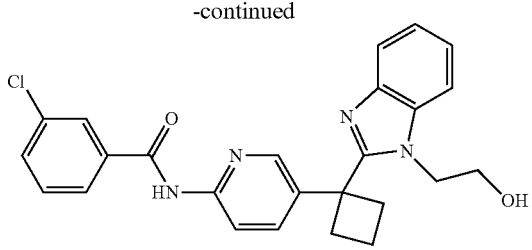

Ex. 31

To a vial containing Ex. 3 (60 mg, 0.12 mmol) were added $K_2CO_3$ (48.1 mg, 0.348 mmol), DMF (150 μL), acetone (750 μL) and 2-iodoethanol (22.7 mg, 0.132 mmol). The mixture was heated at 100° C. for 18 h, then filtered and purified by reversed phase HPLC, eluting with water (0.1% TFA)-ACN to afford the title compound as a TFA salt (Ex. 31). $^1$H NMR (600 MHz, DMSO-$d_6$) δ 11.06 (s, 1H), 8.53 (s, 1H), 8.16 (t, J=9.4 Hz, 1H), 8.00 (s, 1H), 7.91 (t, J=7.9 Hz, 2H), 7.79 (d, J=7.7 Hz, 2H), 7.63 (d, J=7.7 Hz, 1H), 7.55-7.42 (m, 3H), 4.18-4.06 (m, 2H), 3.39 (t, J=4.9 Hz, 2H), 3.16 (q, J=9.4 Hz, 2H), 2.91-2.75 (m, 2H), 2.20-1.91 (m, 2H). MS (EI) m/z 447 [M+H]$^+$.

Example 32: 3-Chloro-N-(5-(1-(7-(3-hydroxypropyl)-1H-benzo[d]imidazol-2-yl)cyclobutyl)pyridin-2-yl)benzamide

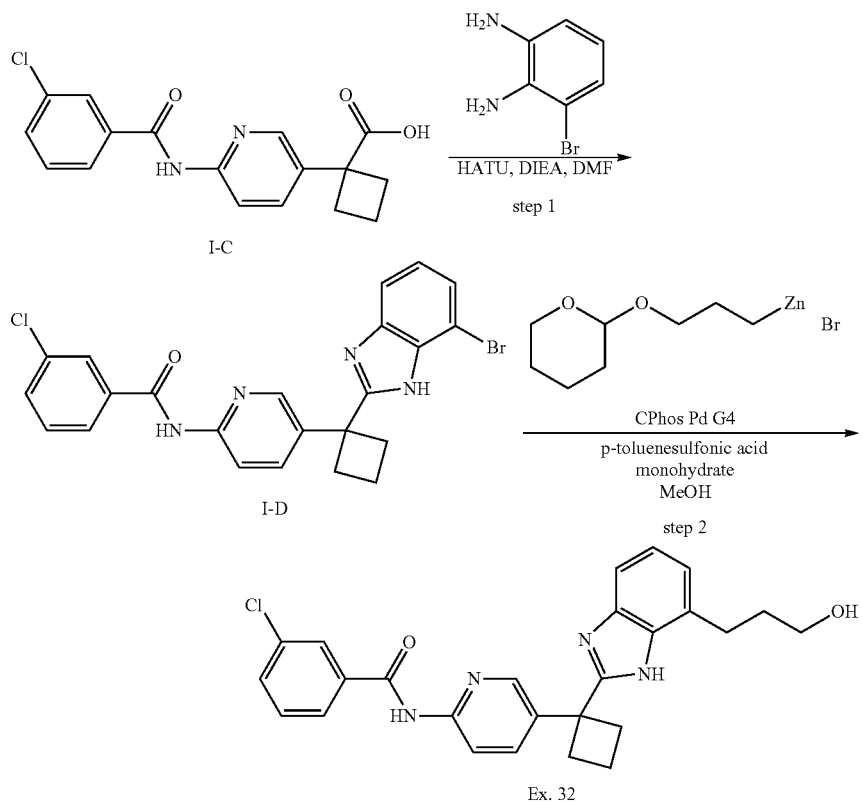

Step 1: N-(5-(1-(7-bromo-1H-benzo[d]imidazol-2-yl)cyclobutyl)pyridin-2-yl)-3-chlorobenzamide (I-D)

To a vial were added I-B (50 mg, 0.15 mmol), 3-bromobenzene-1,2-diamine (56.5 mg, 0.302 mmol), HATU (115 mg, 0.302 mmol), DMF (1 mL) and DIEA (80 μL, 0.46 mmol). The mixture was heated at 100° C. for 18 h. The solvent was removed in vacuo, and the residue was purified by column chromatography on silica gel (EtOAc in hexane, 0-50% gradient) to afford the title compound (I-D). MS (EI) m/z 481 [M+H]$^+$.

Step 2: 3-Chloro-N-(5-(1-(7-(3-hydroxypropyl)-1H-benzo[d]imidazol-2-yl)cyclobutyl)pyridin-2-yl)benzamide (Ex. 32)

To a vial was added I-D (28 mg, 0.058 mmol), CPhos Pd G4 (2.34 mg, 2.91 μmol), and (3-((tetrahydro-2H-pyran-2-yl)oxy)propyl)zinc(II) bromide 0.5M in THF (300 μL, 0.150 mmol). The reaction was heated at 40° C. for 2.5 h. The mixture was filtered through Celite and concentrated in vacuo. The residue was dissolved in a minimum volume of DCM and purified by column chromatography on silica gel (EtOAc/hex, 0-30% gradient) to yield 3-chloro-N-(5-(1-(7-(3-((tetrahydro-2H-pyran-2-yl)oxy)propyl)-1H-benzo[d]imidazol-2-yl)cyclobutyl)pyridin-2-yl)benzamide, which was dissolved in MeOH (500 μL). To this solution was added p-toluenesulfonic acid monohydrate (11 mg, 0.058 mmol). The mixture was stirred at RT for 2 h, then filtered and purified by reversed phase HPLC, eluting with water (0.1% TFA)-ACN to afford the title compound as a TFA salt (Ex. 32). $^1$H NMR (600 MHz, DMSO-d$_6$) δ 11.04 (s, 1H), 8.58-8.48 (m, 1H), 8.17 (d, J=8.6 Hz, 1H), 8.01 (s, 1H), 7.98-7.87 (m, 2H), 7.63 (d, J=7.7 Hz, 1H), 7.58-7.45 (m, 2H), 7.39 (t, J=7.5 Hz, 1H), 7.29 (d, J=6.9 Hz, 1H), 4.39 (t, J=6.3 Hz, 1H), 3.43 (t, J=6.2 Hz, 2H), 3.20-3.06 (m, 2H), 2.95 (t, J=7.5 Hz, 2H), 2.91-2.79 (m, 2H), 2.13-1.96 (m, 2H), 1.78 (p, J=6.6 Hz, 2H); MS (EI) m/z 461 [M+H]$^+$.

Example 33: 2-(2-(1-(6-(3-Chlorobenzamido)pyridin-3-yl)cyclobutyl)-1H-benzo[d]imidazol-7-yl)acetic acid

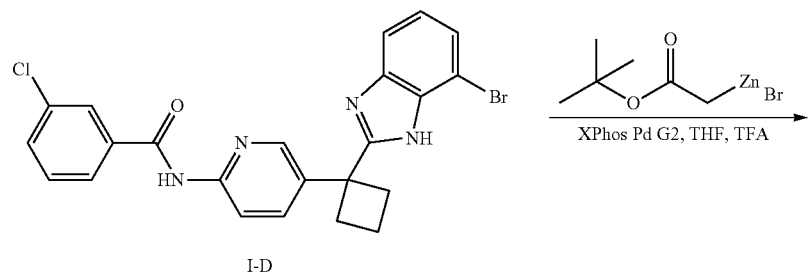

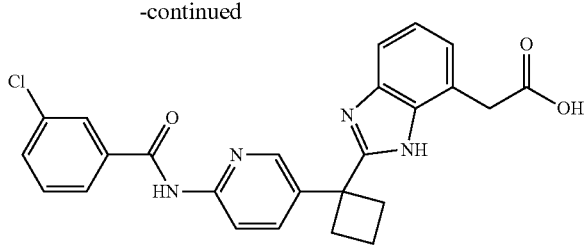

Ex. 33

To a vial were added I-D (23 mg, 0.048 mmol), XPhos Pd G2 (1.88 mg, 2.39 mol) and 800 uL of THF. The mixture was evacuated and back filled with $N_2$ 3 times, then (2-(tert-butoxy)-2-oxoethyl)zinc(II) bromide (400 μl, 0.200 mmol) was added. The reaction was heated at 40° C. for 20 h. To the reaction mixture was added TFA (50 μL, 0.65 mmol) and stirred at RT for 1 h. The mixture was filtered and purified by reversed phase HPLC, eluting with water (0.1% TFA)-ACN to afford the title compound as a TFA salt (Ex. 33). $^1$H NMR (600 MHz, DMSO-$d_6$) δ 11.04 (s, 1H), 8.50 (s, 1H), 8.17 (d, J=8.7 Hz, 1H), 8.01 (s, 1H), 7.97-7.88 (m, 2H), 7.63 (d, J=7.7 Hz, 1H), 7.59 (d, J=7.4 Hz, 1H), 7.51 (t, J=7.9 Hz, 1H), 7.43-7.35 (m, 1H), 7.35-7.28 (m, 1H), 3.97 (s, 2H), 3.09 (q, J=8.4 Hz, 2H), 2.95-2.76 (m, 2H), 2.16-1.94 (m, 2H); MS (EI) m/z 461 [M+H]$^+$.

Example 34: 3-Cyano-N-(5-(1-(7-(2-hydroxyethyl)-1H-benzo[d]imidazol-2-yl)cyclobutyl) pyridin-2-yl)benzamide

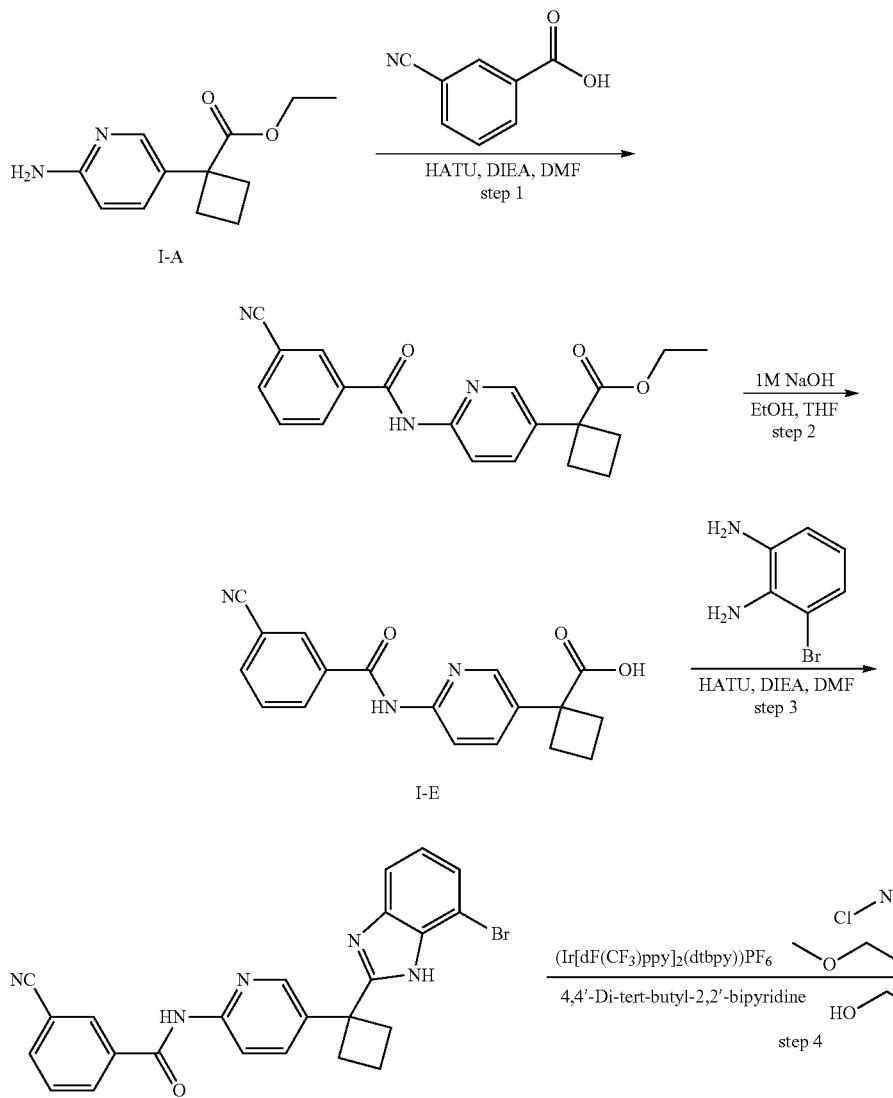

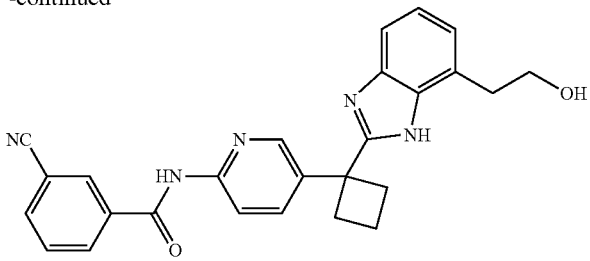

Ex. 34

Step 1: Ethyl 1-(6-(3-cyanobenzamido)pyridin-3-yl)cyclobutane-1-carboxylate

To a vial were added 3-cyanobenzoic acid (2.104 g, 14.30 mmol), I-A (3.00 g, 13.6 mmol), HATU (5.7 g, 15 mmol), DMF (100 ml) and DIEA (8.0 ml, 46 mmol). The mixture was stirred at RT for 19 h. Evaporated the solvent in vacuo to afford residue, which was purified by column chromatography on silica gel (EtOAc in hexane: 0-30% gradient) to afford ethyl 1-(6-(3-cyanobenzamido)pyridin-3-yl)cyclobutanecarboxylate. MS (EI) m/z 350 [M+H]$^+$.

Step 2: 1-(6-(3-Cyanobenzamido)pyridin-3-yl)cyclobutane-1-carboxylic acid (I-E)

To a flask were added ethyl 1-(6-(3-cyanobenzamido)pyridin-3-yl)cyclobutanecarboxylate (4.76 g, 13.6 mmol), THF (60 mL) and EtOH (20 mL). To this solution was added NaOH (1 M, 45 ml, 45 mmol). The mixture was stirred at RT for 24 h. Evaporated the organic solvent in vacuo. The aqueous solution was adjusted to pH-3 with addition of 1 M HCl. Some solid precipitated out, which was the desired product. The mixture was filtered to afford the title compound (I-E). MS (EI) m/z 322 [M+H]$^+$.

Step 3: N-(5-(1-(7-bromo-1H-benzo[d]imidazol-2-yl)cyclobutyl)pyridin-2-yl)-3-cyanobenzamide To a vial were added I-E (100 mg, 0.311 mmol), 3-bromobenzene-1,2-diamine (64.0 mg, 0.342 mmol), HATU (296 mg, 0.778 mmol), DMF (2000 μL) and DIEA (200 μL, 1.14 mmol). The mixture was stirred at RT for 18 h, then heated at 100° C. for 20 h. Evaporated the solvent in vacuo to afford a residue, which was purified by column chromatography on silica gel (EtOAc in hexane: 0-50% gradient) to afford the title compound. MS (EI) m/z 472 [M+H]$^+$.

Step 4: 3-Cyano-N-(5-(1-(7-(2-hydroxyethyl)-1H-benzo[d]imidazol-2-yl)cyclobutyl)pyridin-2-yl)benzamide (Ex. 34)

A. Preparation of [Ni] Complex—Stock Solution:
Degassed DME (300 μL) was added to a 2 dram vial containing Nickel(II) chloride ethylene glycol dimethyl ether complex (2.8 mg, 0.013 mmol) and 4,4'-di-tert-butyl-2,2'-bipyridine (3.4 mg, 0.013 mmol) under N$_2$. The resulting mixture was stirred for 25 min at RT to form a light green suspension.

B. Preparation of [Ir]—Stock Solution:
Degassed DME (1200 μL) was added to a vial containing (Ir[dF(CF$_3$)ppy]$_2$(dtbpy))PF$_6$ (2.85 mg, 2.54 μmol) under N$_2$. The resulting mixture was stirred for 10 min at RT to form a light yellow/green solution.

C. Reaction Setup:
Degassed DME (900 μL) was added to a 2 dram vial containing N-(5-(1-(7-bromo-1H-benzo[d]imidazol-2-yl)cyclobutyl)pyridin-2-yl)-3-cyanobenzamide (120 mg, 0.254 mmol), TTMSS (78 μL, 0.25 mmol), and anhydrous LiOH (12.2 mg, 0.508 mmol). The resulting mixture was stirred at RT for 5 min. DME (300 μl) of the Nickel stock solution was added in one portion, followed by DME (1200 μl) of the Ir stock solution. The resulting mixture was sparged with N$_2$ while stirring for 15 min, placed in the glovebox, followed by addition of 2-bromoethanol (47.6 mg, 0.381 mmol), then switched to a new cap and sealed with Parafilm. The reaction mixture was taken outside of the glovebox, stirred and irradiated in Merck photoreactor for 16 h. The mixture was filtered and purified by reversed phase HPLC, eluting with water (0.1% TFA)-ACN to afford the title compound as a TFA salt (Ex. 34). $^1$H NMR (600 MHz, DMSO-d$_6$) δ 11.15 (s, 1H), 8.54 (s, 1H), 8.41 (s, 1H), 8.23 (d, J=7.9 Hz, 1H), 8.19 (d, J=8.7 Hz, 1H), 8.03 (d, J=7.6 Hz, 1H), 7.96 (d, J=8.6 Hz, 1H), 7.69 (t, J=7.8 Hz, 1H), 7.54 (d, J=8.0 Hz, 1H), 7.39 (t, J=7.6 Hz, 1H), 7.31 (d, J=7.1 Hz, 1H), 3.69 (t, J=6.6 Hz, 2H), 3.19-3.01 (m, 4H), 2.93-2.77 (m, 2H), 2.12-1.94 (m, 2H); MS (EI) m/z 438 [M+H]$^+$.

Example 35: Methyl 2-(1-(6-(3-cyanobenzamido)pyridin-3-yl)cyclobutyl)-1H-benzo[d]imidazole-7-carboxylate

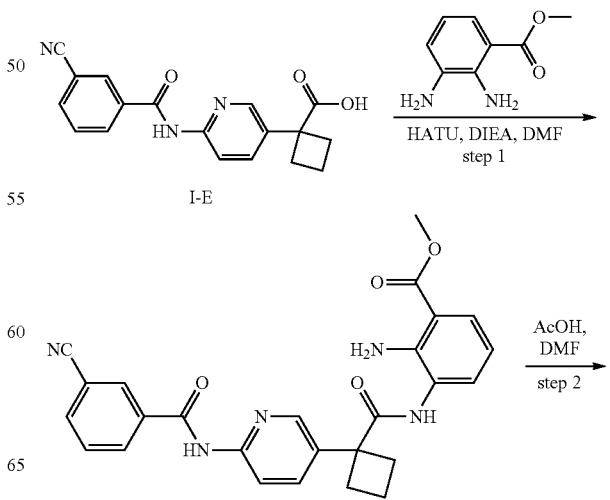

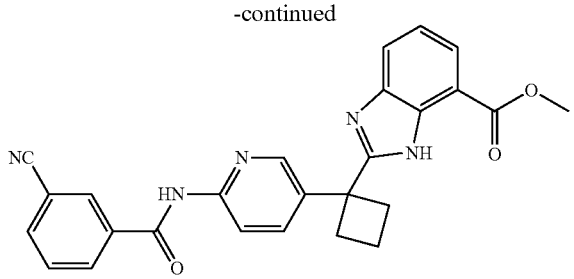

Ex. 35

Step 1: Methyl 2-amino-3-(1-(6-(3-cyanobenzamido)pyridin-3-yl)cyclobutane-1-carboxamido)benzoate To a flask were added I-E (199 mg, 0.621 mmol), methyl 2,3-diaminobenzoate (136 mg, 0.818 mmol), HATU (364 mg, 0.957 mmol), DMF (5 ml) and DIEA (0.30 ml, 1.7 mmol). The mixture was stirred at RT for 18 h. Then the solvent was concentrated in vacuo to afford a residue, which was purified by column chromatography on silica gel (EtOAc in hexane: 0-70% gradient) to afford the title compound. MS (EI) m/z 470 [M+H]$^+$.

Step 2: Methyl 2-(1-(6-(3-cyanobenzamido)pyridin-3-yl)cyclobutyl)-1H-benzo[d]imidazole-7-carboxylate (Ex. 35)

To a vial were added methyl 2-amino-3-(1-(6-(3-cyanobenzamido)pyridin-3-yl) cyclobutanecarboxamido)benzoate (51 mg, 0.11 mmol), DMF (600 µL) and acetic acid (150 µL). The mixture was irradiated in microwave at 130° C. for 4 h. Evaporated the solvent in vacuo to afford a residue, which was diluted with NaHCO$_3$ (sat.) and EtOAc. The aqueous layer was extracted with EtOAc 3 times. The combined organic layers were washed with brine, dried over Na$_2$SO$_4$, filtered and concentrated in vacuo to afford a residue, which was purified by column chromatography on silica gel (EtOAc in hexane: 0-80% gradient) to afford the title compound (Ex. 35). $^1$H NMR (499 MHz, DMSO-d$_6$) δ 12.02 (s, 1H), 11.07 (s, 1H), 8.50-8.39 (m, 2H), 8.27 (d, J=7.9 Hz, 1H), 8.13 (d, J=8.6 Hz, 1H), 8.06 (d, J=7.6 Hz, 1H), 7.94 (d, J=7.7 Hz, 1H), 7.87 (d, J=8.0 Hz, 1H), 7.78 (d, J=7.4 Hz, 1H), 7.72 (t, J=7.8 Hz, 1H), 7.29 (t, J=7.7 Hz, 1H), 3.91 (s, 3H), 3.19-3.03 (m, 2H), 2.77 (q, J=8.6 Hz, 2H), 2.08-1.95 (m, 2H); MS (EI) m/z 452 [M+H]$^+$.

Example 36: 2-(1-(6-(3-Cyanobenzamido)pyridin-3-yl)cyclobutyl)-1H-benzo[d]imidazole-7-carboxylic acid

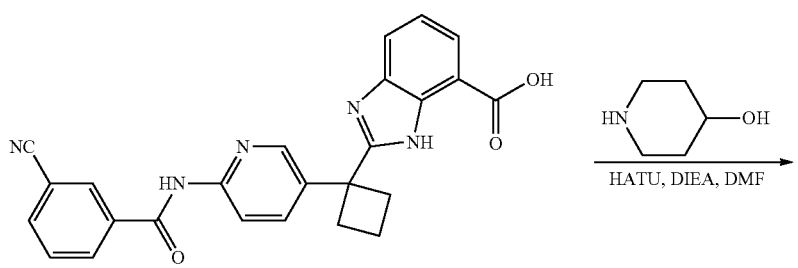

Ex. 35

Ex. 36

To a vial containing Ex. 35 (33 mg, 0.074 mmol) were added THF (450 µL), MeOH (150 µL) and NaOH (1 M, 3 mL, 0.3 mmol). The mixture was stirred at RT for 2 days. The mixture was filtered and purified by reversed phase HPLC, eluting with water (0.1% TFA)-ACN to afford the title compound as a TFA salt (Ex. 36). $^1$H NMR (600 MHz, DMSO-d$_6$) δ 11.09 (s, 1H), 8.50 (s, 1H), 8.40 (s, 1H), 8.23 (d, J=7.8 Hz, 1H), 8.13 (d, J=8.6 Hz, 1H), 8.02 (d, J=7.5 Hz, 1H), 7.97-7.91 (m, 2H), 7.88 (d, J=7.3 Hz, 1H), 7.69 (t, J=7.8 Hz, 1H), 7.42 (t, J=7.5 Hz, 1H), 3.11 (q, J=7.7 Hz, 2H), 2.80 (q, J=7.8 Hz, 2H), 2.11-1.84 (m, 2H). MS (EI) m/z 438 [M+H]$^+$.

Example 37: 3-Cyano-N-(5-(1-(7-(4-hydroxypiperidine-1-carbonyl)-1H-benzo[d]imidazol-2-yl)cyclobutyl)pyridin-2-yl)benzamide Ex. 36

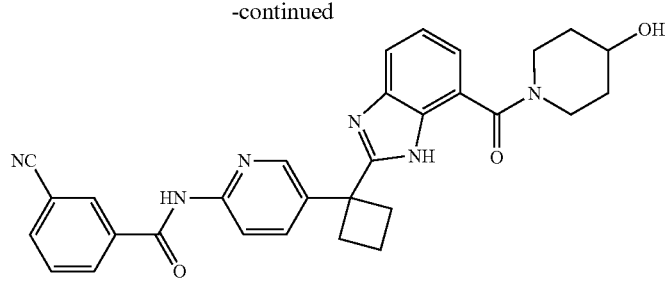

Ex. 37

To a vial were added Ex. 36 (21 mg, 0.048 mmol), piperidin-4-ol (15 mg, 0.15 mmol), HATU (36.5 mg, 0.0960 mmol), DMF (400 μL) and DIEA (30 μL, 0.17 mmol). The mixture was heated at 50° C. for 1 h. The mixture was filtered and purified by reversed phase HPLC, eluting with water (0.1% TFA)-ACN to afford the title compound as a TFA salt (Ex. 37). $^1$H NMR (600 MHz, DMSO-$d_6$) δ 11.12 (s, 1H), 8.46 (s, 1H), 8.41 (s, 1H), 8.23 (d, J=7.9 Hz, 1H), 8.15 (t, J=7.9 Hz, 1H), 8.03 (d, J=7.6 Hz, 1H), 7.91 (d, J=8.5 Hz, 1H), 7.73-7.62 (m, 2H), 7.38 (t, J=7.3 Hz, 1H), 7.30 (d, J=6.7 Hz, 1H), 4.13-3.95 (m, 1H), 3.77-3.67 (m, 1H), 3.43-3.25 (m, 2H), 3.16-2.98 (m, 3H), 2.88-2.74 (m, 2H), 2.11-1.94 (m, 2H), 1.89-1.74 (m, 1H), 1.69-1.18 (m, 3H). MS (EI) m/z 521 [M+H]$^+$.

Example 38

Example 38 shown in the following table was prepared in an analogous fashion to Ex. 37, using the corresponding amine.

| Ex. # | Structure | Chemical Name | Mass [M + H]+ |
|---|---|---|---|
| 38 | (structure shown) | 3-cyano-N-(5-{1-[7-(pyrrolidine-1-carbonyl)-1H-benzimidazol-2-yl]cyclobutyl}pyridin-2-yl)benzamide | Calc'd 491, found 491 |

Example 39: 3-Cyano-N-(5-(methoxy(6-(trifluoromethyl)-3H-imidazo[4,5-b]pyridin-2-yl)methyl)pyridin-2-yl)benzamide

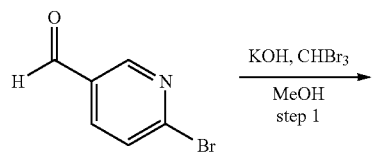

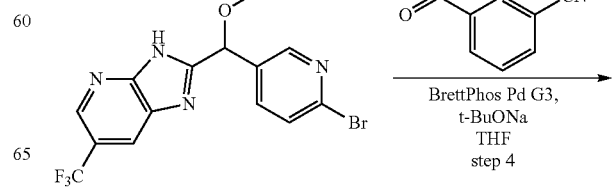

-continued

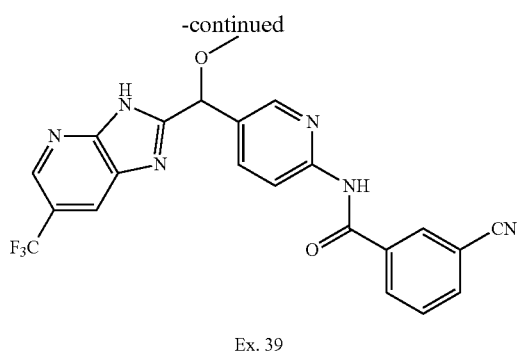

Ex. 39

Step 1: 2-(6-Bromopyridin-3-yl)-2-methoxyacetic acid

To a stirred solution of 6-bromonicotinaldehyde (2.0 g, 11 mmol) and CHBr₃ (1.128 mL, 12.90 mmol) in MeOH (10 mL) was KOH (3.02 g, 53.8 mmol) at 0° C. After the addition was finished, the reaction was stirred at RT for 16 h. The reaction was diluted with water, extracted with ethyl acetate. The aqueous solution was collected and adjusted to pH-5 with addition of 1N HCl, then extracted with ethyl acetate. The combined organic layers were washed with brine, dried over Na₂SO₄, filtered and concentrated in vacuo to give the title compound, which was used directly in next step without further purification. MS (EI) m/z 246 [M+H]⁺.

Step 2: N-(2-Amino-5-(trifluoromethyl)pyridin-3-yl)-2-(6-bromopyridin-3-yl)-2-methoxyacetamide To a stirred solution of 2-(6-bromopyridin-3-yl)-2-methoxyacetic acid (500 mg, 2.03 mmol) in pyridine (5 mL) was added 5-(trifluoromethyl)pyridine-2,3-diamine (396 mg, 2.23 mmol) and EDC (1.17 g, 6.10 mmol) at RT. After the addition was finished, the reaction was stirred at 40° C. for 4 h. The solvent was removed in vacuo. The residue was diluted with water, extracted with ethyl acetate. The combined organic layers were washed with brine, dried over Na₂SO₄, filtered and concentrated in vacuo to afford a residue, which was purified by prep-TLC (petroleum ether:ethyl acetate=1:1) to give the title compound. MS (EI) m/z 405 [M+H]⁺.

Step 3: 2-((6-Bromopyridin-3-yl)(methoxy)methyl)-6-(trifluoromethyl)-3H-imidazo[45-b]pyridine To a stirred solution of N-(2-amino-5-(trifluoromethyl)pyridin-3-yl)-2-(6-bromopyridin-3-yl)-2-methoxyacetamide (600 mg, 1.48 mmol) in DMF (8 mL) was added AcOH (2.0 mL, 35 mmol) at RT. After the addition was finished, the reaction was stirred at 130° C. for 16 h. The reaction was cooled to RT. The solvent was removed in vacuo. The residue was diluted with NaHCO₃ (sat.), extracted with ethyl acetate. The combined organic layers were washed with brine, dried over Na₂SO₄, filtered and concentrated in vacuo to afford a residue, which was purified by reversed phase HPLC, eluting with water (0.1% TFA)-ACN to afford the title compound. MS (EI) m/z 387 [M+H]⁺.

Step 4: 3-Cyano-N-(5-(methoxy(6-(trifluoromethyl)-3H-imidazo[4,5-b]pyridin-2-yl)methyl)pyridin-2-yl)benzamide (Ex. 39)

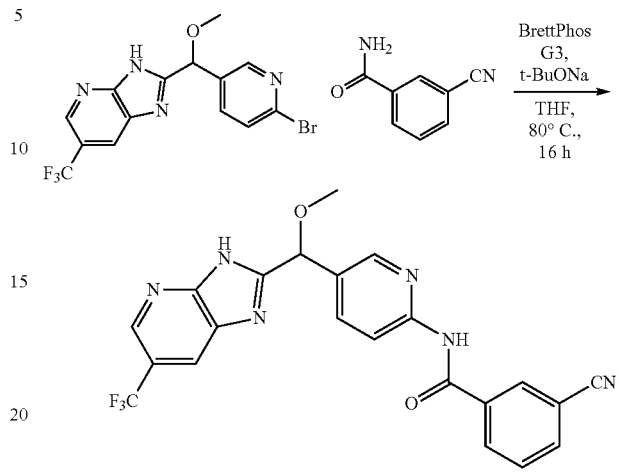

To a stirred solution of 2-((6-bromopyridin-3-yl)(methoxy)methyl)-6-(trifluoromethyl)-3H-imidazo[4,5-b]pyridine (200 mg, 0.517 mmol) in THF (5 mL) were added 3-cyanobenzamide (113 mg, 0.775 mmol) and sodium 2-methylpropan-2-olate (99 mg, 1.0 mmol), Brettphos Pd G3 (47 mg, 0.052 mmol) at RT. After the addition was finished, the reaction was stirred at 60° C. for 16 h. The reaction was diluted with water, extracted with ethyl acetate. The combined organic layers were washed with brine, dried over Na₂SO₄, filtered and concentrated in vacuo to afford a residue, which was purified by reversed phase HPLC, eluting with water (0.1% TFA)-ACN to afford the title compound as a TFA salt (Ex. 39). ¹H NMR (400 MHz, CD₃OD) δ 8.67 (s, 1H), 8.52 (d, J=1.8 Hz, 1H), 8.32 (t, J=1.4 Hz, 1H), 8.28-8.24 (m, 3H), 7.96-7.94 (m, 2H), 7.74-7.72 (m, 1H), 5.77 (s, 1H), 3.54 (s, 3H); MS (EI) m/z: 453 [M+H]⁺.

Example 40 and 41: (S)-3-cyano-N-(5-(methoxy(6-(trifluoromethyl)-3H-imidazo[4,5-b]pyridin-2-yl)methyl)pyridin-2-yl)benzamide and (R)-3-cyano-N-(5-(methoxy(6-(trifluoromethyl)-3H-imidazo[4,5-b]pyridin-2-yl)methyl)pyridin-2-yl)benzamide

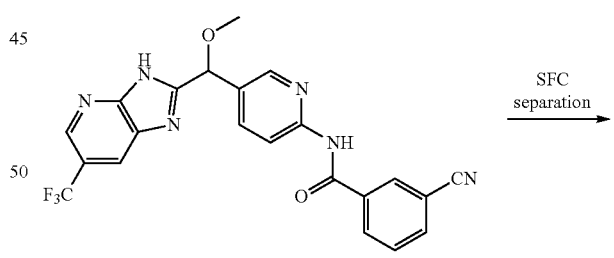

Ex. 39

SFC separation

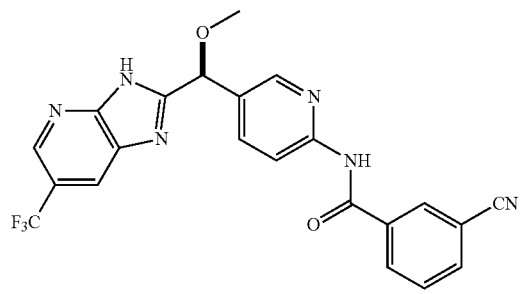

Ex. 40

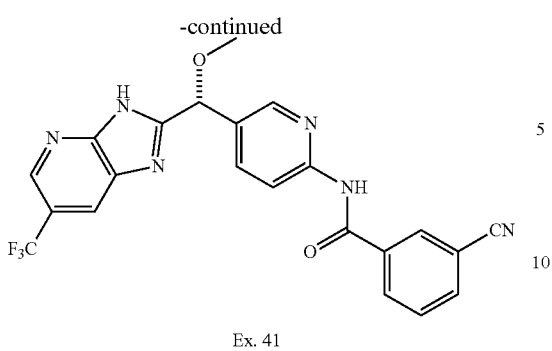

Ex. 41

Example 39 was submitted to SFC chiral separation (Column: Chiralcel OD-3 100×4.6 mm I.D., 3 um; Mobile phase A: $CO_2$; Mobile phase B: Ethanol with 0.05% DEA) to afford Examples 40 and 41.

Example 40: retention time: 3.050 min; $^1$H NMR (400 MHz, CD3OD) δ 8.67 (s, 1H), 8.52 (d, J=1.8 Hz, 1H), 8.32 (t, J=1.4 Hz, 1H), 8.28-8.24 (m, 3H), 7.96-7.94 (m, 2H), 7.74-7.72 (m, 1H), 5.77 (s, 1H), 3.54 (s, 3H); MS (EI) m/z: 453 [M+H]$^+$.

Example 41: retention time: 3.221 min; $^1$H NMR (400 MHz, CD$_3$OD) δ 8.67 (s, 1H), 8.52 (d, J=1.8 Hz, 1H), 8.32 (t, J=1.4 Hz, 1H), 8.28-8.24 (m, 3H), 7.96-7.94 (m, 2H), 7.74-7.72 (m, 1H), 5.77 (s, 1H), 3.54 (s, 3H); MS (EI) m/z: 453 [M+H]$^+$.

Example 42: 3-Cyano-N-(5-(hydroxy(6-(trifluoromethyl)-3H-imidazo[4,5-b]pyridin-2-yl)methyl)pyridin-2-yl)benzamide

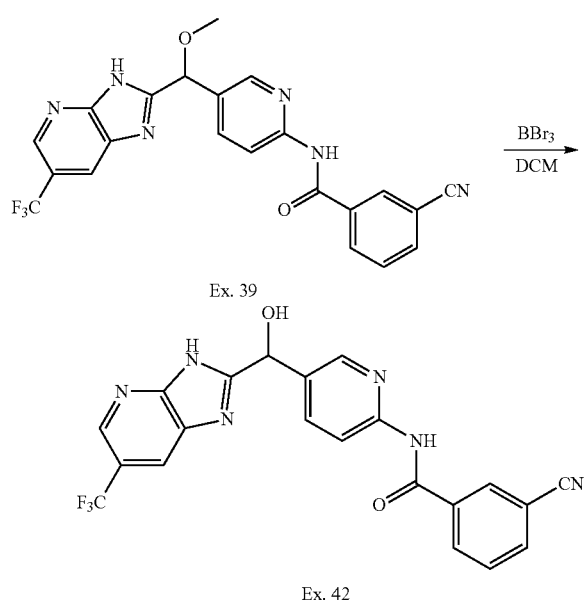

To a stirred solution of Ex. 39 (120 mg, 0.265 mmol) in DCM (5 mL) was added BBr$_3$ (1 M in THF, 0.5 mL, 0.5 mmol) at 0° C. After the addition was finished, the reaction was stirred at RT for 2 h. The reaction was quenched by addition of MeOH. The solvent was removed in vacuo to afford a residue, which was purified by reversed phase HPLC, eluting with water (0.1% TFA)-ACN to afford the title compound as a TFA salt (Ex. 42). $^1$H NMR (400 MHz, CD$_3$OD) δ 8.69 (s, 1H), 8.59 (s, 1H), 8.35 (s, 1H), 8.27-8.24 (m, 2H), 8.17-8.15 (m, 1H), 8.12-8.10 (m, 1H), 7.99-7.97 (m, 1H), 7.75-7.71 (m, 1H), 6.20 (s, 1H); MS (EI) m/z: 439 [M+H]$^+$.

Example 43 and 44: (S)-3-cyano-N-(5-(hydroxy(6-(trifluoromethyl)-3H-imidazo[4,5-b]pyridin-2-yl)methyl)pyridin-2-yl)benzamide and (R)-3-cyano-N-(5-(hydroxy(6-(trifluoromethyl)-3H-imidazo[4,5-b]pyridin-2-yl)methyl)pyridin-2-yl)benzamide Example 42 was submitted to SFC chiral separation (Column: Chiralcel OD-3 100×4.6 mm I.D., 3 um; Mobile phase A: $CO_2$; Mobile phase B: Ethanol with 0.05% DEA) to afford Examples 43 and 44.

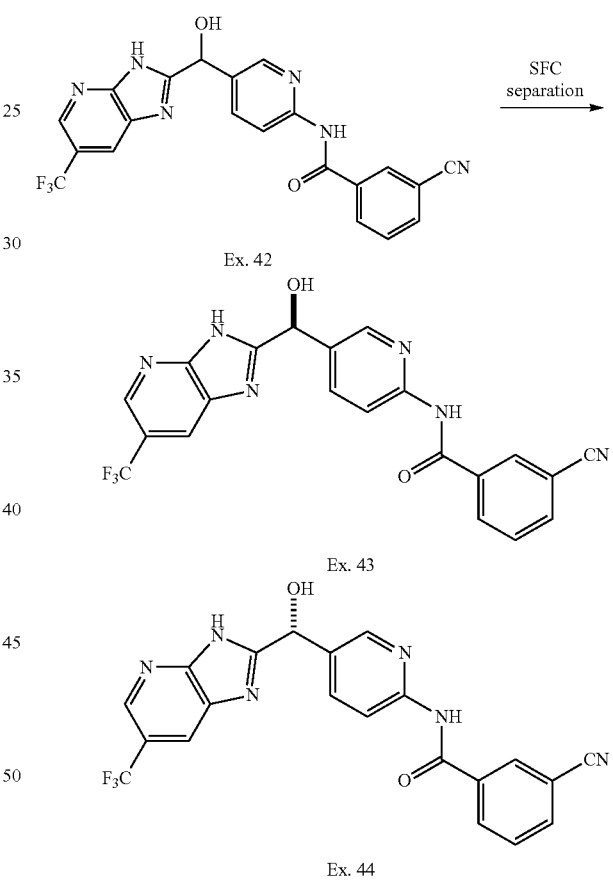

Example 43: retention time: 3.281 min; $^1$H NMR (400 MHz, CD$_3$OD) δ 8.69 (s, 1H), 8.59 (s, 1H), 8.35 (s, 1H), 8.27-8.24 (m, 2H), 8.17-8.15 (m, 1H), 8.12-8.10 (m, 1H), 7.99-7.97 (m, 1H), 7.75-7.71 (m, 1H), 6.20 (s, 1H); MS (EI) m/z: 439 [M+H]$^+$.

Example 44: retention time: 3.837 min; $^1$H NMR (400 MHz, CD$_3$OD) δ 8.69 (s, 1H), 8.59 (s, 1H), 8.35 (s, 1H), 8.27-8.24 (m, 2H), 8.17-8.15 (m, 1H), 8.12-8.10 (m, 1H), 7.99-7.97 (m, 1H), 7.75-7.71 (m, 1H), 6.20 (s, 1H); MS (EI) m/z: 439 [M+H]$^+$.

Example 45: 3-Cyano-N-(6-(1-(6-(trifluoromethyl)-1H-imidazo[4,5-b]pyridin-2-yl)cyclobutyl)pyridin-3-yl)benzamide

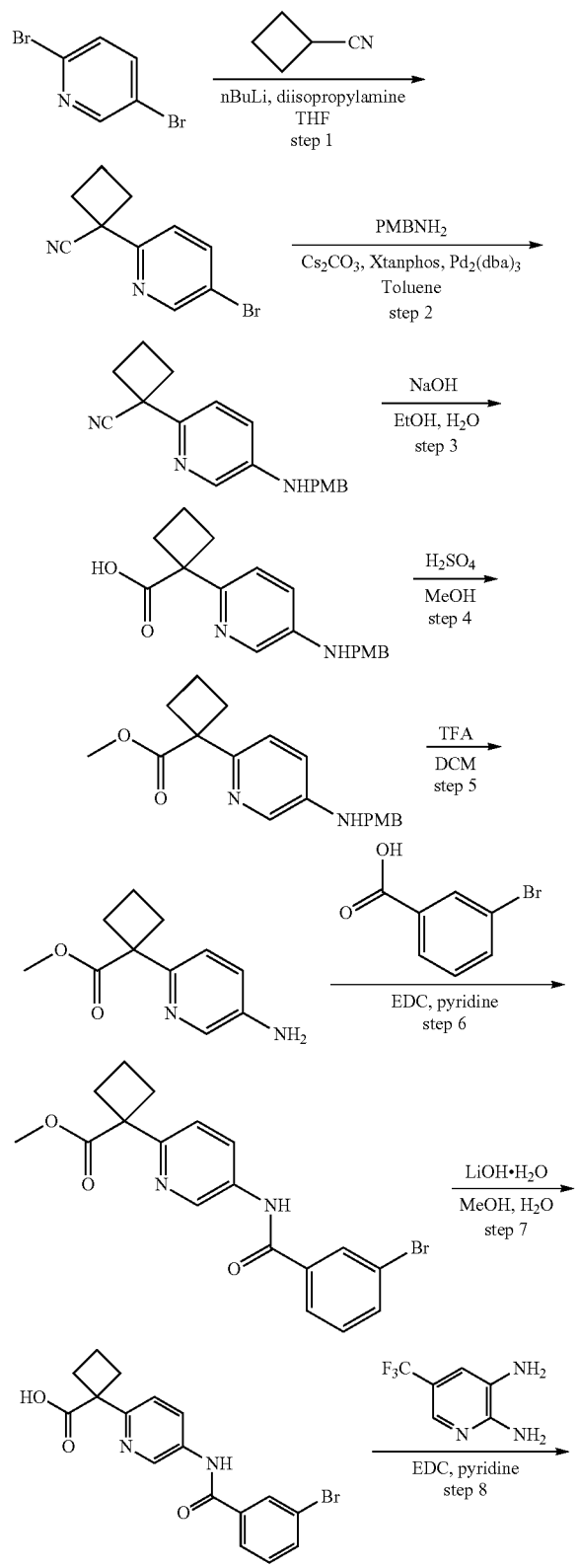

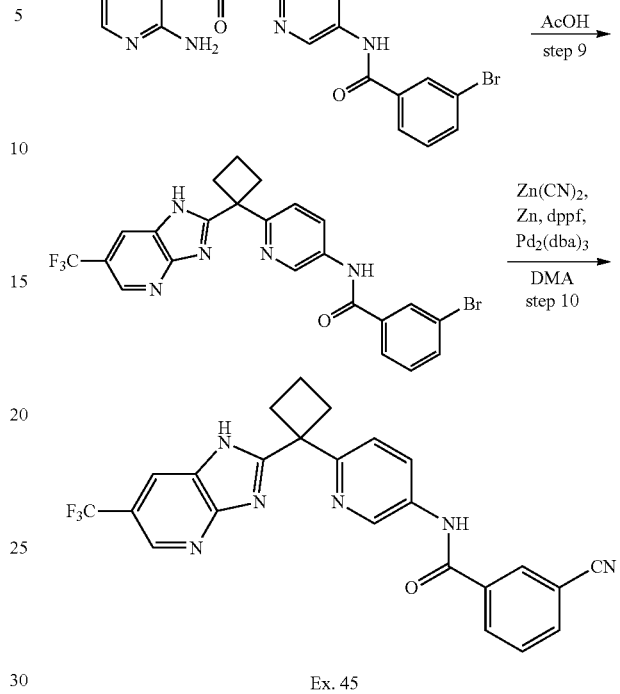

Ex. 45

Step 1: 1-(5-Bromopyridin-2-yl)cyclobutane-1-carbonitrile

To a stirred solution of diisopropylamine (60.0 g, 593 mmol) in THF (300.0 mL) was added n-BuLi (237 mL, 593 mmol) (2.5 N) dropwise at −10° C. under nitrogen atmosphere. The reaction was stirred at the same temperature for 30 min. Then the reaction mixture was cooled to −78° C., a solution of cyclobutanecarbonitrile (49.3 g, 608 mmol) in THF (50.0 mL) was added dropwise to the reaction mixture at −78° C. and the reaction mixture was stirred at the same temperature for 40 min. A solution of 2,5-dibromopyridine (120 g, 507 mmol) in THF (250 ml) was then added. After the addition was finished, the reaction mixture was stirred at RT for 18 h. The solvent was removed in vacuo. The residue was partitioned between water and ethyl acetate. The organic layer was separated and washed with brine, dried over $Na_2SO_4$, filtered and concentrated in vacuo to afford a residue, which was purified by column chromatography on silica gel (EtOAc in petroleum ether: 0-5% gradient) to give the title compound. MS (EI) m/z 237 [M+H]⁺.

Step 2: 1-(5-((4-Methoxybenzyl)amino)pyridin-2-yl)cyclobutane-1-carbonitrile To a solution of 1-(5-bromopyridin-2-yl)cyclobutanecarbonitrile (1.0 g, 4.2 mmol) and (4-methoxyphenyl)methanamine (0.694 g, 5.06 mmol) in Toluene (20 mL) were added $Cs_2CO_3$ (2.06 g, 6.33 mmol), $Pd_2(dba)_3$ (0.193 g, 0.211 mmol) and Xantphos (0.366 g, 0.633 mmol) at RT under $N_2$ atmosphere. After the addition was complete, the reaction mixture was stirred at 110° C. for 14 h. The reaction was cooled to RT and filtered. The filtrate was concentrated in vacuo to afford a residue, which was purified by column chromatography on silica gel (EtOAc in petroleum ether: 0-50% gradient) to give the title compound. MS (EI) m/z 294 [M+H]$^+$.

Step 3: 1-(5-((4-Methoxybenzyl)amino)pyridin-2-yl) cyclobutane-1-carboxylic acid To a solution of 1-(5-((4-methoxybenzyl)amino)pyridin-2-yl)cyclobutanecarbonitrile (860 mg, 2.93 mmol) in water (2 mL) and EtOH (10 mL) was added NaOH (586 mg, 14.7 mmol) at RT. After the addition was complete, the reaction mixture was stirred at 85° C. for 18 h. The reaction was cooled to RT, and concentrated in vacuo. The residue was diluted with DCM and filtered. The filter cake was suspended in EtOAc and water. Then 3N HCl was added to adjust aqueous layer pH-3. The mixture was extracted with EtOAc. The combined organic layers were washed with brine, dried over Na$_2$SO$_4$, filtered and concentrated in vacuo to give the title compound, which was used in the next step without further purification. MS (EI) m/z 313 [M+H]$^+$.

Step 4: Methyl 1-(5-((4-methoxybenzyl)amino)pyridin-2-yl)cyclobutane-1-carboxylate To a stirred solution of 1-(5-((4-methoxybenzyl)amino) pyridin-2-yl)cyclobutanecarboxylic acid (916 mg, 2.93 mmol) in MeOH (10 mL) was added sulfuric acid (0.288 mL, 5.28 mmol) dropwise at 0° C. Then the resulting mixture was stirred at 50° C. for 16 h. The solvent was evaporated in vacuo. The residue was diluted with water, extracted with DCM. The combined organic layers were washed with brine, dried over Na$_2$SO$_4$, filtered and concentrated in vacuo to afford a residue, which was purified by prep-TLC (petroleum ether:ethyl acetate=1:1) to give the title compound. MS (EI) m/z 327 [M+H]$^+$.

Step 5: Methyl 1-(5-aminopyridin-2-yl)cyclobutane-1-carboxylate

To a solution of methyl 1-(5-((4-methoxybenzyl)amino) pyridin-2-yl)cyclobutanecarboxylate (200 mg, 0.613 mmol) in DCM (5 mL) were added TFA (0.236 mL, 3.06 mmol) at RT. The mixture was stirred at RT for 16 h. The solvent was removed in vacuo. The residue was diluted with water, adjusted to pH-9 with 2N NaOH, extracted with ethyl acetate. The combined organic layers were washed with brine, dried over Na$_2$SO$_4$, filtered and concentrated in vacuo to afford a residue, which was purified by column chromatography on silica gel (EtOAc in petroleum ether: 0-20% gradient) to give the title compound. MS (EI) m/z 207 [M+H]$^+$.

Step 6: Methyl 1-(5-(3-bromobenzamido)pyridin-2-yl)cyclobutane-1-carboxylate To a solution of methyl 1-(5-aminopyridin-2-yl)cyclobutanecarboxylate (348 mg, 1.69 mmol) in pyridine (50 mL) was added 3-bromobenzoic acid (407 mg, 2.02 mmol) and EDC (970 mg, 5.06 mmol) at RT. After the addition was complete, the reaction mixture was stirred at 30° C. for 2 h. The reaction was cooled to RT, diluted with water and extracted with ethyl acetate. The combined organic layers were washed with brine, dried over Na$_2$SO$_4$, filtered and concentrated in vacuo to afford a residue, which was purified by pre-TLC (petroleum ether:ethyl acetate=5:1) to give the title compound. MS (EI) m/z 389 [M+H]$^+$.

Step 7: 1-(5-(3-Bromobenzamido)pyridin-2-yl)cyclobutane-1-carboxylic acid

To a solution of methyl 1-(5-(3-bromobenzamido)pyridin-2-yl)cyclobutanecarboxylate (200 mg, 0.514 mmol) in MeOH (3 mL), THF (3 mL) and water (1 mL) was added lithium hydroxide hydrate (65 mg, 1.5 mmol) at RT. The mixture was stirred at RT for 24 h. The reaction was diluted with water, adjusted to pH-3 with 3M HCl, extracted with ethyl acetate. The combined organic layers were washed with brine, dried over Na$_2$SO$_4$, filtered and concentrated in vacuo to afford the title compound, which was used directly in next step without further purification. MS (EI) m/z 375 [M+H]$^+$.

Step 8: N-(6-(1-((2-amino-5-(trifluoromethyl)pyridin-3-yl)carbamoyl)cyclobutyl)pyridin-3-yl)-3-bromobenzamide To a solution of 1-(5-(3-bromobenzamido)pyridin-2-yl) cyclobutanecarboxylic acid (100 mg, 0.267 mmol) in pyridine (5 mL) was added 5-(trifluoromethyl)pyridine-2,3-diamine (48 mg, 0.27 mmol) and EDC (153 mg, 0.800 mmol) at RT. After the addition was complete, the reaction mixture was stirred at 30° C. for 2 h. The reaction was cooled to RT, diluted with water, and extracted with ethyl acetate. The combined organic layers were washed with brine, dried over Na$_2$SO$_4$, filtered and concentrated in vacuo to afford the title compound, which was used directly in next step without further purification. MS (EI) m/z 534 [M+H]$^+$.

Step 9: 3-Bromo-N-(6-(1-(6-(trifluoromethyl)-1H-imidazo[4,5-b]pyridin-2-yl)cyclobutyl)pyridin-3-yl) benzamide A solution of N-(6-(1-((2-amino-5-(trifluoromethyl)pyridin-3-yl)carbamoyl)cyclobutyl)pyridin-3-yl)-3-bromobenzamide (130 mg, 0.243 mmol) in AcOH (1 mL) was stirred at 120° C. for 6 h. The reaction mixture was concentrated in vacuo. The residue was diluted with NH$_4$Cl (sat.) and extracted with ethyl acetate. The combined organic layers were washed with brine, dried over Na$_2$SO$_4$, filtered and concentrated in vacuo to afford a residue, which was purified by prep-TLC (petroleum ether:ethyl acetate=1:1) to give the title compound. MS (EI) m/z 516 [M+H]$^+$.

Step 10: 3-Cyano-N-(6-(1-(6-(trifluoromethyl)-1H-imidazo[4,5-b]pyridin-2-yl)cyclobutyl)pyridin-3-yl) benzamide (Ex. 45)

To a solution of 3-bromo-N-(6-(1-(6-(trifluoromethyl)-1H-imidazo[4,5-b]pyridin-2-yl)cyclobutyl)pyridin-3-yl) benzamide (30 mg, 0.058 mmol), dppf (4.0 mg, 7.2 µmol) and zinc (2.0 mg, 0.031 mmol) in DMA (1.5 mL) were added Zn(CN)$_2$ (10 mg, 0.085 mmol) and Pd$_2$(dba)$_3$ (3.0 mg, 3.3 µmol) at RT. After the addition was finished, the reaction mixture was irradiated in microwave at 150° C. for 1 h. The reaction mixture was cooled to RT, diluted with water and extracted with EtOAc. The combined organic layers were washed with brine, dried over Na$_2$SO$_4$, filtered and concentrated in vacuo to afford a residue, which was purified by reversed phase HPLC, eluting with water (0.1% TFA)-ACN to afford the title compound as a TFA salt (Ex. 45). $^1$H NMR (400 MHz, CD$_3$OD) δ 9.00 (d, J=2.2 Hz, 1H), 8.70 (s, 1H), 8.40-8.30 (m, 2H), 8.30-8.20 (m, 2H), 7.95 (d, J=7.7 Hz, 1H), 7.80-7.60 (m, 2H), 3.20-2.95 (m, 4H), 2.35-2.05 (m, 2H); MS (EI) m/z: 463 [M+H]+.

Example 46: N-(6-(1-(1H-benzo[d]imidazol-2-yl)cyclobutyl)pyridin-3-yl)-3-cyanobenzamide

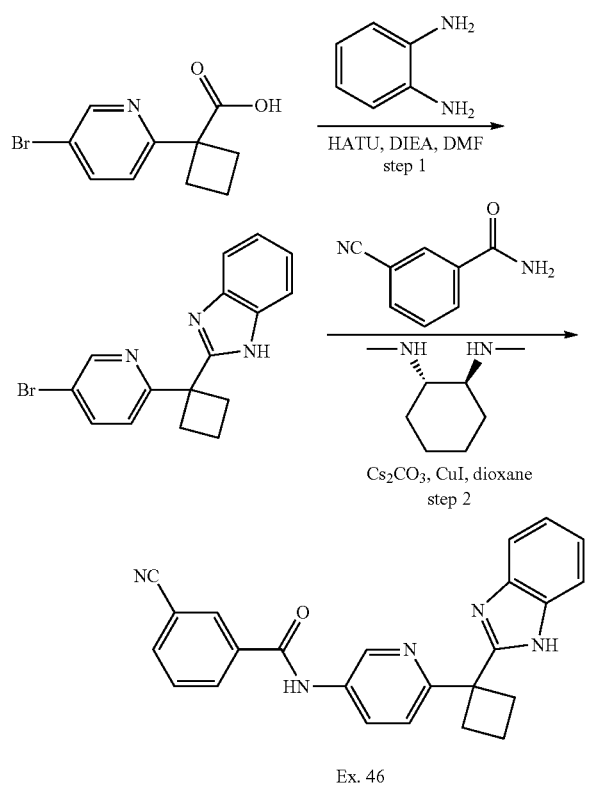

Ex. 46

Step 1: 2-(1-(5-Bromopyridin-2-yl)cyclobutyl)-1H-benzo[d]imidazole

To a vial was added 1-(5-bromopyridin-2-yl)cyclobutanecarboxylic acid (69.5 mg, 0.270 mmol), benzene-1,2-diamine (50 mg, 0.46 mmol), HATU (206 mg, 0.540 mmol), DMF (1360 μL) and DIEA (142 μL, 0.810 mmol). The mixture was stirred at 100° C. for 48 h. The mixture was diluted with NaHCO$_3$ (sat.) and extracted with ethyl acetate. The combined organic layers were washed with brine, dried over magnesium sulfate, filtered and concentrated in vacuo to afford a residue, which was purified by column chromatography on silica gel (EtOAc in hexane: 0-100% gradient) to afford the title compound. MS (EI) m/z 328 [M+H]+.

Step 2: N-(6-(1-(1H-benzo[d]imidazol-2-yl)cyclobutyl)pyridin-3-yl)-3-cyanobenzamide (Ex. 46)

To a vial equipped with a stir bar were added 2-(1-(5-bromopyridin-2-yl)cyclobutyl)-1H-benzo[d]imidazole (23.5 mg, 0.0720 mmol), cesium carbonate (70 mg, 0.22 mmol), 3-cyanobenzamide (10 mg, 0.070 mmol), (1S,2S)—N1,N2-dimethylcyclohexane-1,2-diamine (2.0 mg, 0.014 mmol), and dioxane (358 μL). The vial was purged with nitrogen, and copper (I) iodide (1.36 mg, 7.16 μmol) was added. The vial was purged with nitrogen for 3 minutes, then the vial was sealed and heated to 110° C. for 16 h. After 16 h the mixture was diluted with DMSO, filtered, and purified by reversed phase HPLC, eluting with water (0.1% TFA)-ACN to afford the title compound as a TFA salt (Ex. 46). $^1$H NMR (600 MHz, DMSO-d$_6$) δ 10.77 (s, 1H), 8.95 (s, 1H), 8.45 (s, 1H), 8.30 (dd, J=13.1, 8.4 Hz, 2H), 8.14 (d, J=7.6 Hz, 1H), 7.86-7.78 (m, 3H), 7.76 (d, J=8.6 Hz, 1H), 7.59-7.54 (m, 2H), 3.25-2.80 (m, 4H), 2.21-2.08 (m, 2H). MS (EI) m/z 394 [M+H]+.

Example 47: 3-Chloro-N-(6-(1-(6-cyano-1H-benzo[d]imidazol-2-yl)cyclobutyl)pyridin-3-yl)benzamide

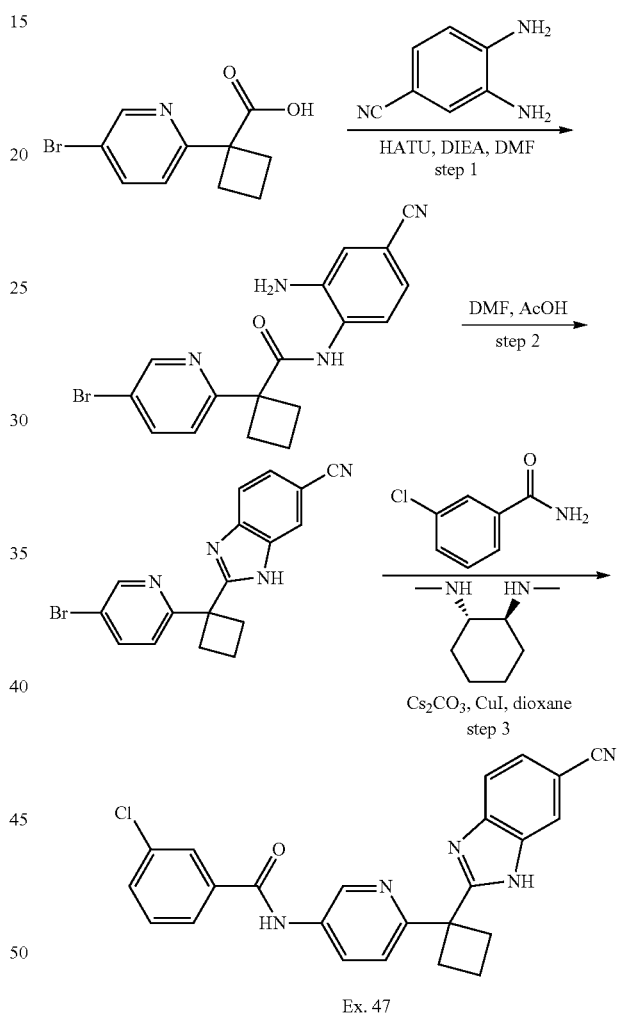

Ex. 47

Step 1: N-(2-amino-4-cyanophenyl)-1-(5-bromopyridin-2-yl)cyclobutane-1-carboxamide To a vial equipped with a stir bar were added 1-(5-bromopyridin-2-yl)cyclobutanecarboxylic acid (167 mg, 0.652 mmol), HATU (372 mg, 0.978 mmol) and DMF (6521 μL). The mixture was stirred for 5 min, then 3,4-diaminobenzonitrile (104 mg, 0.783 mmol) and DIEA (342 μL, 1.96 mmol) were added. The reaction was stirred at RT for 120 h. The mixture was diluted with NaHCO$_3$ (sat.) and extracted with ethyl acetate. The combined organic layers were washed with brine, dried over magnesium sulfate, filtered and concentrated in vacuo to afford the title compound, which was used in next step directly. MS (EI) m/z 371 [M+H]⁺.

Step 2: 2-(1-(5-Bromopyridin-2-yl)cyclobutyl)-1H-benzo[d]imidazole-6-carbonitrile To a vial equipped with a stir bar were added N-(2-amino-4-cyanophenyl)-1-(5-bromopyridin-2-yl)cyclobutanecarboxamide (240 mg, 0.646 mmol), DMF (2586 μL) and AcOH (646 μL). The mixture was heated to 130° C. for 24 h, then diluted with NaHCO₃ (sat.) and extracted with ethyl acetate. The combined organic layers were washed with brine, dried over magnesium sulfate, filtered and concentrated in vacuo to afford the title compound, which was used in next step directly. MS (EI) m/z 353 [M+H]⁺.

Step 3: 3-Chloro-N-(6-(1-(6-cyano-1H-benzo[d]imidazol-2-yl)cyclobutyl)pyridin-3-yl)benzamide (Ex. 47)

To a vial equipped with a stir bar were added 2-(1-(5-bromopyridin-2-yl)cyclobutyl)-1H-benzo[d]imidazole-6-carbonitrile (114 mg, 0.323 mmol), cesium carbonate (315 mg, 0.968 mmol), 3-chlorobenzamide (49.2 mg, 0.316 mmol), (1S,2S)—N1,N2-dimethylcyclohexane-1,2-diamine (9.2 mg, 0.065 mmol) and dioxane (1614 μL). The vial was purged with nitrogen, then copper (I) iodide (6.2 mg, 0.032 mmol) was added. The vial was purged with nitrogen for 3 min, then sealed and heated to 110° C. for 16 h. The mixture was filtered over Celite, rinsing with methanol. The filtrate was concentrated in vacuo to afford a residue, which was purified by reversed phase HPLC, eluting with water (0.1% TFA)-ACN to afford the title compound as a TFA salt (Ex. 47). ¹H NMR (600 MHz, DMSO-d₆) δ 10.62 (s, 1H), 8.97 (s, 1H), 8.20 (d, J=8.4 Hz, 1H), 8.11 (s, 1H), 8.06 (s, 1H), 7.96 (d, J=7.6 Hz, 1H), 7.72 (dd, J=19.0, 8.1 Hz, 2H), 7.66-7.60 (m, 2H), 7.41 (d, J=8.5 Hz, 1H), 3.04-2.96 (m, 2H), 2.97-2.88 (m, 2H), 2.14-1.92 (m, 2H). MS (EI) m/z 428 [M+H]⁺.

Example 48: 3-Chloro-N-(5-(1-(4,5,6,7-tetrahydro-1H-benzo[d]imidazol-2-yl)cyclobutyl)pyridin-2-yl)benzamide

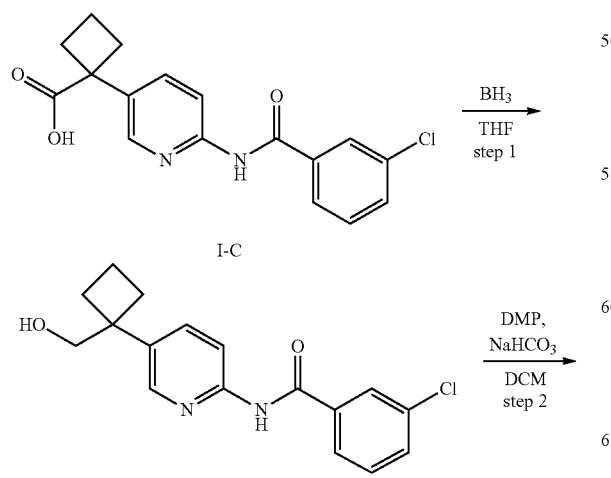

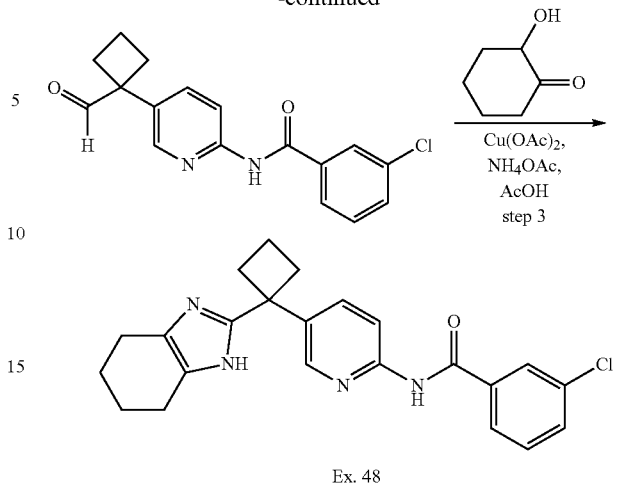

Ex. 48

Step 1: 3-Chloro-N-(5-(1-(hydroxymethyl)cyclobutyl)pyridin-2-yl)benzamide

To a stirred solution of I-C (500 mg, 1.51 mmol) in THF (5 mL) was added borane THF complex solution (1 M, 3.0 mL, 3.0 mmol) at 0° C. under N₂. After the addition was finished, the reaction was stirred from 0° C. to RT for 18 h. The solvent was concentrated in vacuo. The residue was purified by prep-TLC (petroleum ether:ethyl acetate=1:1) to give the title compound. MS (EI) m/z 317 [M+H]⁺.

Step 2: 3-Chloro-N-(5-(1-formylcyclobutyl)pyridin-2-yl)benzamide

To a stirred solution of 3-chloro-N-(5-(1-(hydroxymethyl)cyclobutyl)pyridin-2-yl)benzamide (190 mg, 0.600 mmol) in DCM (2 mL) were added NaHCO₃ (504 mg, 6.00 mmol) and DMP (382 mg, 0.900 mmol) at RT. The reaction was stirred at RT for 18 h. The reaction was diluted with water, and extracted with ethyl acetate. The combined organic layers were washed with brine, dried over Na₂SO₄, filtered and concentrated in vacuo to afford a residue, which was purified by prep-TLC (petroleum ether:ethyl acetate=2:1) to give the title compound. MS (EI) m/z 315 [M+H]⁺.

Step 3: 3-Chloro-N-(5-(1-(4,5,6,7-tetrahydro-1H-benzo[d]imidazol-2-yl)cyclobutyl)pyridin-2-yl)benzamide (Ex. 48)

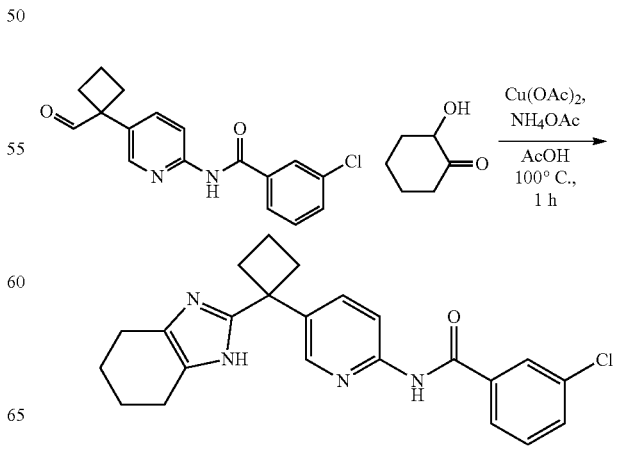

To a stirred solution of 3-chloro-N-(5-(1-formylcyclobutyl)pyridin-2-yl)benzamide (40 mg, 0.13 mmol) and 2-hydroxycyclohexanone (16 mg, 0.14 mmol) in AcOH (4 mL) was added Cu(OAc)$_2$ (46 mg, 0.25 mmol) and NH$_4$OAc (441 mg, 5.72 mmol) at RT. After the addition was finished, the reaction was stirred at 100° C. for 1 h. The reaction was cooled to RT. The solvent was removed in vacuo. The residue was diluted with water, and extracted with ethyl acetate. The combined organic layers were washed with brine, dried over Na$_2$SO$_4$, filtered and concentrated in vacuo to afford a residue, which was purified by reversed phase HPLC, eluting with water (0.1% TFA)-ACN to afford the title compound as a TFA salt (Ex. 48). $^1$H NMR (400 MHz, CDCl$_3$) δ 8.83 (s, 1H), 8.50 (d, J=9.2 Hz, 1H), 8.23 (d, J=7.0 Hz, 1H), 7.98 (s, 1H) 7.94 (d, J=7.4 Hz, 1H), 7.57 (d, J=7.9 Hz, 1H), 7.45-7.37 (m, 1H), 3.35-3.10 (m, 2H), 2.89-2.78 (m, 2H), 2.65-2.45 (m, 4H), 2.25-2.14 (m, 1H), 2.09 (dd, J=13.4, 4.6 Hz, 1H), 1.85-1.70 (m, 4H). MS (ESI) m/z: 407 [M+H]$^+$.

Biological Assays

IDO1 Cellular Assay in HeLa Cells Stimulated with IFNγ

HeLa cells were cultured in complete HeLa culture medium (90% EMEM, 10% heat-inactivated fetal bovine serum) and expanded to about 1×10$^9$ cells. The cells were then collected and frozen down at 1×10$^7$ cells/vial in 1 mL frozen medium (90% complete HeLa culture medium, 10% DMSO).

Compounds to be tested were serially diluted in ten 3-fold steps in DMSO starting from 10 mM DMSO stocks in Echo low volume plate(s). Compound dilutions or DMSO alone were then dispensed from the dilution plate(s) into Greiner black 384-well assay plate(s) (catalog #781086, 50 nL/well) using an Echo 550 acoustic liquid handler (Labcyte).

Frozen HeLa cells were thawed and transferred into HeLa assay medium (99% complete HeLa culture medium, 1% Pen/Strep) with 20 mL medium/vial of cells. The cells were spun down at 250 g in a table top centrifuge for 5 min and suspended in same volume of HeLa assay medium. The cells were then counted and adjusted to a density of 2×10$^5$ cells/mL in HeLa assay medium. Sterile L-tryptophan were added to the cells with final concentration of 300 uM L-tryptophan. A small aliquot (2 mL/plate) of HeLa cells were set aside and were not treated with IFNγ, to serve as the Max-E control. The rest of HeLa cells were added with sterile IFNγ (Cat #285-IF, R & D systems) with a final concentration of 100 ng/mL.

HeLa cells with and without IFNγ were dispensed to the respective wells of 384-well assay plates containing the compounds. The plates were incubated for about 48 hours at a 37° C., 5% CO$_2$ incubator. Afterwards, 12 µL of 0.5 M methyl isonipecotate in dimethyl sulfoxide were added into each well and the plates were sealed and incubated at 37° C. without CO$_2$ overnight. The plates were centrifuged for 1 min at 200×g. The resulting fluorescence was measured in a Spectramax plate reader (Molecular Devices) with a 400 nm excitation filter and a 510 nm emission filter.

The fluorescence intensity of each well was corrected for the background observed in wells with non-IFNγ-treated cells and was expressed as a fraction of the intensity observed in wells of IFNγ-treated cells and DMSO only. Potencies were calculated by linear least squares fit to the four parameter logistic IC$_{50}$ equation.

The biological activity data using the IDO1 cellular assay described above are summarized in the table below. Compounds disclosed herein generally have IC$_{50}$ of about 0.1 nM to about 20,000 nM, or more specifically, about 1 nM to about 10,000 nM, or more specifically, about 5 nM to about 5,000 nM, or more specifically, about 10 nM to about 1,000 nM, or still more specifically, about 10 nM to about 500 nM. Specific IC$_{50}$ activity data for the exemplified compounds disclosed herein is provided in the following table.

| Ex. # | IDO1 HeLa Cell Assay, IC$_{50}$, nM |
|---|---|
| Ex. 1 | 10.1 |
| Ex. 2 | 13.56 |
| Ex. 3 | 6.874 |
| Ex. 4 | 144.1 |
| Ex. 5 | 12.51 |
| Ex. 6 | 632.8 |
| Ex. 7 | 5.662 |
| Ex. 8 | 4.69 |
| Ex. 9 | 5.1 |
| Ex. 10 | 5.229 |
| Ex. 11 | 10.22 |
| Ex. 12 | 432.9 |
| Ex. 13 | 2.787 |
| Ex. 14 | 5.625 |
| Ex. 15 | 10.07 |
| Ex. 16 | 7.767 |
| Ex. 17 | 4.897 |
| Ex. 18 | 131.6 |
| Ex. 19 | 2.423 |
| Ex. 20 | 262 |
| Ex. 21 | 1.888 |
| Ex. 22 | 14.14 |
| Ex. 23 | 7.669 |
| Ex. 24 | 6.654 |
| Ex. 25 | 7.211 |
| Ex. 26 | 9.659 |
| Ex. 27 | 3.465 |
| Ex. 28 | 23.55 |
| Ex. 29 | 45.98 |
| Ex. 30 | 6.575 |
| Ex. 31 | 199.7 |
| Ex. 32 | 5.397 |
| Ex. 33 | 20.67 |
| Ex. 34 | 24.76 |
| Ex. 35 | 383.3 |
| Ex. 36 | 10000 |
| Ex. 37 | 5.376 |
| Ex. 38 | 2.179 |
| Ex. 39 | 121.1 |
| Ex. 40 | 94.84 |
| Ex. 41 | 263.3 |
| Ex. 42 | 5910 |
| Ex. 43 | 3860 |
| Ex. 44 | 6218 |
| Ex. 45 | 4.982 |
| Ex. 46 | 6.115 |
| Ex. 47 | 2.261 |
| Ex. 48 | 99.71 |

IDO1 Human Whole Blood Assay

Compounds to be tested were serially diluted in ten 3-fold steps in DMSO starting from 10 mM. 3 µL of compound dilutions or DMSO alone were then dispensed from the dilution plate into a polypropylene 96-well assay plate containing 97 µL of RPMI medium using an Echo 555 acoustic liquid handler (Labcyte). LPS and IFNγ was prepared in RPMI medium to a 10× of final conc. (1000 ng/mL), final concentration is 100 ng/mL.

Human whole blood was drawn in sodium heparin coated tubes from healthy internal donors. 240 µL of blood was transferred to each of the wells of a v-bottom 96 well plate. 30 µL of compound was transferred from intermediate dilution plate, and incubated for 15 min. 30 µL from stimulants was then transferred to blood and mixed thoroughly. Plate was covered with breathable membrane and incubated at 37° C. for overnight (18 h).

On day 2, isotope labeled standard solutions of kunurenine and tryptophan was made in water at 10× concentration and 30 μL was added to the blood at 3 μfinal concentration. The assay plates were centrifuged at 300×G for 10 min with no brake to separate plasma from red blood cells. 60 μL of plasma samples was removed without disturbing red blood cells. Plasma was diluted with RPMI in 1:1 ratio and proteins were precipitated out with two volumes of Acetonitrile. The plates were centrifuged at 4000×G for 60 min. 20 μL of supernatant was carefully transferred to a 384 well plate containing 40 μL of 0.1% formic acid in water and analyzed by LC/MS/MS.

LC/MS/MS analyses were performed using Thermo Fisher's LX4-TSQ Quantum Ultra system. This system consists of four Agilent binary high-performance liquid chromatography (HPLC) pumps and a TSQ Quantum Ultra triple quadrupole MS/MS instrument. For each sample, 5 μL were injected onto an Atlantis T3 column (2.1 mm×150 mm, 3 μm particle size) from Waters. The mobile phase gradient pumped at 0.8 mL/min was used to elute the analytes from the column at 25° C. The elution started at 0% B increasing linearly to 25% B at 6.5 min, holding at 25% for 1 min, re-equilibrating to 10 min. Mobile phase A consisted of 0.1% formic acid in water. Mobile phase B consisted of 0.1% of formic acid in acetonitrile. Data was acquired in positive mode using a HESI interface. The operational parameters for the TSQ Quantum Ultra instrument were a spray voltage of 4000 V, capillary temperature of 380° C., vaporizer temperature 400° C., sheath gas 60 arbitrary units, Aux gas 20 arbitrary units, tube lens 85 and collision gas 1.2 mTorr. SRM chromatograms of kynurenine (QI: 209.2>Q3:94.0) and internal standard (QI: 215.3>Q3:98.2) were collected for 90 sec. The peak area was integrated by Xcalibur Quan software. The ratios between the kynurenine generated in the reaction and 2D6-Kynurenine spiked-in internal standard were used to generate percentage inhibition and $IC_{50}$ values. Compounds were titrated and $IC_{50}$'s were calculated by 4 parameter sigmoidal curve fitting formula.

The biological activity data of selective compounds using the IDO1 human whole blood assay described above are summarized in the table below.

| Ex. # | IDO1 human whole blood assay, $IC_{50}$, nM |
|---|---|
| Ex. 1 | 158.7 |
| Ex. 2 | 386.7 |
| Ex. 3 | 428.7 |
| Ex. 5 | 863.5 |
| Ex. 7 | 272.7 |
| Ex. 8 | 493.1 |
| Ex. 9 | 504.2 |
| Ex. 10 | 501.4 |
| Ex. 13 | 125.4 |
| Ex. 16 | 889.4 |
| Ex. 17 | 828.8 |
| Ex. 19 | 278.8 |
| Ex. 21 | 80.87 |
| Ex. 23 | 1068 |
| Ex. 24 | 825.8 |
| Ex. 25 | 690.7 |
| Ex. 27 | 496.1 |
| Ex. 28 | 2285 |
| Ex. 30 | 311.9 |
| Ex. 32 | 446 |
| Ex. 33 | 1599 |
| Ex. 34 | 3294 |
| Ex. 37 | 58.23 |
| Ex. 38 | 220 |
| Ex. 45 | 5779 |
| Ex. 46 | 1692 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:
1. A compound of formula (I), or a pharmaceutically acceptable salt thereof:

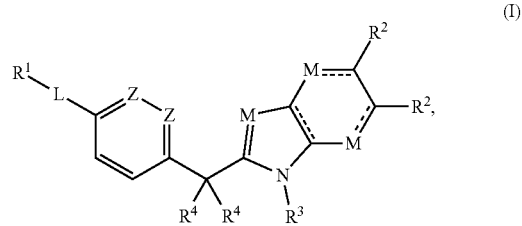

wherein:
L is selected from (1) —NHC(O)— and (2) —C(O)NH—;
=M- is =N—;
each occurrence of =M- is independently selected from (1)=$CR^a$—, (2) —$CR^aR^a$— and (3)=N—;
  wherein each occurrence of $R^a$ is independently selected from:
  (a) H,
  (b) —OH,
  (c) halogen,
  (d) —CN,
  (e) $C_{1-6}$ alkyl,
  (f) —O—$C_{1-6}$ alkyl,
  (g) —C(O)—$R^5$, wherein $R^5$ is selected from (a) —OH, (b) —O—$C_{1-6}$ alkyl and (c) a 5- or 6-membered heterocyclyl, optionally substituted with —OH, and
  (h) 5- or 6-membered heteroaryl;
  wherein each of the $C_{1-6}$ alkyl of (e) and (f) is optionally substituted with 1 to 3 substituents independently selected from (a) —OH, (b) —C(O)OH and (c) halogen;
each dotted bond "═" is independently selected from (1) a double bond and (2) a single bond;
one Z is =CH— and the other Z is =N—;
$R^1$ is selected from:
  (1) $C_{1-6}$ alkyl,
  (2) $C_{3-6}$ cycloalkyl,
  (3) aryl and
  (4) 5- or 6-membered heteroaryl;
  wherein each of the aryl of (3) and the heteroaryl of (4) is optionally substituted with 1 to 3 substituents independently selected from (a) halogen, (b) —CN, (c) —$NH_2$, (d) $C_{1-6}$ alkyl, optionally substituted with 1 to 3 halogens, (e) —O—$C_{1-6}$ alkyl and (f) $C_{3-6}$ cycloalkyl;
each occurrence of $R^2$ is independently selected from:
  (1) H,
  (2) —OH,
  (3) halogen,
  (4) —CN,
  (5) $C_{1-6}$ alkyl,
  (6) —O—$C_{1-6}$ alkyl,
  (7) —C(O)—$R^5$, wherein $R^5$ is selected from (a) —OH, (b) —O—$C_{1-6}$ alkyl and (c) a 5- or 6-membered heterocyclyl, optionally substituted with —OH, and (8) 5- or 6-membered heteroaryl;
wherein each of the $C_{1-6}$ alkyl of (5) and (6) is optionally substituted with 1 to 3 substituents independently selected from (a) —OH, (b) —C(O)OH and (c) halogen;
or alternatively, two adjacent $R^2$ groups together with the carbons to which they are attached form a 5- or 6-membered heterocyclic ring comprising 1 to 2 hetero atoms independently selected from O, S and NH, wherein the 5- or 6-membered heterocyclic ring is optionally substituted with an oxo;
$R^3$ is selected from (1) H and (2) $C_{1-6}$ alkyl optionally substituted with a halogen or —OH; and
one $R^4$ is H and the other $R^4$ is selected from (1) —OH, (2) $C_{1-6}$ alkyl and (3) —O—$C_{1-6}$ alkyl;
or alternatively, two $R^4$ groups together with the carbon to which they are attached form a 3-5 membered cycloalkyl ring or a 4-5 membered heterocyclic ring containing one oxygen atom; each ring is optionally substituted with —OH, halogen or $C_{1-6}$ alkyl.

2. The compound of claim 1, or a pharmaceutically acceptable salt thereof, of formula (Ia):

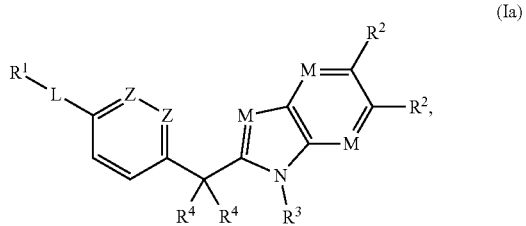

(Ia)

wherein:
the =M- in the five membered ring is =N— and each occurrence of the other two =M- is independently selected from (1)=$CR^a$— and (2)=N—;
$R^1$ is selected from:
(1) $C_{1-6}$ alkyl,
(2) $C_{3-6}$ cycloalkyl,
(3) phenyl and
(4) pyridinyl;
wherein each of the aryl of (3) and the pyridinyl of (4) is optionally substituted with 1 to 3 substituents independently selected from (a) halogen, (b) —CN, (c) —NH$_2$, (d) —CH$_3$, (e) —CF$_3$, (f) —O—CH$_3$ and (g) $C_{3-6}$ cycloalkyl;
each occurrence of $R^2$ is independently selected from:
(1) H,
(2) —OH,
(3) halogen,
(4) —CN,
(5) $C_{1-6}$ alkyl,
(6) —O—$C_{1-6}$ alkyl,
(7) —C(O)—$R^5$, wherein $R^5$ is selected from (a) —OH, (b) —O—$C_{1-6}$ alkyl and (c) a 5- or 6-membered heterocyclyl, optionally substituted with —OH, and
(8) 5- or 6-membered heteroaryl;
wherein each of the $C_{1-6}$ alkyl of (5) and (6) is optionally substituted with 1 to 3 substituents independently selected from (a) —OH, (b) —C(O)OH and (c) halogen or alternatively, two adjacent $R^2$ groups together with the carbons to which they are attached form a 5- or 6-membered heterocyclic group comprising 1 to 2 hetero atoms independently selected from O, S and N, wherein the 5- or 6-membered heterocyclic group is optionally substituted with an oxo;
$R^3$ is selected from (1) H and (2) $C_{1-6}$ alkyl optionally substituted with a halogen or —OH; and
one $R^4$ is H and the other $R^4$ is selected from (1) —OH, (2) $C_{1-4}$ alkyl and (3) —O—$C_{1-4}$ alkyl;
or alternatively, two $R^4$ groups together with the carbon to which they are attached form a cyclobutyl ring or an oxetanyl ring; each ring is optionally substituted with —OH, halogen or $C_{1-6}$ alkyl.

3. The compound of claim 1, or a pharmaceutically acceptable salt thereof, of formula (Ib):

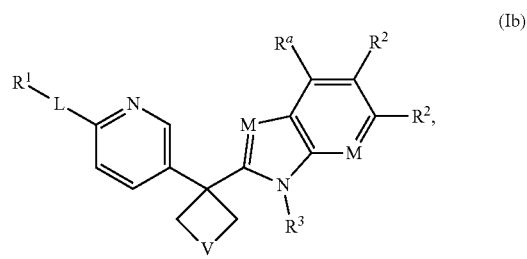

(Ib)

wherein:
L is selected from (1) —NHC(O)— and (2) —C(O)NH—;
the =M- in the five membered ring is =N— and the other =M- is selected from (1)=$CR^a$— and (2) =N—;
V is selected from (1) —$CR^bR^b$—, (3) —O—; wherein each occurrence of $R^b$ is independently selected from (a) H, (b) —OH, (c) halogen and (d) $C_{1-6}$ alkyl;
$R^1$ is selected from:
(1) $C_{1-6}$ alkyl,
(2) $C_{3-6}$ cycloalkyl,
(3) aryl and
(4) 5- or 6-membered heteroaryl;
wherein each of the aryl of (3) and the heteroaryl of (4) is optionally substituted with 1 to 3 substituents independently selected from (a) halogen, (b) —CN, (c) —CF$_3$, (d) —NH$_2$, (e) $C_{1-6}$ alkyl and (f) $C_{3-6}$ cycloalkyl;
each occurrence of $R^2$ is independently selected from:
(1) H,
(2) —OH,
(3) halogen,
(4) —CN,
(5) $C_{1-6}$ alkyl,
(6) —O—$C_{1-6}$ alkyl, and
(7) 5- or 6-membered heteroaryl;
wherein each of the $C_{1-6}$ alkyl of (5) and (6) is optionally substituted with 1 to 3 substituents independently selected from (a) —OH, (b) —C(O)OH and (c) halogen;
or alternatively, two adjacent $R^2$ groups together with the carbons to which they are attached form a 5- or 6-membered heterocyclic group which is optionally substituted with an oxo; and
$R^3$ is selected from (1) H and (2) $C_{1-6}$ alkyl optionally substituted with halogen or —OH.

4. The compound of claim 3, or a pharmaceutically acceptable salt thereof, wherein:
L is selected from (1) —NHC(O)— and (2) —C(O)NH—;
V is selected from (1) a bond and (2) —$CR^bR^b$—; wherein each occurrence of $R^b$ is independently selected from (a) H, (b) —OH, (c) halogen and (d) $C_{1-6}$ alkyl;

$R^1$ is selected from (1) $C_{1-6}$ alkyl, (b) $C_{3-6}$ cycloalkyl, (c) aryl and (d) 5- or 6-membered heteroaryl;

wherein each of the aryl of (c) and the heteroaryl of (d) is optionally substituted with 1 to 3 substituents independently selected from (a) halogen, (b) —CN, (c) —CF$_3$, (d) —NH$_2$, (e) $C_{1-6}$ alkyl and (f) $C_{3-6}$ cycloalkyl;

each occurrence of $R^2$ is independently selected from (1) H, (2) —OH, (3) halogen, (4) —CN, (5) $C_{1-6}$ alkyl, (6) —O—$C_{1-6}$ alkyl and (7) 5- or 6-membered heteroaryl; wherein each of the $C_{1-6}$ alkyl of (5) and (6) is optionally substituted with 1 to 3 substituents independently selected from (a) —OH and (b) halogen;

or alternatively, two adjacent $R^2$ groups together with the carbons to which they are attached form a 5- or 6-membered heterocyclic group which is optionally substituted with an oxo; and $R^3$ is selected from H and $C_{1-6}$ alkyl optionally substituted with halogen or —OH.

5. The compound of claim 4, or a pharmaceutically acceptable salt thereof, wherein:

each M is =N—;

V is a bond or —CR$^b$R$^b$—; wherein each occurrence of R$^b$ is independently selected from (a) H, (b) —OH, (c) halogen and (d) $C_{1-6}$ alkyl;

$R^1$ is selected from (1) $C_{1-6}$ alkyl, (2) $C_{3-6}$ cycloalkyl, (3) aryl and (4) 5- or 6-membered heteroaryl;

wherein each of the aryl of (3) and the heteroaryl of (4) is optionally substituted with 1 to 3 substituents independently selected from (a) halogen, (b) —CN, (c) —CF$_3$, (d) —NH$_2$, (e) $C_{1-6}$ alkyl and (f) $C_{3-6}$ cycloalkyl;

each occurrence of $R^2$ is independently selected from (1) H, (2)halogen, (3) —CN and (4) $C_{1-6}$ alkyl;

wherein the $C_{1-6}$ alkyl is optionally substituted with 1 to 3 halogens; and $R^3$ is selected from (1) H and (2) $C_{1-6}$ alkyl optionally substituted with —OH.

6. The compound of claim 4, or a pharmaceutically acceptable salt thereof, wherein:

the =M- in the five membered ring is =N— and the other =M- is =CR$^a$—;

V is a bond or CR$^b$R$^b$; wherein each occurrence of R$^b$ is independently selected from (a) H, (b) —OH, (c) halogen and (d) $C_{1-6}$ alkyl;

$R^1$ is selected from (1) $C_{1-6}$ alkyl, (2) $C_{3-6}$ cycloalkyl, (3) aryl and (4) 5- or 6-membered heteroaryl;

wherein each of the aryl of (3) and the heteroaryl of (4) is optionally substituted with 1 to 3 substituents independently selected from (a) halogen, (b) —CN, (c) —CF$_3$, (d) —NH$_2$, (e) $C_{1-6}$ alkyl and (f) $C_{3-6}$ cycloalkyl;

each occurrence of $R^2$ is independently selected from (1) H, (2)halogen, (3) —CN and (4) $C_{1-6}$ alkyl;

wherein the $C_{1-6}$ alkyl is optionally substituted with 1 to 3 halogens; and $R^3$ is H.

7. The compound of claim 1, or a pharmaceutically acceptable salt thereof, of formula (Ic):

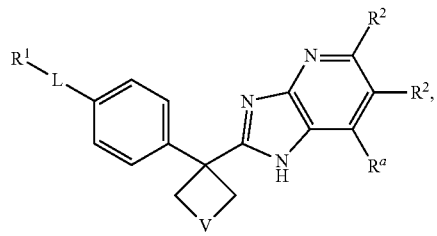

(Ic)

wherein:

L is selected from (1) —NHC(O)— and (2) —C(O)NH—;

V is selected from (1) a bond and (2) —CR$^b$R$^b$ wherein each occurrence of R$^b$ is independently selected from (a) H, (b) —OH, (c) halogen and (d) $C_{1-6}$ alkyl;

$R^1$ is selected from (1) $C_{1-6}$ alkyl, (2) $C_{3-6}$ cycloalkyl, (3) aryl and (4) 5- or 6-membered heteroaryl;

wherein each of the aryl of (3) and the heteroaryl of (4) is optionally substituted with 1 to 3 substituents independently selected from (a) halogen, (b) —CN, (c) —CF$_3$, (d) —NH$_2$, (e) $C_{1-6}$ alkyl and (f) $C_{3-6}$ cycloalkyl; and each occurrence of $R^2$ is independently selected from (1) H, (2) —OH, (3) halogen, (4) —CN, (5) $C_{1-6}$ alkyl, (6) —O—$C_{1-6}$ alkyl and (7) 5- or 6-membered heteroaryl; wherein each of the $C_{1-6}$ alkyl of (5) and (6) is optionally substituted with 1 to 3 substituents independently selected from (a) —OH and (b) halogen;

or alternatively, two adjacent $R^2$ groups together with the carbons to which they are attached form a 5- or 6-membered heterocyclic group which is optionally substituted with an oxo.

8. The compound of claim 7, or a pharmaceutically acceptable salt thereof, wherein:

L is selected from (1) —NHC(O)— and (2) —C(O)NH—;

V is selected from (1) —CH$_2$— and (3) —CF$_2$—;

$R^1$ is selected from (1) $C_{3-6}$ cycloalkyl, (2)aryl and (3) 5- or 6-membered heteroaryl; wherein each of the aryl of (2) and the heteroaryl of (3) is optionally substituted with 1 to 3 substituents independently selected from (a) halogen, (b) —CN, (c) —CF$_3$, (d) $C_{1-6}$ alkyl and (e) $C_{3-6}$ cycloalkyl; and each occurrence of $R^2$ is independently selected from (1) H, (2) —OH, (3) halogen, (4) —CN, (5) $C_{1-6}$ alkyl, (6) —O—$C_{1-6}$ alkyl and (7) tetrazolyl; wherein each of the $C_{1-6}$ alkyl is optionally substituted with 1 to 3 substituents independently selected from (a) —OH and (b) halogen.

9. The compound of claim 8, or a pharmaceutically acceptable salt thereof, wherein:

$R^1$ is selected from (1) phenyl and (2)pyridinyl; wherein each of the phenyl and the pyridinyl is optionally substituted with 1 to 3 substituents independently selected from (a) halogen, (b) —CN, (c) —CF$_3$ and (d) $C_{1-6}$ alkyl; and each occurrence of $R^2$ is independently selected from (1) H, (2)halogen, (3) —CN, (4) $C_{1-6}$ alkyl and (5) —O—$C_{1-6}$ alkyl; wherein each of the $C_{1-6}$ alkyl is optionally substituted with 1 to 3 substituents independently selected from (a) —OH and (b) halogen.

10. The compound of claim 1, or a pharmaceutically acceptable salt thereof, of formula (Id):

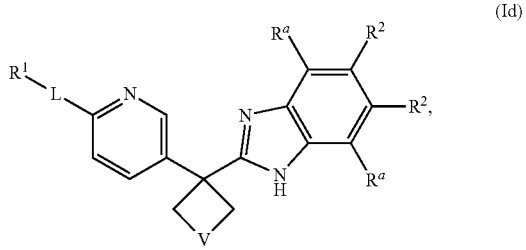

wherein:
L is selected from (1) —NHC(O)— and (2) —C(O)NH—;
V is selected from (1) a bond and (2) —CR$^b$R$^b$; wherein each occurrence of R$^b$ is independently selected from (a) H, (b) —OH, (c) halogen and (d) C$_{1-6}$ alkyl;
R$^1$ is selected from (1) C$_{1-6}$ alkyl, (2) C$_{3-6}$ cycloalkyl, (3) aryl and (4) 5- or 6-membered heteroaryl;
   wherein each of the aryl of (3) and the heteroaryl of (4) is optionally substituted with 1 to 3 substituents independently selected from (a) halogen, (b) —CN, (c) —CF$_3$, (d) —NH$_2$, (e) C$_{1-6}$ alkyl and (f) C$_{3-6}$ cycloalkyl; and
each occurrence of R$^2$ is independently selected from (1) H, (2) —OH, (3) halogen, (4) —CN, (5) C$_{1-6}$ alkyl, (6) —O—C$_{1-6}$ alkyl and (7) 5- or 6-membered heteroaryl; wherein each of the C$_{1-6}$ alkyl is optionally substituted with 1 to 3 substituents independently selected from (a) —OH and (b) halogen;
or alternatively, two adjacent R$^2$ groups together with the carbons to which they are attached form a 5- or 6-membered heterocyclic group which is optionally substituted with an oxo.

11. The compound of claim 10, or a pharmaceutically acceptable salt thereof, wherein:
L is selected from (1) —NHC(O)— and (2) —C(O)NH—;
V is selected from (1) —CH$_2$— and (3) —CF$_2$—;
R$^1$ is selected from (1) C$_{3-6}$ cycloalkyl, (2)aryl and (3) 5- or 6-membered heteroaryl; wherein each of the aryl of (2) and the heteroaryl of (3) is optionally substituted with 1 to 3 substituents independently selected from (a) halogen, (b) —CN, (c) —CF$_3$, (d) C$_{1-6}$ alkyl and (e) C$_{3-6}$ cycloalkyl; and
each occurrence of R$^2$ is independently selected from (1) H, (2) —OH, (3) halogen, (4) —CN, (5) C$_{1-6}$ alkyl, (6) —O—C$_{1-6}$ alkyl and (7) tetrazolyl; wherein each of the C$_{1-6}$ alkyl is optionally substituted with 1 to 3 substituents independently selected from (a) —OH and (b) halogen.

12. The compound of claim 11, or a pharmaceutically acceptable salt thereof, wherein:
R$^1$ is selected from (1) phenyl and (2)pyridinyl; wherein the phenyl and the pyridinyl is optionally substituted with 1 to 3 substituents independently selected from (a) halogen, (b) —CN, (c) —CF$_3$ and (d) C$_{1-6}$ alkyl; and
each occurrence of R$^2$ is independently selected from (1) H, (2)halogen, (3) —CN, (4) C$_{1-6}$ alkyl and (5) —O—C$_{1-6}$ alkyl; wherein each of the C$_{1-6}$ alkyl is optionally substituted with 1 to 3 substituents independently selected from (a) —OH and (b) halogen.

13. The compound of claim 1, or a pharmaceutically acceptable salt thereof, selected from the group consisting of:
N-(5-(1-(6-bromo-1H-imidazo[4,5-b]pyridin-2-yl)cyclobutyl)pyridin-2-yl)-3-chlorobenzamide,
3-chloro-N-(5-(1-(6-cyano-1H-imidazo[4,5-b]pyridin-2-yl)cyclobutyl)pyridin-2-yl)benzamide,
N-(5-(1-(1H-benzo[d]imidazol-2-yl)cyclobutyl)pyridin-2-yl)-3-chlorobenzamide,
N-(5-(1-(6-cyano-1H-imidazo[4,5-b]pyridin-2-yl)cyclobutyl)pyridin-2-yl)-5-fluoronicotinamide,
3-Cyano-N-(5-(1-(5-cyano-1H-benzo[d]imidazol-2-yl)cyclobutyl)pyridin-2-yl)benzamide,
3-chloro-N-(5-(1-(5-cyano-1H-pyrrolo[2,3-b]pyridin-2-yl)cyclobutyl)pyridin-2-yl)benzamide,
3-chloro-N-(5-{1-[6-(trifluoromethyl)-1H-imidazo[4,5-b]pyridin-2-yl]cyclobutyl}pyridin-2-yl)benzamide,
3-chloro-N-{5-[1-(5,7-dimethyl-1H-benzimidazol-2-yl)cyclobutyl]pyridin-2-yl}benzamide,
3-chloro-N-{5-[1-(5-chloro-7-methyl-1H-benzimidazol-2-yl)cyclobutyl]pyridin-2-yl}benzamide,
3-chloro-N-{5-[1-(6,7-dimethyl-1H-benzimidazol-2-yl)cyclobutyl]pyridin-2-yl}benzamide,
3-chloro-N-{5-[1-(7-methyl-1H-benzimidazol-2-yl)cyclobutyl]pyridin-2-yl}benzamide,
N-{5-[1-(6-tert-butyl-1H-benzimidazol-2-yl)cyclobutyl]pyridin-2-yl}-3-chlorobenzamide,
3-chloro-N-{5-[1-(6-methyl-1H-benzimidazol-2-yl)cyclobutyl]pyridin-2-yl}benzamide,
3-chloro-N-{5-[1-(6-methoxy-1H-benzimidazol-2-yl)cyclobutyl]pyridin-2-yl}benzamide,
3-chloro-N-{5-[1-(4-methoxy-1H-benzimidazol-2-yl)cyclobutyl]pyridin-2-yl}benzamide,
3-chloro-N-{5-[1-(5,6-difluoro-1H-benzimidazol-2-yl)cyclobutyl]pyridin-2-yl}benzamide,
3-chloro-N-{5-[1-(5,7-difluoro-1H-benzimidazol-2-yl)cyclobutyl]pyridin-2-yl}benzamide,
3-chloro-N-{5-[1-(7-oxo-3,6,7,8-tetrahydroimidazo[4,5-g][1,4]benzoxazin-2-yl)cyclobutyl]pyridin-2-yl}benzamide,
3-chloro-N-(5-{1-[6-(trifluoromethyl)-1H-benzimidazol-2-yl]cyclobutyl}pyridin-2-yl)benzamide,
3-chloro-N-(5-{1-[5-(1H-tetrazol-1-yl)-1H-benzimidazol-2-yl]cyclobutyl}pyridin-2-yl) benzamide,
3-chloro-N-{5-[1-(6-chloro-1H-benzimidazol-2-yl)cyclobutyl]pyridin-2-yl}benzamide,
3-chloro-N-(5-{1-[6-(trifluoromethoxy)-1H-benzimidazol-2-yl]cyclobutyl}pyridin-2-yl) benzamide,
3-chloro-N-(5-{1-[6-(difluoromethoxy)-1H-benzimidazol-2-yl]cyclobutyl}pyridin-2-yl) benzamide,
3-chloro-N-(5-{1-[7-(hydroxymethyl)-1H-benzimidazol-2-yl]cyclobutyl}pyridin-2-yl) benzamide,
3-chloro-N-{5-[1-(7-fluoro-1H-benzimidazol-2-yl)cyclobutyl]pyridin-2-yl}benzamide,
3-chloro-N-{5-[1-(5,6-dimethyl-1H-benzimidazol-2-yl)cyclobutyl]pyridin-2-yl}benzamide,
3-chloro-N-{5-[1-(6-fluoro-5-methyl-1H-benzimidazol-2-yl)cyclobutyl]pyridin-2-yl}benzamide,
3-cyano-N-(5-{1-[6-(trifluoromethyl)-3H-imidazo[4,5-b]pyridin-2-yl]cyclobutyl}pyridin-2-yl)benzamide,
3-cyano-N-{5-[1-(6-cyano-3H-imidazo[4,5-b]pyridin-2-yl)cyclobutyl]pyridin-2-yl}benzamide,
N-{5-[1-(5-chloro-1H-benzimidazol-2-yl)cyclobutyl]pyridin-2-yl}-3-cyanobenzamide,
3-Chloro-N-(5-(1-(1-(2-hydroxyethyl)-1H-benzo[d]imidazol-2-yl)cyclobutyl)pyridin-2-yl)benzamide,
3-Chloro-N-(5-(1-(7-(3-hydroxypropyl)-1H-benzo[d]imidazol-2-yl)cyclobutyl)pyridin-2-yl)benzamide,
2-(2-(1-(6-(3-Chlorobenzamido)pyridin-3-yl)cyclobutyl)-1H-benzo[d]imidazol-7-yl)acetic acid,
3-Cyano-N-(5-(1-(7-(2-hydroxyethyl)-1H-benzo[d]imidazol-2-yl)cyclobutyl) pyridin-2-yl)benzamide,
methyl 2-(1-(6-(3-cyanobenzamido)pyridin-3-yl)cyclobutyl)-1H-benzo[d]imidazole-7-carboxylate, 2-(1-(6-(3-Cyanobenzamido)pyridin-3-yl)cyclobutyl)-1H-benzo[d]imidazole-7-carboxylic acid,
3-Cyano-N-(5-(1-(7-(4-hydroxypiperidine-1-carbonyl)-1H-benzo[d]imidazol-2-yl)cyclobutyl)pyridin-2-yl) benzamide,
3-cyano-N-(5-{1-[7-(pyrrolidine-1-carbonyl)-1H-benzimidazol-2-yl]cyclobutyl}pyridin-2-yl)benzamide,
3-Cyano-N-(5-(methoxy(6-(trifluoromethyl)-3H-imidazo[4,5-b]pyridin-2-yl)methyl)pyridin-2-yl)benzamide,
(S)-3-cyano-N-(5-(methoxy(6-(trifluoromethyl)-3H-imidazo[4,5-b]pyridin-2-yl)methyl)pyridin-2-yl)benzamide,
(R)-3-cyano-N-(5-(methoxy(6-(trifluoromethyl)-3H-imidazo[4,5-b]pyridin-2-yl)methyl)pyridin-2-yl)benzamide,
3-cyano-N-(5-(hydroxy(6-(trifluoromethyl)-3H-imidazo[4,5-b]pyridin-2-yl)methyl)pyridin-2-yl)benzamide,
(S)-3-cyano-N-(5-(hydroxy(6-(trifluoromethyl)-3H-imidazo[4,5-b]pyridin-2-yl)methyl)pyridin-2-yl)benzamide,
(R)-3-cyano-N-(5-(hydroxy(6-(trifluoromethyl)-3H-imidazo[4,5-b]pyridin-2-yl)methyl)pyridin-2-yl)benzamide,
3-Cyano-N-(6-(1-(6-(trifluoromethyl)-1H-imidazo[4,5-b]pyridin-2-yl)cyclobutyl)pyridin-3-yl)benzamide,
N-(6-(1-(1H-benzo[d]imidazol-2-yl)cyclobutyl)pyridin-3-yl)-3-cyanobenzamide,
3-chloro-N-(6-(1-(6-cyano-1H-benzo[d]imidazol-2-yl)cyclobutyl)pyridin-3-yl) benzamide, and
3-Chloro-N-(5-(1-(4,5,6,7-tetrahydro-1H-benzo[d]imidazol-2-yl)cyclobutyl)pyridin-2-yl)benzamide.

14. A composition which comprises an inert carrier and a compound of claim 1 or a pharmaceutically acceptable salt thereof.

15. A method for treating an IDO-associated disease or disorder in a mammalian subject which comprises administering to the subject an effective amount of a compound of claim 1 or a pharmaceutically acceptable salt thereof.

16. A method for treating an IDO-associated disease or disorder in a mammalian subject which comprises administering to the subject an effective amount of a compound of claim 1 or a pharmaceutically acceptable salt thereof in combination with another anti-cancer agent.

17. The method of claim 16, wherein the IDO-associated disease or disorder is a cancer, viral infection, HCV infection, depression, neurodegenerative disorders, trauma, age-related cataracts, organ transplantation, and autoimmune diseases.

18. The method of claim 17, wherein the cancer is a cancer of the colon, pancreas, breast, prostate, lung, brain, ovary, cervix, testes, renal, head and neck, lymphoma, leukemia, and melanoma.

* * * * *